(12) United States Patent
Campana et al.

(10) Patent No.: US 11,560,548 B2
(45) Date of Patent: *Jan. 24, 2023

(54) IMMUNE CELLS EXPRESSING MEMBRANE-BOUND INTERLEUKIN 15 (MBIL15) AND USES THEREOF

(71) Applicants: National University of Singapore, Singapore (SG); St. Jude Children's Research Hospital, Inc., Memphis, TN (US)

(72) Inventors: Dario Campana, Singapore (SG); David Shook, Memphis, TN (US); Masaru Imamura, Chuo-ku (JP)

(73) Assignees: National University of Singapore, Singapore (SG); St. Jude Children's Research Hospital, Inc., Memphis, TN (US)

( * ) Notice: Subject to any disclaimer, the term of this patent is extended or adjusted under 35 U.S.C. 154(b) by 120 days.

This patent is subject to a terminal disclaimer.

(21) Appl. No.: 16/986,742

(22) Filed: Aug. 6, 2020

(65) Prior Publication Data

US 2020/0407686 A1    Dec. 31, 2020

Related U.S. Application Data

(60) Continuation of application No. 16/550,548, filed on Aug. 26, 2019, now Pat. No. 10,774,311, which is a
(Continued)

(51) Int. Cl.
*A61K 38/20* (2006.01)
*C12N 5/0783* (2010.01)
(Continued)

(52) U.S. Cl.
CPC ............ *C12N 5/0646* (2013.01); *A61K 35/17* (2013.01); *A61K 38/2013* (2013.01);
(Continued)

(58) Field of Classification Search
None
See application file for complete search history.

(56) References Cited

U.S. PATENT DOCUMENTS

| 4,650,764 A | 3/1987 | Temin et al. |
| 4,690,915 A | 9/1987 | Rosenberg |

(Continued)

FOREIGN PATENT DOCUMENTS

| CN | 101684456 A | 3/2010 |
| CN | 103113470 A | 5/2013 |

(Continued)

OTHER PUBLICATIONS

Imai et al., Genetic modification of primary natural killer cells overcomes inhibitory signals and induces specific killing of leukemic cells Blood, 106(1):376-383, 2005.*

(Continued)

*Primary Examiner* — Claire Kaufman
(74) *Attorney, Agent, or Firm* — Hamilton, Brook, Smith & Reynolds, P.C.

(57) ABSTRACT

The present invention provides, in certain aspects, a natural killer (NK) cell that expresses all or a functional portion of interleukin-15 (IL-15), and methods for producing such cells. The invention further provides methods of using a natural killer (NK) cell that expresses all or a functional portion of interleukin-15 (IL-15) to treat cancer in a subject or to enhance expansion and/or survival of NK cells.

18 Claims, 13 Drawing Sheets

Specification includes a Sequence Listing.

Related U.S. Application Data division of application No. 15/309,362, filed as application No. PCT/SG2015/050111 on May 14, 2015, now Pat. No. 10,428,305.

(60) Provisional application No. 61/993,494, filed on May 15, 2014.

(51) Int. Cl.
 *A61K 35/17* (2015.01)
 *C12N 5/00* (2006.01)
 *C12N 15/62* (2006.01)
 *C07K 14/54* (2006.01)
 *C07K 14/705* (2006.01)

(52) U.S. Cl.
 CPC ...... *A61K 38/2086* (2013.01); *C07K 14/5443* (2013.01); *C07K 14/70517* (2013.01); *C12N 5/0006* (2013.01); *C12N 15/62* (2013.01); *C07K 2319/03* (2013.01); *C12N 2501/2315* (2013.01); *C12N 2510/00* (2013.01)

(56) References Cited

U.S. PATENT DOCUMENTS

| | | | |
|---|---|---|---|
| 4,844,893 A | 7/1989 | Honsik et al. | |
| 4,980,289 A | 12/1990 | Temin et al. | |
| 5,124,263 A | 6/1992 | Temin et al. | |
| 5,359,046 A | 10/1994 | Capon | |
| 5,399,346 A | 3/1995 | Anderson et al. | |
| 5,653,977 A | 8/1997 | Saleh | |
| 5,674,704 A | 10/1997 | Goodwin et al. | |
| 5,686,281 A | 11/1997 | Roberts | |
| 5,712,149 A | 1/1998 | Roberts | |
| 6,103,521 A | 8/2000 | Capon et al. | |
| 6,303,121 B1 | 10/2001 | Kwon | |
| 6,319,494 B1 | 11/2001 | Capon et al. | |
| 6,355,476 B1 | 3/2002 | Kwon et al. | |
| 6,410,319 B1 | 6/2002 | Raubitschek et al. | |
| 6,797,514 B2 | 9/2004 | Berenson et al. | |
| 7,052,906 B1 | 5/2006 | Lawson et al. | |
| 7,070,995 B2 | 7/2006 | Jensen | |
| 7,435,596 B2 | 10/2008 | Campana et al. | |
| 7,446,179 B2 | 11/2008 | Jensen et al. | |
| 7,446,190 B2 | 11/2008 | Sadelain et al. | |
| 7,763,243 B2 * | 7/2010 | Lum ................. | C07K 16/3007 424/178.1 |
| 7,994,298 B2 | 8/2011 | Zhang et al. | |
| 8,026,097 B2 | 9/2011 | Campana et al. | |
| 8,399,645 B2 | 3/2013 | Campana et al. | |
| 9,487,800 B2 | 11/2016 | Schonfeld et al. | |
| 9,605,049 B2 | 3/2017 | Campana et al. | |
| 9,834,590 B2 | 12/2017 | Campana et al. | |
| 9,856,322 B2 | 1/2018 | Campana et al. | |
| 10,428,305 B2 | 10/2019 | Campana et al. | |
| 10,774,311 B2 | 9/2020 | Campana et al. | |
| 11,365,236 B2 | 6/2022 | Leong et al. | |
| 2002/0018783 A1 | 2/2002 | Sadelain et al. | |
| 2003/0147869 A1 | 8/2003 | Riley | |
| 2003/0215427 A1 | 11/2003 | Jensen | |
| 2004/0038886 A1 | 2/2004 | Finney et al. | |
| 2004/0043401 A1 | 3/2004 | Sadelain et al. | |
| 2004/0126363 A1 | 7/2004 | Jensen et al. | |
| 2005/0042208 A1 | 2/2005 | Sagawa et al. | |
| 2005/0048549 A1 | 3/2005 | Cao et al. | |
| 2005/0113564 A1 | 5/2005 | Campana et al. | |
| 2006/0093605 A1 | 5/2006 | Campana et al. | |
| 2006/0247191 A1 | 11/2006 | Finney et al. | |
| 2007/0160578 A1 | 7/2007 | Waldmann et al. | |
| 2007/0166327 A1 | 7/2007 | Cooper et al. | |
| 2008/0247990 A1 | 10/2008 | Campbell | |
| 2012/0015434 A1 | 1/2012 | Campana et al. | |
| 2012/0148552 A1 | 6/2012 | Jensen | |
| 2012/0282256 A1 | 11/2012 | Campana et al. | |
| 2012/0321666 A1 | 12/2012 | Copper et al. | |
| 2013/0266551 A1 | 10/2013 | Campana et al. | |
| 2013/0280221 A1 | 10/2013 | Schonfeld et al. | |
| 2013/0288368 A1 | 10/2013 | June et al. | |
| 2014/0023626 A1 | 1/2014 | Peled et al. | |
| 2014/0271635 A1 | 9/2014 | Brogdon et al. | |
| 2014/0286973 A1 | 9/2014 | Powell, Jr. | |
| 2014/0302608 A1 | 10/2014 | Dominici et al. | |
| 2015/0139943 A1 | 5/2015 | Campana et al. | |
| 2015/0190471 A1 | 7/2015 | Copik et al. | |
| 2015/0218649 A1 | 8/2015 | Saenger et al. | |
| 2016/0000828 A1 | 1/2016 | Campana et al. | |
| 2016/0152723 A1 | 6/2016 | Chen et al. | |
| 2016/0158285 A1 | 6/2016 | Cooper et al. | |
| 2017/0044227 A1 | 2/2017 | Schonfeld | |
| 2017/0073423 A1 | 3/2017 | Juillerat et al. | |
| 2017/0073638 A1 | 3/2017 | Campana et al. | |
| 2017/0129967 A1 | 5/2017 | Wels et al. | |
| 2017/0283482 A1 | 10/2017 | Campana et al. | |
| 2017/0355957 A1 | 12/2017 | Biondi et al. | |
| 2018/0002397 A1 | 1/2018 | Shah et al. | |
| 2018/0044391 A1 | 2/2018 | Gundram et al. | |
| 2018/0086831 A1 | 3/2018 | Pule | |
| 2018/0104278 A1 | 4/2018 | Zhang et al. | |
| 2018/0117146 A1 | 5/2018 | Yu et al. | |
| 2018/0134765 A1 | 5/2018 | Landgraf et al. | |
| 2019/0038733 A1 | 2/2019 | Campana et al. | |
| 2019/0046571 A1 | 2/2019 | Campana et al. | |
| 2019/0290693 A1 | 9/2019 | Qi et al. | |
| 2019/0336533 A1 | 11/2019 | Hwang et al. | |
| 2019/0376037 A1 | 12/2019 | Campana et al. | |
| 2020/0016208 A1 | 1/2020 | Kamiya et al. | |
| 2020/0131244 A1 | 4/2020 | Leong et al. | |
| 2020/0255803 A1 | 8/2020 | Zhang et al. | |
| 2021/0017271 A1 | 1/2021 | Tan et al. | |
| 2021/0046115 A1 | 2/2021 | Seow et al. | |
| 2021/0054409 A1 | 2/2021 | Zhu et al. | |
| 2021/0324388 A1 | 10/2021 | Vinanica et al. | |

FOREIGN PATENT DOCUMENTS

| | | |
|---|---|---|
| CN | 105838677 A | 8/2016 |
| CN | 105985931 A | 10/2016 |
| CN | 107109363 A | 8/2017 |
| CN | 107827990 A | 3/2018 |
| EP | 0 952 213 A2 | 3/1999 |
| EP | 0 830 599 | 4/2000 |
| EP | 1 231 262 A1 | 8/2002 |
| EP | 1 306 427 A1 | 5/2003 |
| EP | 1 053 301 B1 | 4/2004 |
| EP | 1 820 017 | 6/2006 |
| EP | 1 233 058 B1 | 12/2006 |
| EP | 1 036 327 | 7/2009 |
| EP | 2 411 507 | 9/2010 |
| EP | 2 493 485 | 5/2011 |
| EP | 2 493 486 | 5/2011 |
| EP | 2 593 542 | 1/2012 |
| EP | 2 141 997 B1 | 10/2012 |
| EP | 2 614 151 | 10/2012 |
| EP | 2 756 521 | 3/2013 |
| EP | 2 866 834 | 1/2014 |
| EP | 2 903 637 | 4/2014 |
| EP | 2 904 106 | 4/2014 |
| EP | 2 948 544 | 7/2014 |
| EP | 2 956 175 | 8/2014 |
| EP | 2 961 831 | 9/2014 |
| EP | 2 964 753 | 9/2014 |
| EP | 2 970 426 | 9/2014 |
| EP | 2 968 601 | 10/2014 |
| EP | 2 986 636 | 10/2014 |
| EP | 2 537 416 B1 | 11/2014 |
| EP | 3 008 173 | 12/2014 |
| EP | 2 856 876 A1 | 4/2015 |
| EP | 3 057 986 | 4/2015 |
| EP | 3 063 175 | 5/2015 |
| EP | 3 071 221 | 5/2015 |
| EP | 3 071 222 | 5/2015 |
| EP | 3 071 223 | 5/2015 |
| EP | 3 083 671 | 6/2015 |

(56) References Cited

FOREIGN PATENT DOCUMENTS

| | | |
|---|---|---|
| EP | 3 083 691 | 6/2015 |
| EP | 3 094 653 | 7/2015 |
| EP | 3 105 318 | 8/2015 |
| EP | 3 105 335 | 8/2015 |
| EP | 2 968 492 | 9/2015 |
| EP | 3 119 425 | 9/2015 |
| EP | 3 126 380 | 10/2015 |
| EP | 3 134 432 | 10/2015 |
| EP | 3 180 359 | 2/2016 |
| EP | 3 189 132 | 3/2016 |
| EP | 3 012 268 A1 | 4/2016 |
| EP | 2 614 077 B1 | 8/2016 |
| EP | 3 115 373 A1 | 1/2017 |
| EP | 3 567 049 A2 | 11/2019 |
| JP | 2017-112982 A | 6/2017 |
| WO | WO 92/17198 A1 | 10/1992 |
| WO | WO 95/007358 A1 | 3/1995 |
| WO | WO 96/023814 A1 | 8/1996 |
| WO | WO 96/024671 A1 | 8/1996 |
| WO | WO 96/41163 A1 | 12/1996 |
| WO | WO 97/023613 A2 | 7/1997 |
| WO | WO 98/026061 A1 | 6/1998 |
| WO | WO 99/000494 A2 | 1/1999 |
| WO | WO 99/06557 A2 | 2/1999 |
| WO | WO 99/38954 A1 | 8/1999 |
| WO | WO 99/057268 A1 | 11/1999 |
| WO | WO 2000/014257 A1 | 3/2000 |
| WO | WO 00/23573 A2 | 4/2000 |
| WO | WO 01/29191 A1 | 4/2001 |
| WO | WO 01/38494 A1 | 5/2001 |
| WO | WO 02/10350 A1 | 2/2002 |
| WO | WO 02/033101 A1 | 4/2002 |
| WO | WO 02/077029 A2 | 10/2002 |
| WO | WO 03/089616 A2 | 10/2003 |
| WO | WO 2004/027036 A2 | 4/2004 |
| WO | WO 2004/039840 A1 | 5/2004 |
| WO | 2005/000890 A1 | 1/2005 |
| WO | WO 2005/044996 A2 | 5/2005 |
| WO | WO 2005/118788 A2 | 12/2005 |
| WO | WO 2006/036445 A2 | 4/2006 |
| WO | WO 2006/052534 A2 | 5/2006 |
| WO | WO 2006/061626 A2 | 6/2006 |
| WO | WO 2007/046006 A2 | 4/2007 |
| WO | WO 2008/121420 A1 | 10/2008 |
| WO | WO 2009/117566 A1 | 9/2009 |
| WO | WO 2010/071836 A1 | 6/2010 |
| WO | WO 2010/110734 A1 | 9/2010 |
| WO | WO 2011/020047 A1 | 2/2011 |
| WO | WO 2011/053321 A1 | 5/2011 |
| WO | WO 2011/053322 A1 | 5/2011 |
| WO | WO 2011/069019 A2 | 6/2011 |
| WO | WO 2011/080740 A1 | 7/2011 |
| WO | WO 2011/150976 A1 | 12/2011 |
| WO | WO 2012/009422 A1 | 1/2012 |
| WO | WO 2012/031744 A1 | 3/2012 |
| WO | WO 2012/040323 A2 | 3/2012 |
| WO | WO 2012/071411 A2 | 5/2012 |
| WO | WO 2012/079000 A1 | 6/2012 |
| WO | WO 2012/136231 A1 | 10/2012 |
| WO | 2013/043196 A | 3/2013 |
| WO | WO 2013/040371 A2 | 3/2013 |
| WO | WO 2013/040557 A2 | 3/2013 |
| WO | WO 2013/123720 A2 | 8/2013 |
| WO | WO 2013/123726 A1 | 8/2013 |
| WO | WO 2014/005072 A1 | 1/2014 |
| WO | WO 2014/011993 A2 | 1/2014 |
| WO | WO 2014/055413 A2 | 4/2014 |
| WO | WO 2014/055442 A2 | 4/2014 |
| WO | WO 2014/055657 A1 | 4/2014 |
| WO | WO 2014/055668 A1 | 4/2014 |
| WO | WO 2014/099671 A1 | 6/2014 |
| WO | WO 2014/117121 A1 | 7/2014 |
| WO | WO 2014/127261 A1 | 8/2014 |
| WO | WO 2014/134165 A1 | 9/2014 |
| WO | WO 2014/138704 A1 | 9/2014 |
| WO | WO 2014/145252 A2 | 9/2014 |
| WO | WO 2014/164554 A1 | 10/2014 |
| WO | WO 2014/172584 A1 | 10/2014 |
| WO | WO 2014/186469 A2 | 11/2014 |
| WO | WO 2014/201021 A2 | 12/2014 |
| WO | WO 2015/058018 A1 | 4/2015 |
| WO | WO 2015/066551 A2 | 5/2015 |
| WO | WO 2015/075468 A1 | 5/2015 |
| WO | WO 2015/075469 A1 | 5/2015 |
| WO | WO 2015/075470 A1 | 5/2015 |
| WO | WO 2015/092024 A2 | 6/2015 |
| WO | WO 2015/095895 A1 | 6/2015 |
| WO | WO 2015/105522 A1 | 7/2015 |
| WO | WO 2015/120421 A1 | 8/2015 |
| WO | WO 2015/123642 A1 | 8/2015 |
| WO | WO 2015/142314 A1 | 9/2015 |
| WO | WO 2015/142661 A1 | 9/2015 |
| WO | WO 2015/150771 A1 | 10/2015 |
| WO | WO 2015/154012 A1 | 10/2015 |
| WO | WO 2015/154012 A8 | 10/2015 |
| WO | WO 2015/164759 A2 | 10/2015 |
| WO | WO 2015/174928 A1 | 11/2015 |
| WO | WO 2015/193411 A1 | 12/2015 |
| WO | WO 2016/011210 A2 | 1/2016 |
| WO | WO 2016/030691 A1 | 3/2016 |
| WO | WO 2016/033331 A1 | 3/2016 |
| WO | WO 2016/040441 A1 | 3/2016 |
| WO | WO 2016/042041 A1 | 3/2016 |
| WO | WO 2016/042461 A1 | 3/2016 |
| WO | WO 2016/061574 A1 | 4/2016 |
| WO | WO 2016/069607 A1 | 5/2016 |
| WO | WO 2016/073602 A2 | 5/2016 |
| WO | WO 2016/073629 A1 | 5/2016 |
| WO | WO 2016/073755 A2 | 5/2016 |
| WO | WO 2016/075612 A1 | 5/2016 |
| WO | WO 2016/100985 A2 | 6/2016 |
| WO | 2016/118857 A1 | 7/2016 |
| WO | WO 2016/109661 A1 | 7/2016 |
| WO | WO 2016/109668 A1 | 7/2016 |
| WO | WO 2016/115482 A1 | 7/2016 |
| WO | WO 2016/123122 A1 | 8/2016 |
| WO | WO 2016/123333 A1 | 8/2016 |
| WO | WO 2016/124765 A1 | 8/2016 |
| WO | WO 2016/124930 A1 | 8/2016 |
| WO | WO 2016/126213 A1 | 8/2016 |
| WO | WO 2016/126608 A1 | 8/2016 |
| WO | 2016/139487 A1 | 9/2016 |
| WO | WO 2016/141357 A1 | 9/2016 |
| WO | WO 2016/142314 A1 | 9/2016 |
| WO | WO 2016/149254 A1 | 9/2016 |
| WO | WO 2016/151315 A1 | 9/2016 |
| WO | WO 2016/154055 A2 | 9/2016 |
| WO | WO 2016/154585 A1 | 9/2016 |
| WO | WO 2016/172537 A1 | 10/2016 |
| WO | WO 2016/172583 A1 | 10/2016 |
| WO | WO 2016/174405 A1 | 11/2016 |
| WO | WO 2016/174406 A1 | 11/2016 |
| WO | WO 2016/174407 A1 | 11/2016 |
| WO | WO 2016/174408 A1 | 11/2016 |
| WO | WO 2016/174409 A1 | 11/2016 |
| WO | WO 2016/174461 A1 | 11/2016 |
| WO | WO 2016/174652 A1 | 11/2016 |
| WO | WO 2016/179684 A1 | 11/2016 |
| WO | WO 2016/191587 A1 | 12/2016 |
| WO | WO 2016/191755 A1 | 12/2016 |
| WO | WO 2016/196388 A1 | 12/2016 |
| WO | WO 2016/197108 A1 | 12/2016 |
| WO | WO 2016/201304 A1 | 12/2016 |
| WO | WO 2016/210293 A1 | 12/2016 |
| WO | WO 2017/004150 A1 | 1/2017 |
| WO | WO 2017/011804 A1 | 1/2017 |
| WO | WO 2017/021701 A1 | 2/2017 |
| WO | WO 2017/023859 A1 | 2/2017 |
| WO | WO 2017/024131 A1 | 2/2017 |
| WO | WO 2017/027325 A1 | 2/2017 |
| WO | WO 2017/029511 A1 | 2/2017 |
| WO | WO 2017/032777 A1 | 3/2017 |
| WO | WO 2017/034615 A1 | 3/2017 |
| WO | WO 2017/037083 A1 | 3/2017 |

(56) References Cited

FOREIGN PATENT DOCUMENTS

| WO | WO 2017/058752 A1 | 4/2017 |
|---|---|---|
| WO | WO 2017/058753 A1 | 4/2017 |
| WO | WO 2017/079694 A2 | 5/2017 |
| WO | WO 2017/079705 A1 | 5/2017 |
| WO | WO 2017/079881 A1 | 5/2017 |
| WO | WO 2017/096329 A1 | 6/2017 |
| WO | WO 2017/127729 A1 | 7/2017 |
| WO | WO 2017/172981 A2 | 10/2017 |
| WO | WO 2018/022646 A1 | 2/2018 |
| WO | 2018/106732 A1 | 6/2018 |
| WO | WO 2018/103503 A1 | 6/2018 |
| WO | WO 2018/182511 A1 | 10/2018 |
| WO | WO 2018/183385 A1 | 10/2018 |
| WO | WO 2019/062817 A1 | 4/2019 |
| WO | WO 2019/077037 A1 | 4/2019 |
| WO | WO 2019/129002 A1 | 7/2019 |
| WO | WO 2019/155286 A2 | 8/2019 |
| WO | WO 2019/155288 A1 | 8/2019 |
| WO | WO 2019/193476 A1 | 10/2019 |
| WO | WO 2020/044239 A1 | 3/2020 |
| WO | WO 2020/083282 A1 | 4/2020 |
| WO | WO 2021/009694 A1 | 1/2021 |

OTHER PUBLICATIONS

GenBank Database, Accession # NM_172175.2, *Homo sapiens* interleukin 15 (IL15), trasncript variant 2, mRNA, [accessed Feb. 24, 2022], Feb. 12, 2011.*

Pakula, A. A. et al., "Genetic analysis of protein stability and function," Annual Review of Genetics, V. 23, N. 1, p. 289-310, c. 305-306 (1989).

Caratelli et al., "FCy Chimeric Receptor-Engineered T Cells: Methodology, Advantages, Limitations, and Clinical Relevance," Front Immunol., vol. 8, Article 457, 8 pages (Apr. 27, 2017).

Hombach, A.A., et al., "Costimulation by chimeric antigen receptors revisited: the T cell antitumor response benefits from combined CD28-OX40 signalling", Int. J. Cancer, 129, 2935-2944 (2011).

Hurton, L.V. et al., "Tethered IL-15 augments antitumor activity and promotes a stem-cell memory subset in tumor-specific T cells," PCNAS, USA, 113(48): E7788-E7797 (Nov. 2016).

Kober, J., et al. "The capacity of the TNF family members 4-1BBL, OX40L, CD70, GITRL, CD30L and LIGHT to costimulate human T cells," Eur J Immuno, vol. 38, No. 10, pp. 2678-2688 (Oct. 28, 2008).

NCIthesaurus, Bicistronic chimeric antigen reeptor vector, retrieved online from: https://ncit.nci.nih.gov/ncitbrowser/pages/home.jsf.jsessionid=12B0F7AF71E9A4035C38B5E4F6C055B0, retrieved on: Jan. 21, 2021.

Abken et al., "Chimeric T-cell receptors: highly specific tools to target cytotoxic T-lymphocytes to tumour cells," Cancer Treat Rev., 23(2):97-112, Mar. 1997.

Abken, H., et al., "Tuning tumor-specific T-cell activation: a matter of costimulation?" TRENDS in Immunol. 23: 240-245 (2002).

Aguera-Gonzalez et al., "Palmitoylation of MICA, a ligand for NKG2D, mediates its recruitment to membrane microdomams and promotes its shedding," Eur. J. Immunol. vol. 41, pp. 3667-3676 (2011).

Alderson et al., "Molecular and Biological Characterization of Human 4-1BB and its Ligand," Eur. J. Immunol., 1994, 24: 2219-2227.

Allison and Lanier, "Structure, function, and serology of the T-cell antigen receptor complex," Annu Rev Immunol, 1987, 5:503-40.

Alvarez-Vallina, L. and Hawkins. R.E., "Antigen-specific targeting of CD28-mediated T cell costimulation using chimeric single-chain antibody variable fragment-CD28 receptors," Eur. J. Immunol. 26: 2304-2309 (1996).

Ang, S.O et al, "Avoiding the need for clinical-grade OKT3: ex vivo expansion of T cells using artificial antigen presenting cells genetically modified to crosslink CD3" Biology of Blood and Marrow Transplantation, Jan. 9, 2012, vol. 8, No. 2, pp. S258.

Annenkov, A., et al., "Engineering mouse T lymphocytes specific to type II collagen by transduction with a chimeric receptor consisting of a single chain Fv and TCR zeta," Gene Therapy 7: 714-722 (2000).

Antony, G.K., et al., "Interleukin 2 in cancer therapv," Curr Med Chem., 17(29): 3297-3302 (2010).

Aoudjit and Vuori., "Integrin Signaling in Cancer Cell Survival and Chemoresistance," Chemotherapy Research and Practice., 2012(Article ID 283181), 16 pages, 2012.

Appelbaum, "Haematopoietic cell transplantation as immunotherapy," Nature, 2001, 411(6835): 385-389.

Aruffo, A., et al., "Molecular cloning of a CD28 cDNA by a high-efficiency COS cell expression system," Proc. Natl. Acad. Sci., 1987, 84:8573-8577.

ATCC No. CCL-243, 1975.

Azuma, M, et al., "Functional Expression of B7/BB1 on Activated T Lymphocytes," J. Exp. Med. 177: 845-850 (1993).

Baek, H.J. et al., "Ex vivo expansion of natural killer cells using cryopreserved irradiated feeder cells," *Anticancer Research*, 33: 2011-2020 (2013).

Barber et al., "Chimeric NKG2D Expressing T Cells Eliminate Immunosuppression and Activate Immunity within the Ovarian Tumor Microenvironment," J. Immunol, vol. 183, pp. 6939-6947 (2009).

Barber et al., "Chimeric NKG2D Receptor-Bearing T Cells as Immunotherapy for Ovarian Cancer," American Association for Cancer, vol. 67, No. 10, pp. 5003-5008, (May 15, 2007).

Barber et al., "Chimeric NKG2D receptor-expressing T cells as an immunotherapy for multiple myeloma," Experimental Hematology, vol. 36, pp. 1318-1328, (2008).

Barber et al., "Chimeric NKG2D T Cells Require Both T Cell- and Host-Derived Cytokine Secretion and Perform Expression to Increase Tumor Antigen Presentation and Systemic Immunity," J. Immunol, vol. 183, pp. 2365-2372 (2009).

Barber et al., "Immunotherapy with Chimeric NKG2D Receptors Leads to Long-Term Tumor-Free Survival and Development of Host Antitumor Immunity in Murine Ovarian Cancer," J. Immunol., vol. 180, pp. 72-78, (2008).

Barber et al., "Treatment of multiple myeloma with adoptively transferred chimeric NKG2D receptor-expressing T cells," Gene Therapy, vol. 18, pp. 509-516, (2011).

Barrett, D.M., et al., "Chimeric Antigen Receptor Therapy for Cancer," Annu Rev. Med. 65: 333-347 (2014).

Bartholomew et al., "Mesenchymal stem cells suppress lymphocyte proliferation in vitro and prolong skin graft survival in vivo," Exp Hematol, Jan. 2002, 30(1): 42-8.

Batlevi, C.L., et al. "Novel immunotherapies in lymphoid malignancies," Nature Rev. Clin. Oncol.13:25-40 (2016).

Baum et al., "Side effects of retroviral gene transfer into hematopoietic stem cells," Blood, Mar. 2003, 101(6): 2099-114.

Bejcek et al., "Development and Characterization of Three Recombinant Single Chain Antibody Fragments (scFvs) Directed against the CD19 Antigen," Cancer Res., 1995, 55:2346-2351.

Berger, C. et al., "Safety and immunologic effects of IL-15 administration in nonhuman primates," *Blood*, 114(12): 2417-2426 (2009).

Besser, M.J., et al., "Adoptive Transfer of Tumor-Infiltrating Lymphocytes in Patients with Metastatic Melanoma: Intent-to-Treat Analysis and Efficacy after Failure to Prior Immunotherapies," Clin. Cancer Res. 19: 4792-4800 (2013).

Better et al., "Manufacturing and Characterization of KTE-C19 in a Multicenter Trial of Subjects with Refractory Aggressive Non-Hodgkin Lymphoma (NHL) (ZUMA-1)," Poster session presented at the American Association for Cancer Research Annual Meeting, New Orleans, Louisiana (2016).

Billadeau et al., "NKG2D-DAP10 triggers human NK cell-mediated killing via a Syk-independent regulatory pathway," Nat Immunol, Jun. 2003, 4(6): 557-64.

Bischof et al., "Autonomous induction of proliferation, JNK and NF-xB activation in primary resting T cells by mobilized CD28," Eur J Immunol, 30(3):876-882, Mar. 2000.

Bork et al., "The immunoglobulin fold. Structural classification, sequence patterns and common core," J Mol Biol., 242(4):309-320, Sep. 30, 1994.

(56) References Cited

OTHER PUBLICATIONS

Boyman, O., et al., "The role of interleukin-2 during homeostasis and activation of the immune system," Nat Rev Immunol., 12: 180-190 (2012).

Brand, L.J. et al., "Abstract LB-185: A PSMA-directed natural killer cell approach for prostate cancer immunotherapy," Cancer Research, 77(13 Supplement): Abstract No. LB-185 (Jul. 2017).

Brentjens et al., "Eradication of Systemic B-Cell Tumors by Genetically Targeted Human T Lymphocytes Co-Stimulated By CD80 and Interleukin-15," Nature Medicine, 2003, 9: 279-286.

Brentjens, R.J., et al., "CD19-Targeted T Cells Rapidly Induce Molecular Remissions in Adults with Chemotherapy-Refractory Acute Lymphoblastic Leukemia," Sci. Trans. Med. 5: 1-9 (2013).

Brentjens, R.J., et al., "Safety and persistence of adoptively transferred autologous CD19-targeted T cells in patients with relapsed or chemotherapy refractory B-cell leukemias," Blood 119(18): 4817-4828 (2011).

Bridgeman, J.S., et al., "Building Better Chimeric Antigen Receptors for Adoptive T Cell Therapy," Current Gene Therapy 10: 77-90 (2010).

Bridgeman, J.S. et al., "The Optimal Antigen Response of Chimeric Antigen Receptors Harboring the CD3ζ Transmembrane Domain is Dependent upon Incorporation of the Receptor into the Endogenous TCR/CD3 Complex," J Immunol, 184(12): 6938-6949 (May 2010).

Brocker et al., "New simplified molecular design for functional T cell receptor," Eur J Immunol., 23(7): 1435-1439, Jul. 1993.

Bromley et al., "The immunological synapse and CD28-CD80 interactions," Nat Immunol., 2(12):1159-1166, Dec. 2001.

Bronte, V., and Mocellin, S., "Suppressive Influences in the Immune Response to Cancer," J. Immunother . 32: 1-11 (2009).

Budagian, V. et al., "IL-15/IL-15 receptor biology: A guided tour through an expanding universe," Cytokine & Growth Factor Reviews, 17: 259-280 (2006).

Bukczynski et al., "Costimulation of Human CD28-T Cells by 4-1BB Ligand," Eur. J. Immunol., 2003, 33: 446-454.

Burkett, P.R. et al., "Coordinate expression and trans presentation of interleukin (IL)-15Ralpha and IL-15 supports natural killer cell and memory CD8+ T cell homeostasis," J Exp Med., 200(7): 825-834 (2004).

Caligiuri et al., "Immunotherapeutic approaches for hematologic malignancies," Hematology Am Soc Hematol Educ Program, 2004, 37-53.

Campana et al., "Immunophenotyping of Leukemia," Journal of Immunol Methods, 2000, 243: 59-75.

Cardoso AA, et al. Pre-B acute lymphoblastic leukemia cells may induce T-cell anergy to alloantigen. Blood 88:41-48 (1996).

Carson, W.E. et al., "A potential role for interleukin-15 in the regulation of human natural killer cell survival," J Clin Invest., 99(5): 937-943 (1997).

Carter, P., et al. ., "Identification and validation of cell surface antigens for antibody targeting in oncology," Endocrine-Related Cancer 11: 659-687 (2004).

Cesano, A., et al. "Reversal of Acute Myelogenous Leukemia in Humanized SCID Mice Using a Novel Adoptive Transfer Approach," J. Clin. Invest. 94: 1076-1084 (1994).

Chambers, C.A., "The expanding world of co-stimulation: the two-signal model revisited," TRENDS in Immunol., 2001, 22(4):217-223.

Champlin R. "T-cell depletion to prevent graft-versus-host disease after bone marrow transplantation," Hematol Oncol Clin North Am. Jun. 1990;4(3):687-98.

Chang et al., "Five Different Anti-Prostate-specific Membrane Antigen (PSMA) Antibodies Confirm PSMA Expression in Tumor-associated Neovasculature," Cancer Res., 59: 3192-3198 (1999).

Chang, Y.H. et al., "A chimeric receptor with NKG2D specificity enhances natural killer cell activation and killing of tumor cells," Cancer Res., 73(6): 1777-1786 (2013).

Chao, D.T. et al., "BCL-2 family: regulators of cell death," Annu Rev Immunol., 16: 395-419 (1998).

Cheresh et al., "Disialogangliosides GD2 and GD3 Are Involved in the Attachment of Human Melanoma and Neuroblastoma Cells to Extracellular Matrix Proteins," J Cell Biol. 1986, 102(3):688-696.

Chertova, E. et al., "Characterization and favorable in vivo properties of heterodimeric soluble IL-15.IL-15Ralpha cytokine compared to IL-15 monomer," J Biol Chem., 288(25): 18093-18103 (2013).

Cheung et al., "Anti-Idiotypic Antibody Facilitates scFv Chimeric Immune Receptor-Gene Transduction and Clonal Expansion of Human Lymphocytes for Tumor Therapy," Hybridoma and Hybndomics, 2003, 24(4): 209-218.

Chiorean and Miller, "Tire biology of natural killer cells and implications for therapy of human disease," J Hematother Stem Cell Res, Aug. 2001, 10(4): 451-63.

Cho, D., and D. Campana, "Expansion and activation of natural killer cells for cancer immunotherapy," The Korean Journal of Laboratory Medicine, 29(2): 89-96 (2009).

Clarke et al., "Folding studies of immunoglobulin-like beta-sandwich proteins suggest that they share a common folding pathway," Structure, 7(9):1145-1153, Sep. 15, 1999.

ClinicalTrials.gov, "A Multi-Center Study Evaluating KTE-C19 in Pediatric and Adolescent Subjects With Relapsed/Refractory B-precursor Acute Lymphoblastic Leukemia (ZUMA-4)," available at https://clinicaltnals.gov/show/NCT02625480, NCT02625480 (Retneved from the Internet on Jun. 21, 2016).

ClinicalTrials.gov, "A Phase 1-2 Multi-Center Studv Evaluating KTE-C19 in Subjects With Refractory Aggressive Non-Hodgkm Lymphoma (ZUMA-1) (ZUMA-1)," available at https://clinicaltrials.gov/show/NCT02348216, NCT02348216 (Retrieved from the Internet on Jun. 21, 2016).

ClinicalTrials.gov, "A Phase 2 Multicenter Study Evaluating Subjects With Relapsed/Refractory Mantle Cell Lymphoma (ZUMA-2)," available at https://clinicaltrials.gov/show/NCT02601313, NCT02601313 (Retrieved from the Internet on Jun. 21, 2016).

ClinicalTrials.gov, "A Study Evaluating KTE-C19 in Adult Subjects With Relapsed/Refractory B-precursor Acute Lymphoblastic Leukemia (r/r ALL) (ZUMA-3) (ZUMA-3)," available at https://clinicaltrials.gov/show/NCT02614066, NCT02614066 (Retrieved from the Internet on Jun. 21, 2016).

ClinicalTrials.gov, "Administration of Anti-CD19-chimeric-antigen-receptor-transduced T Cells From the Original Transplant Donor to Patients With Recurrent or Persistent B-cell Malignancies After Allogeneic Stem Cell Transplantation," available at https://clinicaltrials.gov/show/NCT01087294, NCT01087294 (Retrieved from the Internet on Jun. 21, 2016).

ClinicalTrials.gov, "Anti-CD19 White Blood Cells for Children and Young Adults With B Cell Leukemia or Lymphoma," available at https://clinicaltrials.gov/show/NCT01593696, NCT01593696 (Retrieved from the Internet on Jun. 21, 2016).

ClinicalTrials.gov, "Car T Cell Receptor Immunotherapy for Patients With B-cell Lymphoma," available at https://clinicaltrials.gov/show/NCT00924326, NCT00924326 (Retrieved from the Internet on Jun. 21, 2016).

ClinicalTrials.gov, "CD19 Cart Cells for B Cell Malignancies After Allogeneic Transplant," available at https://clinicaltrials.gov/show/NCT01475058, NCT01475058 (Retrieved from the Internet on Jun. 21, 2016).

ClinicalTrials.gov, "CD19 Chimeric Receptor Expressing T Lymphocytes In B-Cell Non Hodgkin's Lymphoma, ALL & CLL (CRETI-NH)," available at https://clinicaltrials.gov/show/NCT00586391, NCT00586391 (Retrieved from the Internet on Jun. 21, 2016).

ClinicalTrials.gov, "CD19+ Cart Cells for Lymphoid Malignancies." available at https://clinicaltrials.gov/show/NCT02529813, NCT02529813 (Retrieved from the Internet on Jun. 21, 2016).

ClinicalTrials.gov, "Consolidation Therapy With Autologous T Cells Genetically Targeted to the B Cell Specific Antigen CD19 in Patients With Chronic Lymphocytic Leukemia Following Upfront Chemotherapy With Pentostatin, Cyclophosphamide and Rituximab," available at https://clinicaltrials.gov/show/NCT01416974, NCT01416974 (Retrieved from the Internet on Jun. 21, 2016).

ClinicalTrials.gov, "Genetically Engineered Lymphocyte Therapy in Treating Patients With B-Cell Leukemia or Lymphoma That is

(56) References Cited

OTHER PUBLICATIONS

Resistant or Refractory to Chemotherapy," available at https://clinicaltrials.gov/show/NCT01029366, NCT01029366 (Retrieved from the Internet on Jun. 21, 2016).
ClinicalTrials.gov, "High Dose Therapy and Autologous Stem Cell Transplantation Followed by Infusion of Chimeric Antigen Receptor (CAR) Modified T-Cells Directed Against CD19+ B-Cells for Relapsed and Refractory Aggressive B Cell Non-Hodgkin Lymphoma," available at https://clinicaltrials.gov/show/NCT01840566, NCT01840566 (Retrieved from the Internet on Jun. 21, 2016).
ClinicalTrials.gov, "In Vitro Expanded Allogeneic Epstein-Barr Virus Specific Cytotoxic T-Lymphocytes (EBV-CTLs) Genetically Targeted to the CD 19 Antigen in B-ccll Malignancies," available at https://clinicaltrials.gov/show/NCT01430390, NCT01430390 (Retrieved from the Internet on Jun. 21, 2016).
ClinicalTrials.gov, "Precursor B Cell Acute Lymphoblastic Leukemia (B-ALL) Treated With Autologous T Cells Genetically Targeted to the B Cell Specific Antigen CD19," available at https://clinicaltrials.gov/show/NCT01044069, NCT01044069 (Retrieved from the Internet on Jun. 21, 2016).
ClinicalTrials.gov, "Study Evaluating the Efficacy and Safety of JCAR015 in Adult B-cell Acute Lymphoblastic Leukemia (B-ALL) (ROCKET)," available at https://clinicaltrials.gov/show/NCT02535364, NCT02535364 (Retrieved from the Internet on Jun. 21, 2016).
ClinicalTrials.gov, "T Cells Expressing a Fully-human AntiCD19 Chimeric Antigen Receptor for Treating B-cell Malignancies," available at https://clinicaltrials.gov/show/NCT02659943, NCT02659943(Retrieved from the Internet on Jun. 21, 2016).
ClinicalTrials.gov, "T-Lymphocytes Genetically Targeted to the B-Cell Specific Antigen CD19 in Pediatric and Young Adult Patients With Relapsed B-Cell Acute Lymphoblastic Leukemia," available at https://clinicaltrials.gov/show/NCT01860937, NCT01860937(Retrieved from the Internet on Jun. 21, 2016).
ClinicalTrials.gov, "Treatment of Relapsed or Chemotherapy Refractory Chronic Lymphocytic Leukemia or Indolent B Cell Lymphoma Using Autologous T Cells Genetically Targeted to the B Cell Specific Antigen CD19", Available at: https://clinicaltrials.gov/show/NCT00466531, NCT00466531 (Retrieved from the Internet on Jun. 21, 2016).
Cochran et al., "Receptor clustering and transmembrane signaling in T cells," Trends Biochem Sci., 26(5):304-310, May 2001.
Collins et al., "Donor leukocyte infusions in 140 patients with relapsed malignancy after allogeneic bone marrow transplantation," J Clin Oncol, Feb. 1997, 15(2): 433-44.
Collins et al., "Donor leukocyte infusions in acute lymphocytic leukemia." Bone Marrow Transplantation, 2000, 26: 511-516.
Communication Pursuant to Article 94(3) EPC of Application No. 14743792.5 dated Jun. 9, 2017.
Cooley, S. et al., "Donor selection for natural killer cell receptor genes leads to superior survival after unrelated transplantation for acute myelogenous leukemia," Blood, 116(14): 2411-2419 (2010).
Cooper et al., "T-Cell Clones can be Rendered Specific for CD19: Toward the Selective Augmentation Of the Graft-Versus-B Lineage Leukemia Effect," Blood, 2003, pp. 1637-1644, vol. 101.
Cooper, M.A. et al., "In vivo evidence for a dependence on interleukin 15 for survival of natural killer cells," *Blood*, 100(10): 3633-3638 (2002).
Cruz et al., "Infusion of donor-denved CD19-redirected virus-specific T cells for B-cell malignancies relapsed after allogeneic stem cell transplant: a phase 1 study," Blood 122(17):2965-2973 (2013).
Curti, A. et al., "Successful transfer of alloreactive haploidentical KIR ligand-mismatched natural killer cells after infusion in elderly high risk acute myeloid leukemia patients," Blood, 118(12): 3273-3279 (2011).
Damle et al., "Differential regulatory signals delivered by antibody binding to the CD28 (Tp44) molecule during the activation of human T lymphocytes," J Immunol., 140(6): 1753-1761, Mar. 15, 1988.

Darcy, P.K., et al., "Expression in cytotoxic T lymphocytes of a single-cham anti-carcinoembryonic antigen antibody. Redirected Fas ligand-mediated lysis of colon carcinoma," Eur. J. Immunol. 28: 1663-1672 (1998).
Davila, M.L., et al., "Efficacy and Toxicity Management of 19-28z CAR T Cell Therapy in B Cell Acute Lymphoblastic Leukemia," Science Translat. Med. 6(24) (2014).
De La Chapelle, A. et al., "Truncated erythropoietin receptor causes dominantly inhented benign human erythrocytosis," Proc Natl Acad Sci USA., vol. 90, No. 10, pp. 4495-4499 (May 1993).
DeBenedette et al., "Role of 4-1BB ligand in costimulation of T lymphocyte growth and its upregulation on M12 B lymphomas by cAMP," J Exp Med, Mar. 1995, 181(3): 985-92.
DeBenedette, MA, et al.. "Costimulation of CD28-T Lymphocytes by 4-1 BB Ligand," J. Immunol., 1997, pp. 551-559, vol. 158.
Delahaye, N.F. et al., "Alternatively spliced NKp30 isoforms affect the prognosis of gastrointestinal stromal tumors," *Nat Med.*, 17(6): 700-707 (2011).
Diefenbach et al., "Selective associations with signaling proteins determine stimulatory versus costimulatory activity of NKG2D," Nature Publishing Group, vol. 3, No. 12, pp. 1142-1149, (Dec. 2002).
Dotti et al., "Design and Development of Therapies using Chimeric Antigen Receptor-Expressing T cells," Immunol Rev., 257(1), 35 pages, Jan. 2014.
Doubrovian, et al., "Evasion from NK Cell Immunity by MHC Class I Chain-Related Molecules Expressing Colon Adenocarcinoma," Journal of Immunology, vol. 171, pp. 689-6899, (2003).
Dubois et al., "IL-15Rα recycles and presents IL-15 In trans to neighboring cells," Immunity, Nov. 2002, 17(5): 537-47.
Dubois, S., et al., "Preassociation of IL-15 with IL-15R alpha-IgG1-Fc enhances its activity on proliferation of NK and CD8+/CD44high T cells and its antitumor action," Journal of Immunology, 180(4):2099-2106 (2008).
Dudley, M.E., et al., "Adoptive Transfer of Cloned Melanoma-Reactive T Lymphocytes for the Treatment of Patients with Metastatic Melanoma," J. Immunother. 24: 363-373 (2001).
Ellis et al., "Interactions of CD80 and CD86 with CD28 and CTLA4," J Immunol., 156(8):2700-2709, Apr. 15, 1996.
Eshhar et al., "Specific activation and targeting of cytotoxic lymphocytes through chimeric single chains consisting of antibody-binding domains and the γ or ζ subunits of the immunoglobulin and T-cell receptors," Proc. Natl. Acad. Sci. USA, 1993, 90:720-724.
Eshhar, Z, et al . "Functional Expression of Chimeric Receptor Genes in Human T Cells," J. Immunol. Methods, 2001, 248(1-2):67-76.
Eshhar, Z., "Tumor-specific T-bodies: towards clinical application," Cancer Immunol. Immunother. 45: 131-136 (1997).
European Extended Search Report dated Jul. 5, 2016 for European Application No. 14743792.5, 6 pages.
Fagan, E.A., and Eddleston, A.L.W.F., "Immunotherapy for cancer: the use of lymphokine activated killer (LAK) cells," Gut 28: 113-116 (1987).
Farag et al., "Natural killer cell receptors: new biology and insights into the Graft-versus-leukemia effect," Blood, 2002, 100(6):1935-1947.
Fehniger TA, et al.; "Ontogeny and expansion of human natural killer cells: clinical implications", Int Rev Immunol. Jun. 2001; 20(3-4):503-534.
Fehniger, T.A., et al., "Interleukin 15: biology and relevance to human disease," Blood, 97(1): 14-32 (2001).
Ferlazzo, G. et al., "Distinct roles of IL-12 and IL-15 in human natural killer cell activation by dendritic cells from secondary lymphoid organs," PNAS, 101(47): 16606-16611 (2004).
Fernandez-Messina et al., "Human NKG2D-ligands: cell biology strategies ensure immune recognition," Frontiers in Immunology, vol. 3, Article 299, 9 Pages, (Sep. 2012).
Ferris, R.L. et al., "Tumor antigen-targeted, monoclonal antibody-based immunotherapy: clinical response, cellular immunity, and immunoescape," *J Clin Oncol*, 28(28): 4390-4399 (2010).
Finney et al., "Activation of resting human primary T cells with chimeric receptors: costimulation from CD28, inducible costimula-

(56) References Cited

OTHER PUBLICATIONS tor, CD134, and CD137 in series with signals from tire TCR zeta chain", J Immunol. Jan. 1, 2004; 172(1):104-113.
Finney et al., "Chimeric receptors providing both primary and costimulatory signaling in T cells from a single gene product," J Immunol. Sep. 15, 1998;161(6):2791-2797.
Foon et al., "Clinical and immune responses in advanced melanoma patients immunized with an anti-idiotype antibody mimicking disialoganglioside GD2," J Clin Oncol., 18(2):376-384, Jan. 2000.
Freshney, Animal Cell Culture, Cancer Research Campaign, IRL Press, 1986, 248 pages [Table of Contents Only].
Fujisaki, H. et al., "Expansion of highly cytotoxic human natural killer cells for cancer cell therapy," Cancer Res., 69(9): 4010-4017 (2009).
Fujisaki, H. et al., "Replicative potential of human natural killer cells," Br J Haematol,145: 606-613 (2009).
Galustian, C. et al., "MP84-07A Tale of Tails—A Novel Approach to Immunotherapy of Prostate Cancer," J Urol, 195(4S): e1092 (May 2016).
Gardner, R., et al., "Acquisition of a CD19 negative myeloid phenotype allows immune escape of MLL-rearranged B-ALL from CD19 CAR-T cell therapy," Blood (forthcoming 2016).
Garrity et al., "Tire activating NKG2D receptor assembles in the membrane with two signaling dimers into a hexameric structure," PNAS, vol. 102, No. 21, pp. 7641-7646, May 24, 2005.
Geiger and Jyothi, "Development and application for receptor-modified T lymphocytes for adoptive immunotherapy," Transfus Med Rev, Jan. 2001, 15(1): 21-34.
Geiger et al., "Integrated src kinase and costimulatory activity enhances signal transduction through single-chain chimeric receptors in T lymphocytes", Blood. Oct. 15, 2001; 98(8):2364-2371.
GenBank Accession No. NM 007360 GI:15221123, *Homo sapiens* killer cell lectin like receptor K1 (KLRK1), mRNA, dated May 29, 2017, 4 pages.
GenBank Accession No. NM_000734 GI: 37595563, *Homo sapiens* CD3Z antigen, zeta polypeptide (TiT3 complex) (CD3Z), transcript variant 2, mRNA, dated Oct. 27, 2004, 6 pages.
GenBank Accession No. NM_001768 GI: 27886640, *Homo sapiens* CD8 antigen, alpha polypeptide (p32) (CD8A), transcript variant 1, mRNA, dated Oct. 27, 2004, 5 pages.
GenBank Accession No. NM_011612 GI: 6755830, Mus musculus tumor necrosis factor receptor superfamily, member 9 (Tnfrsf9), mRNA, dated Oct. 26, 2004, 8 pages.
Germain et al., "T-cell signaling: the importance of receptor clustering," Curr Biol., 7(10):R640-R644, Oct. 1, 1997.
Ghobadi, et al., "Updated Phase 1 Results from ZUMA-1: A Phase 1-2 Multicenter StudyEvaluating the Safety and Efficacy of KTE-C19 (Anti-CD19 CAR T Cells) in Subjects With Refractory Aggressive Non-Hodgkin Lymphoma," Slides accompanying oral presentation at the American Association for Cancer Research Annual Meeting, New Orleans, Louisiana (2016).
Ghorashian, S., et al., "CD19 chimeric antigen receptor T cell therapy for haematological malignancies," Br. J. Haematol. 169:463-478 (2015).
Giebel, S. et al., "Survival advantage with KIR ligand incompatibility in hematopoietic stem cell transplantation from unrelated donors," *Blood*, 102(3): 814-819 (2003).
Gilfillan et al., "NKG2D recruits two distinct adapters to trigger NK cell activation and costimulation," Nature Publishing Group, Nature Immunology, vol. 3, No. 12, pp. 1150-1155, Dec. 2002.
Gill, S., et al., "Chimeric antigen receptor T cell therapy: 25 years in the making," Blood Rev. (2015).
Ginaldi, L., et al., "Levels of expression of CD19 and CD20 in chronic B cell leukaemias," J. Clin. Pathol. 51:364-369 (1998).
Giuliani, M. et al., "Generation of a novel regulatory NK cell subset from peripheral blood CD34+ progenitors promoted by membrane-bound IL-15," PLos One, 3(5): e2241 (2008).
Gong et al., "Cancer Patient T Cells Genetically Targeted to Prostate-Specific Membrane Antigen Specifically Lyse Prostate Cancer Cells and Release Cytokines in Response to Prostate-Specific Membrane Antigen," Neoplasia, 1999, 1(2): 123-127.
Goodier and Londei, "CD28 is not directly involved in the response of human CD3-CD56+ natural killer cells to lipopolysaccharide: a role for T cells," Immunology, Apr. 2004, 111(4): 384-90.
Goodwin et al., "Molecular cloning of a ligand for the inducible T cell gene 4-1 BB: a member of an emerging family of cytokines with homology to tumor necrosis factor", Eur J Immunol. Oct. 1993; 23 ( 10):2631-2641.
Grauer et al., "Identification, Purification, and Subcellular Localization of Prostate-specific Membrane Antigen PSM' Protein in the LNCaP Prostatic Carcinoma Cell Line," Cancer Res., 58: 4787-4789 (1998).
Greene et al., "Covalent dimerization of CD28/CTLA-4 and oligomerization of CD80/CD86 regulate T cell costimulatory interactions," J Biol Chem., 271(43):26762-26771, Oct. 25, 1996.
Greenfield, E.A., et al., "CD28/B7 Costimulation: A Review," Crit. Rev. Immunol. 18: 389-418 (1998).
Greenwald et al., "The B7 Family Revisited," Annu. Rev. Immunol., 2005, 23: 515-548.
Grillo-López, A., "Rituximab: An Insider's Historical Perspective," Seminars in Oncology 27(6 Suppl 12): 9-16 (2012).
Gross and Eshhar, "Endowing T cells with antibody specificity using chimeric T cell receptors," FASEB J. Dec. 1992;6(15):3370-3378.
Grupp et al., "Chimeric antigen receptor-modified T cells for acute Ivmphoid leukemia," N Engl J Med. Apr. 18, 2013; 368 (16): 1509-1518.
Handgretinger, R., et al., "A phase I study of neuroblastoma with the anti-ganglioside GD2 antibody 14.G2a," Cancer Immunol. Immunother. 35: 199-204 (1992).
Hara et al., "NKG2D gene polymorphisms are associated with disease control of chronic myeloid leukemia bv dasatinib," Int. J. Hematol., 9 pages, Aug. 9, 2017.
Harada H, et al., "Selective expansion of human natural killer cells from peripheral blood mononuclear cells by the cell line, HFWT", Jpn J Cancer Res. Mar. 2002; 93(3):313-319.
Harada H, et al.; "A Wilms tumor cell line, HFWT, can greatly stimulate proliferation of CD56+ human natural killer cells and their novel precursors in blood mononuclear cells", Exp Hematol. Jul. 2004; 32(7):614-621.
Harding et al., "CD28-mediated signalling co-stimulates murine T cells and prevents induction of anergy in T-cell clones," Nature, 356(6370):607-609, Apr. 16, 1992.
Hannon et al., "Dexamethasone induces irreversible G1 arrest and death of a human lymphoid cell line," J Cell Physiol, Feb. 1979, 98(2): 267-78.
Haynes NM, et al., "Rejection of syngeneic colon carcinoma by CTLs expressing single-chain antibody receptors codelivering CD28 costimulation", J Immunol., Nov. 15, 2002; 169(10):5780-5786.
Haynes NM, et al., "Single-chain antigen recognition receptors that costimulate potent rejection of established experimental tumors", Blood, Nov. 1, 2002; 100(9):3155-3163.
Haynes. N.M., et al., "Redirecting Mouse CTL Against Colon Carcinoma: Superior Signaling Efficacy of Single-Chain Variable Domain Chimeras Containing TCR-ζ vs FcεRI-γ," J. Immunol. 166: 182-187 (2001).
Heuser, C., et al., "T-cell activation by recombinant immunoreceptors: Impact of the intracellular signalling domain on the stability of receptor expression and antigen-specific activation of grafted T cells," Gene Therapy 10: 1408-1419 (2003).
Hoffmann, S.C. et al. "2B4 Engagement Mediates Rapid LFA-1 and Actin-Dependent NK Cell Adhesion to Tumor Cells as Measured by Single Cell Force Spectroscopy," J. Immunol, 186(5): 2757-2764 (Jan. 2011).
Hollyman, D., et al., "Manufacturing Validation of Biologically Functional T Cells Targeted to CD19 Antigen for Autologous Adoptive T cell Therapy," J. Immunother. 32: 169-180 (2009).
Hombach , et al., "Tumor-specific T cell activation by recombinant immunoreceptors: CD3 zeta signaling and CD28 costimulation are simultaneously required for efficient IL-2 secretion and can be integrated into one combined CD28/CD3 zeta signaling receptor molecule", J Immunol., Dec. 1, 2001; 167(11 ):6123-6131.

(56) References Cited

OTHER PUBLICATIONS

Hombach et al., "T-Cell Activation by Recombinant Receptors: CD28 Costimulation Is Required for Interleukin 2 Secretion and Receptor-mediated T-Cell Proliferation but Does Not Affect Receptor-mediated Target Cell Lysis," Cancer Res., 2001, 61:1976-1982.
Hombach et al., "The recombinant T cell receptor strategy: insights into structure and function of recombinant immunoreceptors on the way towards an optimal receptor design for cellular immunotherapy," Curr Gene Ther. 2002 2(2):211-226.
Hombach, A., et al., "Adoptive immunotherapy with genetically engineered T cells: modification of the IgG1 Fc 'spacer' domain in the extracellular moietv of chimeric antigen receptors avoids 'off-target' activation and unintended initiation of an innate immune response," Gene Therapy 17: 1206-1213 (2010).
Hombach, A., et al., "T cell activation by recombinant FcεRI γ-chain immune receptors: an extracellular spacer domain impairs antigendependent T cell activation but not antigen recognition," Gene Therapy 7: 1067-1075 (2000).
Horng et al., "NKG2D signaling is coupled to the interleukin 15 receptor signaling pathway," Nature Immunology, vol. 8, No. 12, pp. 1345-1352, Dec. 2007.
Hsu, C. et al., "Cytokine-independent growth and clonal expansion of a primary human CD8+ T-cell clone following retroviral transduction with the IL-15 gene," *Blood*, 109(12): 5168-5177 (2007).
Hsu, K.C. et al., "Improved outcome in HLA-identical sibling hematopoietic stem-cell transplantation for acute myelogenous leukemia predicted by KIR and HLA genotypes," Blood, 105(12): 4878-4884 (2005).
Huang Q.S. et al., "Expansion of human natural killer cells ex vivo," Chine J Cell Mol Immunol, Dec. 31, 2008, vol. 24, No. 12, pp. 1167-1170.
Hurtado et al., "Potential role of 4-1BB in T cell activation. Comparison with the costimulatory molecule CD28," J Immunol, Oct. 1995, 155(7): 3360-3367.
Imai C et al. "Genetic modification of primary natural killer cells overcomes inhibitory signals and induces specific killing of leukemic cells," Blood. 2005;106:376-383.
Imai C, et al., "Chimeric receptors with 4-1BB signaling capacity provoke potent cytotoxicity against acute lymphoblastic leukemia", Leukemia., Feb. 12, 2004; 18(4):676-684.
Imai C, et al., "T-cell immunotherapy for B-lineage acute lymphoblastic leukemia using chimeric antigen receptors that deliver 4-1 BB-mediated costimulatory signals", Blood. Nov. 16, 2003; 102(11 ):66a-67a. (Abstract #223).
Imai et al. "Genetic Modification of T cells for cancer therapy," Journal of Biological Regulators and Homeostatic Agents, 18 (1): p. 62-71; Jan. 2004.
Imai, C., et al; "A novel method for propagating primary natural killer (NK) cells allows highly Efficient expression of anti-CD19 chimeric receptors and generation of powerful cytotoxicity Against NK-rcsistcnt acute lymphoblastic leukemia cells." Abstract# 306 Blood 104 (Nov. 16, 2004).
Imamura, M. et al., "Autonomous growth and increased cytotoxicity of natural killer cells expressing membrane-bound interleukin-15," *Blood*, 124(7): 1081-1088 (Jul. 8, 2014).
Inaguma et al., "Expression of neural cell adhesion molecule L1 (CD171) in neuroectodermal and other tumors. An immunohistochemical study of 5155 tumors and critical evaluation of CD171 prognostic value in gastrointestinal stromal tumors," Oncotargc., 7(34):55276-55289, Jul. 11, 2016.
Intellectual Property Office of Singapore, Search Report and Written Opinion dated May 11, 2016 for Application No. 11201505858V, 8 pages.
International Preliminary Report on Patentability for Int'l Application No. PCT/SG2015/050111, titled "Modified Natural Killer Cells and Uses Thereof," dated Nov. 15, 2016.
International Preliminary Report on Patentability dated Jul. 28, 2015 for International Application No. PCT/US2014/013292, entitled "A Chimeric Receptor With NKG2D Specificity for Use in Cell Therapy Against Cancer and Infectious Disease".

International Search Report and Written Opinion for International Application No. PCT/SG2015/050111, titled "Modified Natural Killer Cells and Uses Thereof," dated Aug. 17, 2015.
International Search Report and Written Opinion dated Apr. 28, 2014 for International Application No. PCT/US2014/013292, entitled "A Chimeric Receptor With NKG2D Specificity for Use in Cell Therapy Against Cancer and Infectious Disease".
Ishii, H. et al., "Monocytes enhance cell proliferation and LMP1 expression of nasal natural killer/T-cell lymphoma cells by cell contact-dependent interaction through membrane-bound IL-15," International Journal of Cancer, 130: 48-58 (2012).
Ishiwata I, et al., "Carcinoembryonic proteins produced by Wilms' tumor cells in vitro and in vivo", Exp Pathol. 1991; 41(1):1-9.
Israeli, R.S., et al., "Expression of the Prostate-specific Membrane Antigen," Cancer Res., 1994, 54:1807-1811.
Ito et al., "Hyperdiploid acute lymphoblastic leukemia with 51 to 65 chromosomes: a distinct biological entity with a marked propensity to undergo apoptosis," Blood, Jan. 1999, 93(1): 315-20.
Jena et al., "Redirecting T-cell specificity by introducing a tumor-specific chimeric antigen receptor," Blood, 2010, 116(7): 1035-1044.
Jenkins et al., "Inhibition of antigen-specific proliferation of type 1 murine T cell clones after stimulation with immobilized anti-CD3 monoclonal antibody," J Immunol., 144(1):16-22, Jan. 1, 1990.
Jensen, M., et al., "CD20 is a molecular target for scFvFc:ζ receptor redirected T cells: implications for cellular immunotherapy of CD20+ malignancy," Biol. Blood and Marrow Transplantation 4: 75- 83 (1998).
Jensen, M.C., et al., "Anti-transgene Rejection Responses Contribute to Attenuated Persistence of Adoptively Transferred CD20/CD19-Specific Chimeric Antigen Receptor Redirected T Cells in Humans," Biol. Blood Marrow Transplant 16: 1245-1256 (2010).
Jiang et al., "Functional characterization of interleukin-15 gene transduction into the human natural killer cell line N KL," Cytother. 10(3):265-274, 2008.
Jiang, W. et al., "hIL-15 gene-modified human natural killer cells (NKL-IL15) augments the antihuman hepatocellular carcinoma effect in vivo," Immunobiology, 219: 547-553 (Mar. 12, 2014).
Johnson and Jenkins, "Tire role of anergy in peripheral T cell unresponsiveness," Life Sci, 1994, 55(23): 1767-1780.
June et al., "The B7 and CD28 receptor families," Immunol Today, Jul. 1994, 15(7): 321-31.
Kabalak et al., "Association of an NKG2D gene variant with systemic lupus erythematosus in two populations," Human Immunology, vol. 71, pp. 74-78, 2010.
Kaiser, B.K. et al., "Structural basis for NKG2A/CD94 Recognition of HLA-E," Proc Nat'l Acad Sci USA, 105(18): 6696-6701 (Apr. 2008).
Kalos et al, "T Cells with Chimeric Antigen Receptors Have Potent Antitumor Effects and Can Establish Memory in Patients with Advanced Leukemia," Sci Transl Med. Aug. 10, 2011;3(95):95ra73.
Kariv, I., et al., "Analysis of the Site of Interaction of CD28 with Its Countcr-Rcccptors CD80 and CD86 and Correlation with Function," J. of Immunol. 157: 29-38 (1996).
Kershaw, M.H., et al., "A Phase I Study on Adoptive Immunotherapy Using Gene-Modified T Cells for Ovarian Cancer," Clin. Cancer Res. 12:6106-6115 (2006).
Khammari, A., et al., "Long-term follow-up of patients treated by adoptive transfer of melanoma tumor-infiltrating lymphocytes as adjuvant therapv for stage III melanoma," Cancer Immunol. Immunother. 56: 1853-1860 (2007).
Kim Y J, et al., "Human 4-1 BB regulates CD28 co-stimulation to promote Th1 cell responses. Eur J. Immunol", Mar. 1998; 28(3):881-890.
Kim Y J, et al., "Novel T cell antigen 4-1 BB associates with the protein tyrosine kinase p56lck1", J Immunol.Aug. 1, 1993; 151(3):1255-1262.
Kitaya, K. et al., "IL-15 expression at human endometrium and decidua," Biology of Reproduction, 63(3): 683-687 (2000).
Kitaya, K., et al., "Regulatory role of membrane-bound form interleukin-15 on human uterine micro vascular endothelial cells in circulating CD16(-) natural killer cell extravasation into human endometrium," Biology of Reproduction, 89(3): 70 (2013).

(56) References Cited

OTHER PUBLICATIONS

Kite Pharma Inc.'s Reply to Patent Owner's Response to the Petition re: IPR2015-01719, 35 pages, Aug. 4, 2016.
Klein E, et al., "Properties of the K562 cell line, derived from a patient with chronic myeloid leukemia", Int J Cancer. Oct. 15, 1976; 18(4):421-431.
Klingemann HG, et al., "Ex vivo expansion of natural killer cells for clinical applications", Cytotherapy. 2004; 6(1):15-22.
Kobayashi et al., "Role of trans-cellular IL-15 presentation in the activation of NK cell-mediated killing, which leads to enhanced tumor immunosurveillance," Blood, Jan. 2005, 105(2): 721-727.
Kochenderfer, J.N. et al. "Construction and Pre-clinical Evaluation of an Anti-CD19 Chimeric Antigen Receptor," J. Immunother. 32(7):689-702 (2009).
Kochenderfer, J.N., et al. "Chemotherapy-Refractory Diffuse Large B-Cell Lymphoma and Indolent B-Cell Malignancies Can be Effectively Treated With Autologous T Cells Expressing an Anti-CD19 Chimeric Antigen Receptor," J. Clin. Oncol. 33:540-549 (2014).
Kochenderfer, J.N., et al. "Donor-derived CD19-targeted T cells cause regression of malignancy persisting after allogeneic hematopoietic stem cell transplantation," Blood 122(25): 4129-4139 (2013).
Kochenderfer, J.N., et al., "B-cell depletion and remissions of malignancy along with cytokine-associated toxicity in a clinical trial of anti-CD19 chimeric-antigen-receptor-transduced T cells," Blood 119(12):2709-2720 (2012).
Kochenderfer, J.N., et al., "Eradication of B-lineage cells and regression of lymphoma in a patient treated with autologous T cells genetically-engineered to recognize CD19," Blood 116(20):4099-4102 (2010).
Koeffler and Golde, "Acute myelogenous leukemia: a human cell line responsive to colony-stimulating activity," Science, Jun. 1978, 200(4337): 1153-1154.
Koehler et al. "Engineered T Cells for the Adoptive Therapy of B-Cell Chronic Lymphocytic Leukaemia," Advances in Hematology, vol. 2012, Article ID 595060, 13 pages; doi: 10.1155/2012/595060 (2012).
Kohn et al., "CARs on track in the clinic," Mol Ther. Mar. 2011; 19(3):432-438.
Koka, R. et al., "Cutting edge: murine dendritic cells require IL-15R alpha to prime NK cells," *J Immunol.*, 173(6): 3594-3598 (2004).
Kolb HJ, et al., "Graft-Versus-Leukemia Effect of Donor Lymphocyte Transfusions in Marrow Grafted Patients," Blood, 1995, 86(5):2041-2050.
Kowolik, C.M., "CD28 Costimulation Provided through a CD19-Specific Chimeric Antigen Receptor Enhances In vivo Persistence and Antitumor Efficacy of Adoptively Transferred T Cells," Cancer Research 66(22): 10995-11004 (2006).
Krampera et al., "Bone marrow mesenchymal stem cells inhibit the respnose of naïve and memory antigen-specific T cells to their cognate peptide," Blood, May 2003, 101(9): 3722-9.
Krause et al., "Antigen-dependent CD28 Signaling Selectively Enhances Survival and Proliferation in Genetically Modified Activated Human Primary T Lymphocytes," J. Exp. Med., 1998, 188(4):619-626.
Krug, C., et al., "Stability and activity of MCSP-specific chimeric antigen receptors (CARs) depend on the scFv antigen-binding domain and the protein backbone," Cancer Immunol. Immunother. 64:1623- 1635 (2015).
Kuo et al., "Efficient gene transfer into primary murine lymphocytes obviating the need for drug selection," Blood, Aug. 1993, 82(3): 845-52.
Kurokawa, M. and S. Kornbluth, "Caspases and kinases in a death grip," *Cell*, 138(5): 838-854 (2009).
Kwon BS, et al., "cDNA sequences of two inducible T-cell genes", Proc Natl Acad Sci U SA. Mar. 1989, 86(6):1963-1967.
LaBonte, M.L. et al., "Molecular Determinants Regulating the Pairing of NKG2 Molecules with CD94 for Cell Surface Heterodimer Expression," J Immunol, 172(11): 6902-6912 (May 2004).

Lafreniere, R. and Rosenberg, S.A., "Successful Immunotherapy of Murine Experimental Hepatic Metastases with Lymphokine-activated Killer Cells and Recombinant Interleukin 2," Cancer Res. 45: 3735-3741 (1985).
Lamers, C.H.J., et al., "Treatment of Metastatic Renal Cell Carcinoma With Autologous T-Lymphocytes Genetically Retargeted Against Carbonic Anhydrase IX: First Clinical Experience," J. Clin. Oncol. 24: e20-e22 (2006).
Lang et al., "Absence of B7.1-CD28/CTLA-4-mediated co-stimulation in human NK cells," Eur. J. Immunol, Mar. 1998, 28: 780-786.
Langer et al., "Comparative Evaluation of Peripheral Blood T Cells and Resultant Engineered Anti-CD19 CAR T-Cell Products From Patients With Relapsed/Refractory Non-Hodgkin Lymphoma (NHL)," Abstract 2305, Proceedings: AACR 107th Annual Meeting 2016; Apr. 16-20, 2016, New Orleans, Louisiana.
Lanzavecchia et al., "Antigen decoding by T lymphocytes: from synapses to fate determination," Nat Immunol., 2(6):487-492, Jun. 2001.
Lapteva, N. et al., "Large-scale ex vivo expansion and characterization of natural killer cells for clinical applications," *Cytotherapy*, 14(9): 1131-1143 (2012).
Le Blanc et al., "Mesenchymal stem cells inhibit and stimulate mixed lymphocyte cultures and mitogenic responses independently of the major histocompatibility complex," Scand J Immunol, Jan. 2003, 57(1): 11-20.
Lee, D.W., et al., "T cells expressing CD19 chimeric antigen receptors for acute lymphoblastic leukaemia in children and young adults: a phase 1 dose-escalation trial," Lancet 385:517-528 (2015).
Lehner et al., "Redirecting T Cells to Ewing's Sarcoma Family of Tumors by a Chimeric NKG2D Receptor Expressed by Lentiviral Transduction of MRNA Transfection," PLoS One, vol. 7, Issue 2, Feb. 2012.
Leung, W. et al., "Determinants of antileukemia effects of allogeneic NK cells," J Immunol., 172(1): 644-650 (2004).
Li et al., "Costimulation by CD48 and B7-1 induces immunity against poorly immunogenic tumors," J Exp Med, Feb. 1996, 183(2): 639-44.
Li et al., "Polarization Effects of 4-1BB during CD28 Costimulation in Generating Tumor-reactive T Cells for Cancer Immunotherapy," Cancer Research vol. 63, pp. 2546-2552, May 15, 2003.
Li, Q. et al., "Bifacial effects of engineering tumour cell-derived exosomes on human natural killer cells" Experimental Cell Research, Dec. 19, 2017, vol. 363, No. 2, pp. 141-150.
Liao, W. et al., "Interleukin-2 at the crossroads of effector responses, tolerance, and immunotherapy," Immunity, 38(1): 13-25 (2013).
Licbowitz et al., "Costimulatory approaches to adoptive immunotherapy," Curr Opin Oncol, Nov. 1998, 10(6): 533-41.
Linsley and Ledbetter, "The role of CD28 receptor during T cell responses to antigen," Annu Rev Immunol, 1993, 191-212.
Liu, H., et al., "Monoclonal Antibodies to the Extracellular Domain of Prostate-specific Membrane Antigen Also React with Tumor Vascular Endothelium," Cancer Res. 57: 3629-3634 (1997).
Liu, L, et al. "Novel CD4-Based Bispecific Chimeric Antigen Receptor Designed for Enhanced Anti-HIV Potency and Absence of HIV Entry Receptor Activity," J. Virol. 89(13):6685-6694 (2015).
Lode et al., "Targeted cytokines for cancer immunotherapy," Immunol Res., 21(2-3):279-288, 2000.
López-Requena et al., "Gangliosides, Ab1 and Ab2 antibodies III. The idiotype of anti-ganglioside mAb P3 is immunogenic in a T cell-dependent manner," Mol Immunol., 2007, 44(11):2915-2922.
López-Requena et al., "Gangliosides, Ab1 and Ab2 antibodies IV. Dominance of VH domain in the induction of anti-idiotypic antibodies by Jene gun immunization," Mol Immunol. Apr. 2007;44(11):3070-3075. Epub Mar. 2, 2007.
Lozzio CB, et al., "Human chronic myelogenous leukemia cell-line with positive Philadelphia chromosome", Blood. Mar. 1975; 45(3):321-334.
Lozzio et al., "Properties and Usefulness of the Original K-562 Human Myelogenous Leukemia Cell Line," Leukemia Research, vol. 3, No. 6, pp. 363-370, 1979.

(56) References Cited

OTHER PUBLICATIONS

Lugli, E. et al., "Transient and persistent effects of IL-15 on lymphocyte homeostasis in nonhuman primates," Blood, 116(17): 3238-3248 (2010).
Ma et al., "Chapter 15: Genetically engineered T cells as adoptive immunotherapy of cancer," Cancer Chemotherapy and Biological Response Modifiers Annual 20, Ch. 15, pp. 315-341, Giaccone et al. (Eds.), Elsevier, 2002.
Maher J., et al., "Human T-lymphocyte cytotoxicity and proliferation directed by a single chimeric TCRzeta /CD28 receptor", Nat Biotechnol. Jan. 2002; 20(1):70-75.
Maloney, D.G., "Newer Treatments for Non-Hodgkin's Lymphoma: Monoclonal Antibodies," Oncology 12(10): 63-76 (1998).
Manabe et al., "Interleukin-4 induces programmed cell death (apoptosis) in cases of high-risk acute lymphoblastic leukemia," Blood, Apr. 1994, 83(7): 1731-7.
Mann et al., "Construction of a retrovirus packaging mutant and its use to produce helper-free defective retrovirus," Cell, May 1983, 33(1): 153-159.
Manzke et al., "Immunotherapeutic strategies in neuroblastoma: antitumoral activity of deglycosylated Ricin A conjugated anti-GD2 antibodies and anti-CD3xanti-GD2 bispecific antibodies," Med Pediatr Oncol., 36(1): 185-189, Jan. 2001.
Manzke et al., "Locoregional treatment of low-grade B-cell lvmphoma with CD3xCD19 bispecific antibodies and CD28 costimulation. I. Clinical phase I evaluation," Int J Cancer., 91(4):508-515, Feb. 15, 2001.
Manzke et al., "Locoregional treatment of low-grade B-cell lymphoma with CD3xCD19 bispecific antibodies and CD28 costimulation. II. Assessment of cellular immune responses," Int J Cancer., 91(4):516-522, Feb. 15, 2001.
Marincola, F.M., et al., "Escape of Human Solid Tumors from T-Cell Recognition: Molecular Mechanisms and Functional Significance," Adv. Immunol. 74: 181-273 (2000).
Markowitz et al., "A safe packaging line for gene transfer: separating viral genes on two different plasmids," J Virol, Apr. 1988, 62(4): 1120-4.
Marktel et al., "Immunologic potential of donor lymphocytes expressing a suicide gene for early immune reconstitution after hematopoietic T-cell-depleted stem cell transplantation," Blood, Feb. 2003, 101(4): 1290-8.
Martinet O., et al., T cell activation with systemic agonistic antibody versus local 4-1 BB ligand gene delivery combined with interleukin-12 eradicate liver metastases of breast cancer, Gene Ther. Jun. 2002; 9(12):786-792.
Martinez, E., et al., "Cutting Edge: NKG2D-Dependent Cytotoxicity Is Controlled by Ligand Distribution in the Target Cell Membrane", The Journal ofImmunology, 2011, 186:5538-5542.
Maude et al., "Chimeric antigen receptor T cells for sustained remissions in leukemia," N Engl J Med., 371(16): 1507-1517, Oct. 16, 2014.
Maus MV, et al., "Ex vivo expansion of polyclonal and antigen-specific cytotoxic T lymphocytes by artificial APCs expressing ligands for the T-cell receptor, CD28 and 4-1BB", Nat Biotechnol. Feb. 2002; 20(2): 143-148.
May KF, JR, et al., "Anti-4-1 BB monoclonal antibody enhances rejection of large tumor burden by promoting survival but not clonal expansion of tumor-specific CDS+ T cells," Cancer Res. 2002, 62(12):3459-3465.
McLaughlin et al., "Adoptive T-cell therapies for refractory/relapsed leukemia and lymphoma: current strategies and recent advances," Ther Adv Hematol., 6(6):295-307, Dec. 2015.
Melero I, et al., "Amplification of tumor immunity by gene transfer of the co-stimulatory 4-1 BB ligand: synergy with the CD2S co-stimulatory pathway," Eur J Immunol., 1998, 28(3):1116-1121.
Melero I, et al., "NK1.1 cells express 4-1BB (CDw137) costimulatory molecule and are required for tumor immunity elicited by anti-4-1 BB monoclonal antibodies," Cell Immunol., 1998, 190(2): 167-172.

Melero, I. et al, "Monoclonal antibodies against the 4-1BB T-cell activation molecule eradicate established tumors," Nature Med., 1997, 3:682-685.
Memorandum Consolidating the Actions in Trustees of the *University of Pennsylvania v. St. Jude Children's Research Hospital* in the US District Court for the Eastern District of Pennsylvania, dated Nov. 13, 2013.
Mihara et al., "Development and functional characterization of human bone marrow mesenchymal cells immortalized by enforced expression of telomerase," Br J Haematol, Mar. 2003, 120(5): 846-9.
Miller et al., "Role of monocytes in the expansion of human activated natural killer cells," Blood, Nov. 1992, 80(9): 2221-9.
Miller et al., "Successful adoptive transfer and in vivo expansion of human haploidentical NK cells in patients with cancer," Blood, Apr. 2005, 105(8): 3051-7.
Miller, J.S., "Therapeutic applications: natural killer cells in the clinic," *Hematology Am Soc Hematol Educ Program* 2013: 247-253 (2013).
Milone MC, et al., "Chimeric receptors containing CD137 signal transduction domains mediate enhanced survival of T cells and increased anti leukemic efficacy in vivo", Mol Ther. Apr. 21, 2009; 17(8):1453-1464.
Minamoto, S. et al., "Acquired Erythropoietin Responsiveness of Interleukin-2-dependent T lymphocytes Retrovirally Transduced with Genes Encoding Chimeric Erythropoietin/Interleukin-2 Receptors," Blood, vol. 86, No. 6, pp. 2281-2287 (1995).
Mishra, A. et al., "Aberrant overexpression of IL-15 initiates large granular lymphocyte leukemia through chromosomal instability and DNA hypermethylation," *Cancer Cell*, 22(5): 645-655 (2012).
Mogi et al., "Tumour rejection by gene transfer of 4-1BB ligand and into a CD80(+) murine squamous cell carcinoma and the requirements of co-stimulatory molecules on tumour and host cells," Immunology, Dec. 2000, 101(4): 541-7.
Mohammed, S. et al., "Improving Chimeric Antigen Receptor-Modified T Cell Function by Reversing the Immunosuppressive Tumor Microenvironment of Pancreatic Cancer," Mol. Ther. 4, vol. 25, No. 1, pp. 249-258 (2017).
Mondino and Jenkins, "Surface proteins involved in T cell costimulation," J Leukoc Biol, Jun. 1994, 55(6): 805-15.
Mora, "Dinutuximab for the treatment of pediatric patients with high-risk neuroblastoma," Expert Rev Clin Pharmacol., 9(5):647-653, Epub Mar. 21, 2016.
Morandi, B. et al., "NK cells provide helper signal for CD8+ T cells by inducing the expression of membrane-bound IL-15 on DCs," International Immunology, 21(5): 599-606 (2009).
Moretta L, et al., "Unravelling natural killer cell function: triggering and inhibitory human NK receptors," EMBO J., 2004, 23(2):255-259.
Moritz and Groner, "A spacer region between the single chain antibody- and the CD3 ζ-chain domain of chimeric T cell receptor components is required for efficient ligand binding and signaling activity," Gene Ther. Oct. 1995; 2(8):539-546.
Moritz, D., et al., "Cytotoxic T lymphocytes with a grafted recognition specificity for ERBB2-expressing tumor cells," Proc. Natl. Acad. Sci. USA 91:4318-4322 (1994).
Mortier, E., et al., "IL-15Ralpha chaperones IL-15 to stable dendritic cell membrane complexes that activate NK cells via trans presentation," *The Journal of Experimental Medicine*, 205(5): 1213-1225 (2008).
Musso, T. et al., "Human monocytes constitutively express membrane-bound, biologically active, and interferon-gamma-upregulated interleukin-15," *Blood*, 93(10): 3531-3539 (1999).
Nadler et al., "B4, a human B lymphocyte-associated antigen expressed on normal, mitogen-activated, and malignant B lymphocytes," J Immunol, Jul. 1983, 131(1): 244-50.
Nagashima et al., "Stable transduction of the interleukin-2 gene into human natural killer cell lines and their phenotypic and functional characterization in vitro and in vivo," Blood, May 1998, 91(10): 3850-61.
Nakamura et al., "Chimeric anti-ganglioside GM2 antibody with antitumor activity," Cancer Res. Mar. 15, 1994, 54(6):1511-6.

(56) References Cited

OTHER PUBLICATIONS

Naume et al., "A comparative study of IL-12 (cytotoxic lymphocyte maturation factor)-, IL-2-, and IL-7-induced effects on immunomagnetically purified CD56+ NK cells," J Immunol, Apr. 1992, 148(8): 2429-36.

Neepalu et al., "Phase 1 Biomarker Analysis of the ZUMA-1 Study: A Phase 1-2 Multi-Center Study Evaluating the Safety and Efficacy of Anti-CD19 CAR T Cells (KTE-C19) in Subjects with Refractory Aggressive Non-Hodgkin Lymphoma," Poster session presented at the American Scoiety of Hematology Annual Meeting, Orlando, Florida (Dec. 5-8, 2015).

Negrini, S. et al., "Membrane-bound IL-15 stimulation of peripheral blood natural killer progenitors leads to the generation of an adherent subset co-expressing dendritic cells and natural killer functional markers," *Haematologica*, 96(5): 762-766 (2011).

Nicholson et al., "Construction and characterisation of a functional CD19 specific single chain Fv fragment for immunotherapy of B lineage leukaemia and lymphoma," Mol Immunol., 34(16-17):1157-1165, Nov.-Dec. 1997.

Nishigaki et al., "Prevalence and growth characteristics of malignant stem cells in B-lineage acute lymphoblastic leukemia," Blood, May 1997, 89(10): 3735-44.

Nunès et al., "The role of p21ras in CD28 signal transduction: triggering of CD28 with antibodies, but not the ligand B7-1, activates p21ras," J Exp Med., 180(3): 1067-1076, Sep. 1, 1994.

Oelke, M. et al., "Ex vivo induction and expansion of antigen-specific cytotoxic T cells by HLA-Ig-coated artificial antigen-presenting cells," Nat Med., 2003, 9(5):619-624.

Olsen, S.K. et al., "Crystal structure of the interleukin-15 interleukin-15 receptor α complex Insights into trans and cis presentation," The Journal of Biological Chemistry, 282(51): 37191-37204 (2007).

Ozkaynak, M.F. et al., "Phase I Study of Chimeric Human/Murine Anti-Ganglioside GD2 Monoclonal Antibody (ch14.18) With Granulocyte-Macrophage Colony-Stimulating Factor in Children With Nueroblastoma Immediately After Hematopoietic Stem-Cell Transplantation: A Children's Cancer Group Study," J. Clinical Oncol. 18: 4077-4085 (2000).

Pan et al., "Regulation of dendritic cell function by NK cells: mechanisms underlying the synergism in the combination therapy of IL-12 and 4-1BB activation," J Immunol, Apr. 2004, 172(8): 4779-4789.

Park, J.H., and Brentjens, R.J., "Are All Chimenc Antigen Receptors Created Equal?" J. Clin. Oncol. 33:651-653 (2015).

Park, J.H., et al., "CD19-Targeted 19-28z CAR Modified Autologous T Cells Induce High Rates of Complete Remission and Durable Responses in Adult Patients with Relapsed, Refractory B-Cell ALL," Abstract presented at the American Society of Hematology Annual Meeting, San Francisco, California, available at https://ash.confex.com/ash/2014/webprogram/Paper76573.html (Dec. 6-9, 2014).

Park, J.H., et al., Abstract, "682 Implications of Minimal Residual Disease Negative Complete Remission (MRD-CR) and Allogeneic Stem Cell Transplant on Safety and Clinical Outcome of CD19-Targeted 19-28z CAR Modified T cells in Adult Patients with Relapsed, Refractory B-Cell ALL," Am. Soc'y Hematol., available at https://ash.confex.com/ash/2015/webprogram/Paper86688.html (Dec. 5-8, 2015).

Park, Y.P., et al., "Complex Regulation of Human NKG2D-DAP10 Cell Surface Expression: Opposing Roles of the γc Cytokines and TGF-β1", Blood, Sep. 15, 2011, vol. 118, No. 11, pp. 3019-3027.

Parkhurst, M.R. et al., "Adoptive transfer of autologous natural killer cells leads to high levels of circulating natural killer cells but does not mediate tumor regression," Clin Cancer Res., 17(19): 6287-97(2011).

Patel, S.D., et al., "Impact of chimeric immune receptor extracellular protein domains on T cell function," Gene Therapy 6: 412-419 (1999).

Paul, W.E., Fundamental Immunology, Third Edition. Chs. 1, 13 and 32 (pp. 1-20, 467-504, and 1143-1178), Raven Press, New York (1993).

Peach, R.J., et al., "Complementarity Determining Region 1 (CDR1)- and CDR3-analogous Regions in CTLA-4 and CD28 Determine the Binding to B7-1," J. Exp Med. 180: 2049-2058 (1994).

Perussia et al., "Preferential proliferation of natural killer cells among peripheral blood mononuclear cells cocultured with B lymphoblastoid cell lines," Nat Immun Cell Growth Regul, 1987, 6(4): 171-88.

Pollok et al., "Regulation of 4-1BB expression by cell-cell interactions and the cytokines, interleukin-2 and interleukin-4," Eur J Immunol, Feb. 1995, 25(2): 488-94.

Pollok KE, et al., "Inducible T cell antigen 4-1 BB Analysis of expression and function," J Immunol., 1993, 150(3):771-781.

Porter and Antin, "The graft-versus-leukemia of allogeneic cell therapy," Annu Rev Med, 1999, 50: 369-86.

Porter DL et al., "Chimeric Antigen Receptor-Modified T Cells in Chronic Lymphoid Leukemia", N. Eng. J. Med. Aug. 25, 2011; 365(8):725-733.

Porter et al., "Induction of graft-versus-host disease as immunotherapy for relapsed chronic myeloid leukemia," N Engl J Med, Jan. 1994, 330(2): 100-6.

Pui et al., "Childhood acute lymphoblastic leukaemia—current status and future perspectives," Lancet Oncol, Oct. 2001, 2(10): 597-607.

Pule et al. "Virus-specific T cells engineered to coexpress tumor-specific receptors: persistence and antitumor activity in individuals with neuroblastoma," Nature Med., 2008, 14(11):1264-1270.

Qi L. et al., "Multiple effects of IL-21 on the ex vivo expansion of human primary NK cells," Immunology, Nov. 28, 2014, vol. 143, No. S2, p. 62-176, Poster Abstract 708.

Qian, L. et al., "Construction of a plasmid for co-expression of mouse membrane-bound form of IL-15 and RAE-1ε and its biological activity," *Plasmid*, 65(3): 239-245 (2011).

Rajagopalan et al., Found: a cellular activating ligand for N Kp44, Blood, 122(17):2921-2922, Oct. 2013.

Ramos and Dotti, "Chimeric antigen receptor (CAR)-engineered lymphoevtes for cancer therapy," Expert Opin Biol Ther., 2011, 11(7):855-873.

Ramos, C.A., et al., "CD19-CAR Trials," The Cancer J. 20: 112-118 (2014).

Riddell, S.R., et al., "T-Cell Therapy of Leukemia," Cancer Control 9: 114-122 (2002).

Riley et al., "The CD28 family: a T-cell rheostat for therapeutic control of T-cell activation," Blood, 2005, 105:13-21.

Roberts et al., "Antigen-specific cytolysis by neutrophils and NK cells expressing chimeric immune receptors bearing zeta or gamma signaling domains," J Immunol, Jul. 1998, 161(1): 375-84.

Robertson MJ, et al.; "Costimulation of human natural killer cell proliferation: role of accessory cytokines and cell contact-dependent signals", Nat Immun. 1996-1997; 15(5):213-226.

Rooney et al., "Use of gene-modified virus-specific T lymphocytes to control Epstein-Barr-virus-related lymphoproliferation," Lancet, Jan. 1995, 345(8941): 9-13.

Rosenberg et al, "Special Report: Use of tumor-infiltrating lymphocytes and interleukin-2 in the immunotherapy of patients with metastatic melanoma," N. Engl. J. Med., 1988, 319:1676-1680.

Rosenberg, S.A., and Dudley, M.E., "Adoptive cell therapy for the treatment of patients with metastatic melanoma," Curr. Opin. Immunol. 21: 233-240 (2009).

Rosenfeld et al., "Phenotypic charactenzation of a unique non-T, non-B acute lymphoblastic leukaemia cell line," Nature, Jun. 1977, 267(5614): 843-3.

Rosenstein, M. et al., "Extravasation of intravascular fluid mediated by the systemic administration of recombinant interleukin 2," *J Immunol*, 137(5): 1735-1742 (1986).

Ross et al., "Classification of pediatric acute lymphoblastic leukemia by gene expression profiling," Blood, Oct. 2003, 102(8): 2951-9.

Rossi, J.M., et al., "Phase 1 Biomarker Analysis of ZUMA-1 (KTEC19-101) Study: A Phase 1-2 Multi-Center Study Evaluating the Safety and Efficacy of Anti-CD19 CAR T cells (KTE-C19) in Subjects with Refractory Aggressive Non-Hodgkin Lymphoma (NHL)," Abstracted presented at the American Society of Hematology Annual

(56) References Cited

OTHER PUBLICATIONS

Meeting, Orlando, Florida, available at https://ash.confex.com/ash/2015/webprogram/Paper80339.html. (Dec. 5-8, 2015).
Rossig C, et al., "Epstein-Barr virus-specific human T lymphocytes expressing antitumor chimeric T-cell receptors: potential for improved immunotherapy," Blood, 2002, 99:2009-2016.
Rossig et al., "Targeting of G(D2)-positive tumor cells by human T lymphocytes engineered to express chimeric T-cell receptor genes," Int J Cancer, Oct. 2001, 94(2): 228-36.
Rowley, J. et al., "Expression of IL-15RA or an IL-15/IL-15RA fusion on CD8+ T cells modifies adoptively transferred T-cell function in cis," A European Journal ofImmunology, 39: 491-506 (2009).
Rubnitz, J.E. et al., "NKAML: a pilot study to determine the safety and feasibility of haploidentical natural killer cell transplantation in childhood acute mveloid leukemia," J Clin Oncol, 28(6): 955-959 (2010).
Ruggeri, L. et al., "Effectiveness of donor natural killer cell alloreactivity in mismatched hematopoietic transplants," Science, 295(5562): 2097-2100 (2002).
Sadelain et al., "The promise and potential pitfalls of chimeric antigen receptors," Curr Opin Immunol., 2009, 21(2):215-223.
Sadelain et al., "Targeting tumours with geneticallv enhanced T lymphocytes," Nat Rev Cancer. Jan. 2003;3(1):35-45.
Sadelain, M., "CAR Therapy: the CD19 Paradigm," J. Clin. Investigation 125: 3392-3400 (2015).
Sahm et al., "Expression of IL-15 in N K cells results in rapid enrichment and selective cytotoxicity of gene-modified effectors that carry a tumor-specific antigen receptor," Cancer Immunol. Immunother., 61 (9): 1451-1461, Feb. 2012.
Salih, H.R., et al., "Cutting Edge: Down-Regulation of MICA on Human Tumors by Proteolytic Shedding", The Journal of Immunology, 2002, 169:4098-4102.
Salomon and Bluestone, "Complexities of CD28/B7: CTLA-4 costimulatory pathways in autoimmunity and transplantation," Annu Rev Immunol, 2001, 19: 225-52.
Sambrook et al., "Molecular Cloning: A Laboratory Manual," (1989) [Table of Contents and Preface Only].
Sankhla, S.K., et al., "Adoptive immunotherapy using lymphokineactivated killer (LAK) cells and interleukin-2 for recurrent malignant primary brain tumors," J Neurooncol. 27: 133-140 (1995).
Santegoets S.J. et al., "IL-21 promotes the expansion of CD27+ CD28+ tumor infiltrating lymphocytes with high cytotoxic potential and low collateral expansion of regulatory T cells," Journal of Translational Medicine, Feb. 12, 2013, vol. 11, No. 37, pp. e1-e10.
Savoldo, B., et al., "CD28 costimulation improves expansion and persistence of chimeric antigen receptor modified T cells in lymphoma patients," J. Clin. Invest. 121(5): 1822-1826 (2011).
Schmaltz et al., "T cells require TRAIL for optimal graft-versus-tumor activity," Nat Med, Dec. 2002, 8(12): 1433-7.
Schneider et al., "Characterization of EBV-genome negative "null" and "T" cell lines derived from children with acute lymphoblastic leukemia and leukemic transfonned non-Hodgkin lymphoma," Int J Cancer, May 1977, 19(5): 621-6.
Schroers et al., "Gene transfer into human T lymphocytes and natural killer cells by Ad5/F35 chimeric adenoviral vectors," Exp Hematol, Jun. 2004, 32(6): 536-46.
Schulz, G., et al., "Detection of Ganglioside GD2 in Tumor Tissues and Sera of Neuroblastoma Patients," Cancer Research 44: 5914-5920 (1984).
Schumacher, "T-cell-receptor gene therapy," Nat Rev Immunol, Jul. 2002, 2(7): 512-9.
Schwartz et al., "Structural basis for co-stimulation by the human CTLA-4/B7-2 complex," Nature, 410(6828):604-608, Mar. 29, 2001.
Schwarz et al., "ILA, the human 4-1BB homologue, is inducible in lymphoid and other cell lineages," Blood, Feb. 7, 1995, 85(4): 1043-52.
Scott, A.M. et al., "Antibody therapy of cancer," *Nat Rev Cancer*, 12(4): 278-287 (2012).

Search Report dated Apr. 27, 2016 and Written Opinion dated Nov. 5, 2016 of Singapore Application No. 11201505858V (11 pages).
Sentman, C.L., et al., "NK Cell Receptors as Tools in Cancer Immunotherapy", Advances in Cancer Research, 2006, pp. 249-292.
Sentman, C.L., et al., "NKG2D CARs as Cell Therapy for Cancer", The Cancer Journal, vol. 20, No. 2, Mar./Apr. 2014, pp. 156-159.
Sheard, M.A. et al., "Membrane-bound TRAIL supplements natural killer cell cytotoxicity against neuroblastoma cells," Journal of Immunotherapy, 36(5): 319-329 (2013).
Shimasaki, N. et al., "A clinically adaptable method to enhance the cytotoxicity of natural killer cells against B-cell malignancies," Cvtotherapy, 14(7): 830-840 (2012).
Shook et al., "Natural Killer Cell Engineering for Cellular Therapy of Cancer." National Institutes of Health, Tissue Antigens, vol. 78, No. 6, pp. 409-415, Dec. 2011.
Shuford WW, et al., "4-1 BB costimulatory signals preferentially induce CDS+ T cell proliferation and lead to tire amplification in vivo of cytotoxic T cell responses", J Exp Med. Jul. 7, 1997; 186(1):47-55.
Shum et al., "Conservation and Variation in Human and Common Chimpanzee CD($ and NKG2 Genes," The American Association of Immunologists, The Journal of Immunology, pp. 240-252, Downloaded on Jun. 18, 2017.
Sica G, Chen L. Modulation of the immune response through 4-1BB. In: Habib N, ed. Cancer gene therapy: past achievements and future challenges. New York: Kluwer Academic/Plenum Publishers; 355-362 (2000) [BOOK].
Slavik et al., "CD28/CTLA-4 and CD80/CD86 families: signaling and function," Immunol Res., 19(1):1-24, 1999.
Slavin et al., "Allogeneic cell therapy with donor penpheral blood cells and recombinant human interleukin-2 to treat leukemia relapse after allogeneic bone marrow transplantation," Blood, Mar. 1996, 87(6): 2195-204.
Sloan Kettering Institute for Cancer Research's Patent Owner Preliminary Response re: IPR2015-01719, 68 pages, dated Nov. 25, 2015.
Sloan Kettering Institute for Cancer Research's Patent Owner Response re: IPR2015-01719, 86 pages, dated May 5, 2016.
Sneller, M.C. et al., "IL-15 administered bv continuous infusion to rhesus macaques induces massive expansion of CD8+ T effector memory population in peripheral blood," Blood, 118(26): 6845-6848 (2011).
Somanchi, S.S. et al., "Expansion, purification, and functional assessment of human peripheral blood NK cells," Journal of Visualized Experiments, 48A: 2540 (2011).
Song et al., "Chimeric NKG2D CAR-Expressing T Cell-Mediated Attack of Human Ovarian Cancer is Enhanced by Histone Deacetylase Inhibition," Human Gene Therapy, vol. 24, pp. 295-305, Mar. 2013.
Spear et al., "Chimeric Antigen Receptor T Cells Shape Myeloid Cell Function within the Tumor Microenvironment through IFN-γ and GM-CSF," The Journal of Immunology, pp. 6389-6399, 2014.
Spear et al., "Collaboration of chimeric antigen receptor (CAR)-expressing T cells and host T cells for optimal elimination of established ovarian tumors," OncoImmunology, vol. 2, No. 2, 12 pages, Apr. 2013.
Spear et al., "NKG2D CAR T-cell therapy inhibits the growth of NKG2D ligand heterogeneous tumors," Immunology and Cell Biology, vol. 91, pp. 435-440, 2013.
Srinivasan et al., "A retro-inverso peptide mimic of CD28 encompassing the MYPPPY motif adopts a polyproline type II helix and inhibits encephalitogenic T cells in vitro," J Immunol., 167(1):578-585, Jul. 1, 2001.
Srivannaboon et al., "Interleukin-4 variant (BAY 36-1677) selectively induces apoptosis in acute lymphoblastic leukemia cells," Blood, Feb. 2001, 97(3): 752-8.
Stamper et al., "Crystal structure of the B7-1/CTLA-4 complex that inhibits human immune responses," Nature, 410(6828):608-611, Mar. 29, 2001.
Steel et al., "Interleukin-15 biology and its therapeutic implications in cancer," Trends Pharmacol. Sci. 33(1) :35-41, Jan. 2012.
Stein, P.H., et al., "The Cytoplasmic Domain of CD28 is both Necessary' and Sufficient for Costimulation of Interleukin-2 Secre-

(56) References Cited

OTHER PUBLICATIONS tion and Association with Phosphatidylinositol 3'-Kinase," Mol. Cell. Biol. 14: 3392-3402 (1994).
Stong RC, et al., "Human acute leukemia cell line with the t(4;11) chromosomal rearrangement exhibits B lineage and monocytic characteristics," Blood, 1985,65:21-31.
Sullivan, L.C. et al., "The Heterodimeric Assembly of the CD94-NKG2 Receptor Family and Implications for Human Leukocyte Antigen-E Recognition," Immunity, 27(6): 900-911 (Dec. 2007).
Sun. J., et al., "Early transduction produces highly functional chimeric antigen receptor-modified virus-specific T-cells with central memory markers: a Production Assistant for Cell Therapy (PACT) translational application," J. Immunother. Cancer (2015).
Sundstrom and Nilsson, "Establishment and characterization of a human histiocytic lymphoma cell line (U-937)," Int J Cancer, May 1976, 17(5): 565-77.
Sussman et al., "Protein Data Bank (PDB): database of three-dimensional structural information of biological macromolecules," Acta Crystallogr D Biol Crystallogr., 54(Pt 6 Pt 1):1078-1084, Nov. 1, 1998.
Swerdlow, S.H. et al., eds., "WHO Classification of Tumours of Haematopoietic and Lymphoid Tissues," International Agency for Research on Cancer (IARC) (4th ed. 2008) (Excerpts).
Tacke et al., "CD28-mediated induction of proliferation in resting T cells in vitro and in vivo without engagement of the T cell receptor: evidence for functionally distinct forms of CD28," Eur J Immunol., 27(1):239-247, Jan. 1997.
Tagaya, Y. et al., "IL-15: a pleiotropic cytokine with diverse receptor/signaling pathways whose expression is controlled at multiple levels," Immunity, 4(4): 329-336 (1996).
Takahashi C, et al., "Cutting edge: 4-1 BB is a bona fide CDS T cell survival signal", J Immunol. May 1, 1999; 162(9):5037-5040.
Thomas et al., "Monoclonal antibody therapy with rituximab for acute lymphoblastic leukemia," Hematol Oncol Clin North Am., 23(5):949-971, Oct. 2009.
Topp, M.S., et al., "Universal chimeric immunoreceptors for targeting B-cell malignancies with engineered CTL: combining CD19-specific TCR zeta signaling with engineered CD28-mediated co-stimulation," Mol. Ther. 3(5)(part2 of 2): S21 (2001).
Trinchieri et al., "Response of resting human peripheral blood natural killer cells to interleukin 2," J Exp Med, Oct. 1984, 160(4): 1147-69.
Trompeter et al., "Rapid and highly efficient gene transfer into natural killer cells by nucelofection," J Immunol Methods, Mar. 2003, 274(1-2): 245-56.
Tsukamoto, K. et al., "Juxtacrine function of interleukin-15/interleukin-15 receptor system in tumour derived human B-cell lines," Clinical and Experimental Immunology, 146(3): 559-566 (2006).
Turtle, "Therapy of B Cell Malignancies with CD19-Specific Chimeric Antigen Receptor Modified T Cells of Defined Subset Composition," Blood 124(21): 384-384, 2014.
Turtle, C.J., et al., Abstract, "A Phase I/II Clinical Trial of Immunotherapy for CD19+ B Cell Malignancies With Defined Composition of CD4+ and CD8+ Central Memory T Cells Lentivirally Engineered To Express a CD19-Specific Chimeric Antigen Receptor" Mol. Ther., 2014, 22(Supp.1):296.
Upshaw et al., "NKG2D-mediated signaling requires a DAP10-bound Grb2-Vav! intermediate and hosphatidylinositol-3-kinase in human natural killer cells," Nature Immunology, vol. 7, No. 5, pp. 524-532, May 2006.
Verdonck et al., "Donor leukocyte infusions for recurrent hematologic malignancies after allogeneic bone marrow transplantation: impact of infused and residual donor T cells," Bone Marrow Transplant, Dec. 1998, 22(11): 1057-63.
Verma and Stock, "Management of adult acute lymphoblastic leukemia: moving toward a risk-adapted approach," Curr Opin Oncol, Jan. 2001, 13(1): 14-20.
Vinay, DS et al., "Role of 4-1 BB in immune responses", Seminars in Immunol. Dec. 1998: 10(6):481-489.
Viola, "The amplification of TCR signaling by dynamic membrane microdomains," Trends Immunol., 22(6):322-327, Jun. 2001.
Vivier, E. et al., "Innate or adaptive immunity? The example of natural killer cells," Science, 331(6013): 44-49 (2011).
Voss et al., "Targeting p53, hdm2, and CD19: vaccination and immunologic strategies," Bone Marrow Transplant., 25 Suppl 2:S43-S45, May 2000.
Vujanovic, L. et al., "Virally infected and matured human dendritic cells activate natural killer cells via cooperative activity of plasma membrane-bound TNF and IL-15," Blood, 116(4): 575-583 (2010).
Waldmann, T.A. et al., "Safety (toxicity), pharmacokinetics, immunogenicity, and impact on elements of the normal immune system of recombinant human IL-15 in rhesus macaques," Blood, 117(18): 4787-4795 (2011).
Walter et al., "Reconstitution of cellular immunity against cytomegalovirus in recipients of allogeneic bone marrow by transfer of T-cell clones from the donor," N Engl J Med, Oct. 1995, 333(16): 1038-44.
Wang, et al., "Phase I Studies of central-memory-derived CD19 CAR T cell therapy following autologous HSCT in patients with B-Cell NHL," Blood (forthcoming 2016).
Warrens AN, et al., "Splicing by overlap extension by PCR using asymmetric amplification: an improved technique for the generation of hybrid proteins of immunological interest," Gene 20;186: 29-35 (1997).
Watzl, C., et al., "Signal Transduction During Activation and Inhibition of Natural Killer Cells", Curr Protoc Immunol., Aug. 2010, pp. 1-19.
Weijtens, M.E.M., et al., "Functional balance between T cell chimeric receptor density and tumor associated antigen density: CTL mediated cytolysis and lymphokine production," Gene Ther. 7: 35-42 (2000).
Weissman et al., "Molecular cloning and chromosomal localization of the human T-cell receptor ~ chain: Distinction from the molecular CD3 complex," PNAS USA, 1988, 85:9709-9713.
Westwood, J.A., et al., "Adoptive transfer of T cells modified with a humanized chimeric receptor gene inhibits growth of Lewis-Y expressing tumors in mice," PNAS 102(52): 19051-19056 (2005).
WHO, "WHO Classification of Tumours of Haematopoietic and Lymphoid Tissues," International Agency for Research on Cancer (IARC), 4th Edition, 40 pages, 2008.
Wilkie, S. et al., "Selective Expansion of Chimeric Antigen Receptor-targeted T-cells with Potent Effector Function Using Interleukin-4," J Biol Chem., vol. 295, No. 33, pp. 25538-25544 (2010).
Willimsky, G. and Blankenstein, T., "Sporadic immunogenic tumours avoid destruction by inducing T-cell tolerance," Nature 437: 141-146 (2005).
Wittnebel, S. et al., "Membrane-bound interleukin (IL)-15 on renal tumor cells rescues natural killer cells from IL-2 starvation-induced apoptosis," Cancer Research, 67(12): 5594-5599 (2007).
Written Opinion dated Jun. 22, 2017 for Singapore Application No. 11201505858V (5 pages).
Wu and Lanier, "Natural killer cells and cancer," Adv Cancer Res, 2003, 90: 127-56.
Wu, et al. "An Activating Immunoreceptor Complex Formed by NKG2D and DAP10," Science, vol. 285, pp. 730-732, Jul. 30, 1999.
Wyss-Coray, T., et al., "The B7 adhesion molecule is expressed on activated human T cells: functional involvement in T-T cell interactions," Eur. J. Immunol., 23: 2175-2180 (1993).
Xu, Y., et al., "Closely related T-memory stem cells correlate with in vivo expansion of CAR.CD19-T cells and are preserved by IL-7 and IL-15," Blood 123(24):3750-3759 (2014).
Yan et al., "Murine COB lymphocyte expansion in vitro by artificial antigen-presenting cells expressing CD137L (4-1 BBL) is superior to CD28, and CD137L expressed on neuroblastoma expands COB tumour-reactive effector cells in vivo," Immunology, 2004, 112(1):105-116.
Ye et al., "Gene therapy for cancer using single-chain Fv fragments specific for 4-1BB," Nat Med, Apr. 2002, 8(4): 343-8.
Ye et al. "Effects of target cell overexpression of IL-15, 4-1 BBL and IL-18 1-102 combine with IL-2 on NK cell activation and cytotoxic-

(56) References Cited

OTHER PUBLICATIONS ity during ex vivo expansion" *Chin J Cancer Biother*, Oct. 31, 2014, vol. 21, No. 5, pp. 537-542 (Non-English, Copy Search Report for PCT/SG2018/050138 attached).

Yeoh et al., "Classification, subtype discovery, and prediction of outcome in pediatric acute lymphoblastic leukemia by gene expression profiling," Cancer Cell, Mar. 2002, 1(2): 133-43.

Yoshida et al., "A novel adenovirus expressing human 4-1BB ligand enhances antitumor immunity," Cancer Immunol Immunother, Feb. 2003, 52(2): 97-106.

Zah, E. et al., "T Cells Expressing CD19/CD20 Bispecific Chimeric Antigen Receptors Prevent Antigen Escape by Malignant B Cells," Cancer Immunol Res, 4(6): 498-508 (Apr. 2016).

Zanoni, I. et al., "IL-15 cis presentation is required for optimal NK cell activation in lipopolysaccharide-mediated inflammatory conditions," *Cell Reports*, 4: 1235-1249 (2013).

Zeis, M. et al., "Allogeneic MHC-Mismatched Activated Natural Killer Cells Administered After Bone Marrow Transplantation Provide a Strong Graft-Versus-Leukemia Effect in Mice," BrJ Haematol, 1997, pp. 757-761, vol. 96.

Zhang et al., "Chimeric NKG2D-Modified T Cells Inhibit Systemic T-Cell Lymphoma Growth in a Manner Involving Multiple Cytokines and Cytotoxic Pathways," Cancer Research, vol. 67, No. 22, pp. 11029-11036, Nov. 15, 2007.

Zhang et al., "Chimeric NK-receptor-bearing T cells mediate antitumor immunotherapv," Gene Therapy, Blood, vol. 106, No. 5, pp. 1544-1551, Sep. 2005.

Zhang et al., "Generation of Antitumor Responses by Genetic Modification of Primary Human T Cells with a Chimeric NKG2D Receptor," Cancer Research, vol. 66, No. 11, pp. 5927-5933, Jun. 1, 2006.

Zhang et al., "Mouse Tumor Vasculature Expresses NKG2D Ligands and Can Be Targeted by Chimeric NKG2D-Modified T Cells," The Journal of Immunology, pp. 2455-2463, (2013) Downloaded Feb. 20, 2018.

Zhang, J. et al., "Characterization of interleukin-15-gene-modified human natural killer cells: implications for adoptive cellular immunotherapy," Haematologica, 89(3): 338-347 (2004).

U.S. Non-Final Office Action for U.S. Appl. No. 15/309,362, entitled "Modified Natural Killer Cells And Uses Thereof," dated Jun. 18, 2018.

U.S. Final Office Action for U.S. Appl. No. 15/309,362, entitled "Modified Natural Killer Cells And Uses Thereof," dated Dec. 20, 2018.

Notice of Allowance n for U.S. Appl. No. 15/309,362, entitled "Modified Natural Killer Cells And Uses Thereof," dated May 16, 2019.

U.S. Non-Final Office Action for U.S. Appl. No. 16/550,548, entitled"Natural Killer Cells Modified To Express Membrane-Bound Interleukin 15 And Uses Thereof," dated Jan. 23, 2020.

Notice of Allowance for U.S. Appl. No. 16/550,548, entitled"Natural Killer Cells Modified To Express Membrane-Bound Interleukin 15 and Uses Thereof," dated May 13, 2020.

Gillet et al., Selectable Markers far Gene Therapy, Chapter 26 of Gene and Cell Therapy:Therapeutic Mechanisms and Strategies, 3rd Ed. N .S. Templeton Ed, (CRC Press:Bpca Ratpm. FL), pp. 555 and 558, 2009.

Sureth et al., "Efficient Generation of Gene-Modified Human Natural Kiiler Cells via Alpharetroviral Vectors," J. Mol. Med. 94:83-93, 2016, published online 25 Au. 2015.

Sokolic et al., "A Selectable Bicistronic Retroviral Vector Corrects the Molecular Defect in a Cell Line Derived from a Patient with Leukocyte Adhesion Deficiency," Biol. Blood Marrow Transpl. 12(2) Suppl 1: 20-21, Feb. 2006.

U.S. Appl. No. 60/383,872, filed May 28, 2002, to Sadelain et al.

Gacerez, A et al., "How Chimeric Antigen Receptor Design Affects Adoptive T Cell Therapy," Journal of Cellular Physiology, vol. 231, No. 12, pp. 2590-2598 (Jun. 2, 2016).

Sadelain, M. et al., "The Basic Principles of Chimeric Antigen Receptor Design," Cancer Discovery, vol. 3, No. 4, pp. 388-398 (Apr. 1, 2013).

Abken, H. et al., "Antigen-specific T-cell activation independently of the MHC: chimeric antigen receptor-redirected T cells," Frontiers in Immunology, V. 4, Article 371, c. 4 (2013).

Calabrese, et al., "IL-6 biology: implications for clinical targeting in rheumatic disease," S. Nat. Rev. Rheumatol, 10, 720-727 (2014); published online Aug. 19, 2014 (corrected online Sep. 19, 2014).

Cordoba, S.P. et al., "The large ectodomains of CD45 and CD148 regulate their segregation from and inhibition of ligated T-cell receptor," Blood, The Journal of the American Society of Hematology, V. 121, N. 21, p. 4295-4302, c. 4301 (2013).

Culpepper, D.J. et al., "Systematic mutation and thermodynamic analysis of central tyrosine pairs in polyspecific NKG2D receptor interactions," Molecular Immunology, V. 48, N. 4, p. 516-523, c. 521-522 (2011).

De Felipe, P., "Polycistronic Viral Vectors," Current Gene Therapy, V. 2, N. 3, p. 355-378, c. 360 (2002).

Lanier, Lewis L., "NK Cell Recognition," Annual Review of Immunology, vol. 23, No. 1, pp. 225-274 (2005).

Lima, et al., "Interleukin-6 Neutralization by Antibodies Immobilized at the Surface of Polymeric Nanoparticles as a Therapeutic Strategy for Arthritic Diseases," ACS Appl. Mater. Interfaces 2018, 10, 13839-13850.

Zhao, Y. et al., "A Herceptin-Based Chimeric Antigen Receptor with Modified Signaling Domains Leads to Enhanced Survival of Transduced T Lymphocytes and Antitumor Activity," The Journal of Immunology, V. 183, N. 9, p. 5563-5574, c. 5568, 5571 (2009).

Abakushina, E.V., "Immunotherapy With Natural Killer Cells In The Treatment Of Cancer," Russian Journal of Immunology, vol. 10, No. 2, pp. 131-142 (2016) (Abstract only).

Denman et al., "Membrane-Bound IL-21 Promotes Sustained Ex Vivo Proliferation of Human Natural Killer Cells," PLoS ONE, vol. 7, Issue 1, Jan. 2012.

Dowell, A. C. , "Studies of Human T cell Costimulation:Potential for the Immunotherapy of Cancer," A thesis submitted to The University of Birmingham for the degree of Doctor of Philosophy, CRUK Institute for Cancer Studies, 2010.

Hasan, A.N., "Soluble and membrane-bound interleukin (IL)-15 Ra/IL-15 complexesmediate proliferation of high-avidity central memory CD81T cells foradoptive immunotherapy of cancer and infections," Clinical and Experimental Immunology, 186: 249-265, 2016.

Leitner et al., "T cell stimulator cellsm an efficient and versatile cellular system to assess the role of costimulatory ligands in the activation of human T cells," Journal of Immunological Methods, 362, 131-141, 2010.

Oyer et al., "Natural killer cells stimulated with PM21 particles expand and biodistribute in vivo: Clinical implications for cancer treatment," Cytotherapy, 18: 653-663, 2016.

Wang et al., "Human NK cells maintain licensing status and are subject to killer immunoglobulin-like receptor (KIR) and KIR-ligand inhibition following ex vivo expansion," Cancer Immunol Immunother, 65:1047-1059, 2016.

Zhang et al., "Improving Adoptive T Cell Therapy by Targeting and Controlling IL-12 Expression to the Tumor Environment," The American Society of Gene & Cell Therapy Molecular Therapy, vol. 19, No. 4, 751-759, 2011.

Ren, P.-P. et al., Anti-EGFRvIII Chimeric Antigen Receptor-Modified T Cells for Adoptive Cell Therapy of Glioblastoma, Current Pharmaceutical Design, 23(14), 2113-2116 (2017).

Morgan, R.A. et al., Recognition of Glioma Stem Cells by Genetically Modified T Cells Targeting EGFRvIII and Development of Adoptive Cell Therapy for Glioma, Human Gene Therapy, 23(10), 1043-1053 (2012).

Dalal, A.-R. et al., Third-Generation Human Epidermal Growth Factor Receptor 2 Chimeric Antigen Receptor Expression on Human T Cells Improves with Two-Signal Activation, Human Gene Therapy, 845-852 (2018) (Abstract).

(56) References Cited

OTHER PUBLICATIONS

Choi, B. D. et al., Chimeric antigen receptor T-cell immunotherapy for glioblastoma: practical insights for neurosurgeons, Neurosurg Focus, 44(6):E13, 1-6 (2018).

* cited by examiner

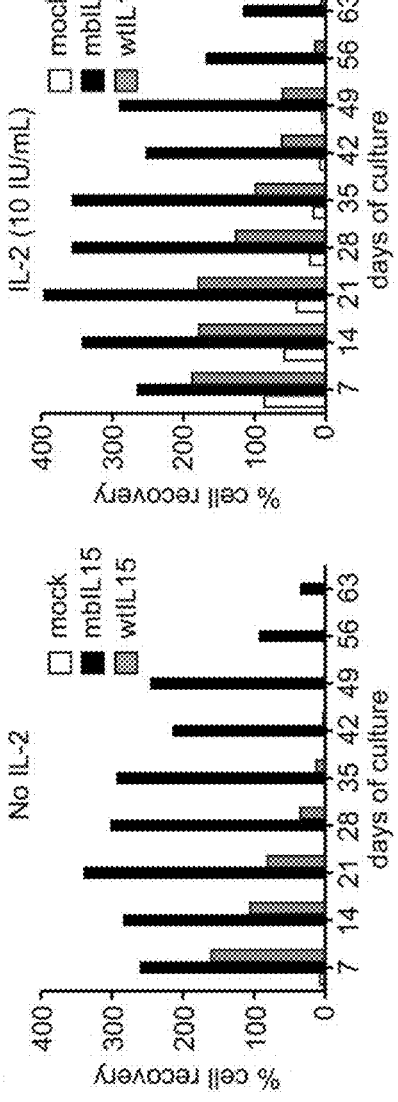
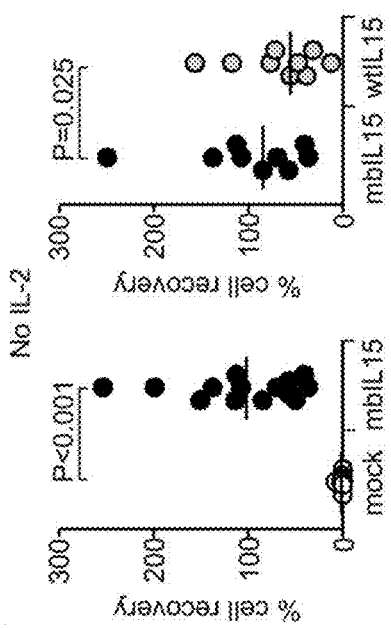
FIG. 2A
FIG 2B
FIG. 2C

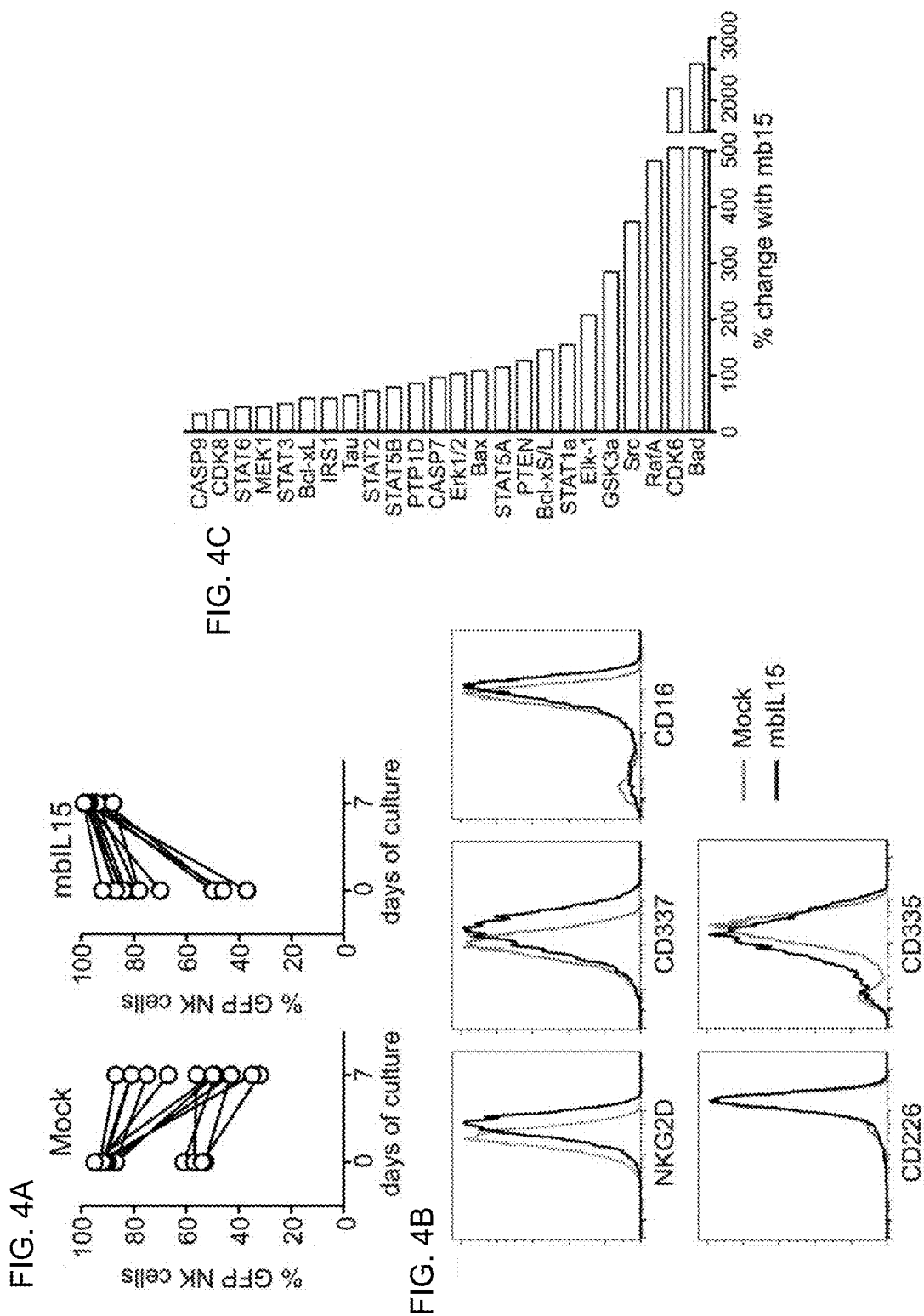

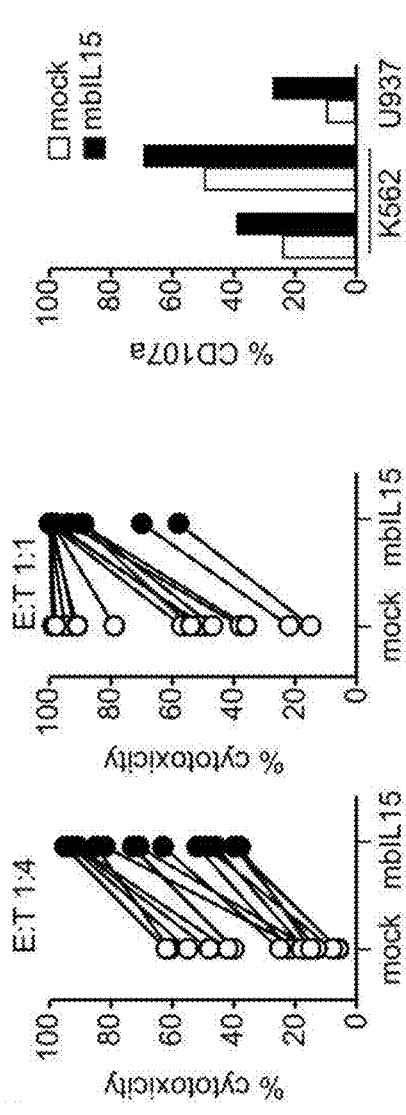
FIG. 5A
FIG. 5B
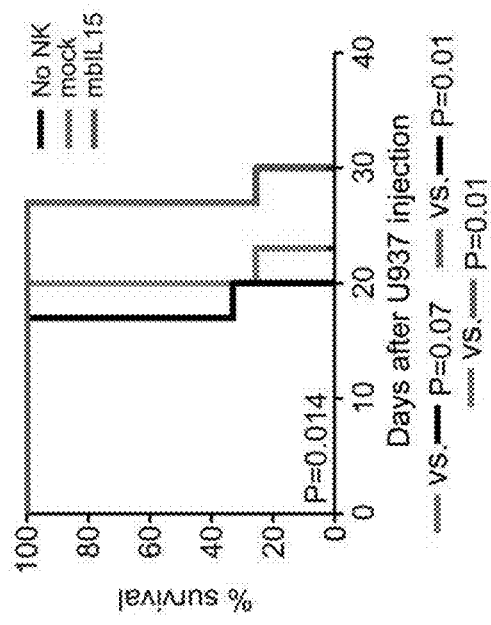
FIG. 5D
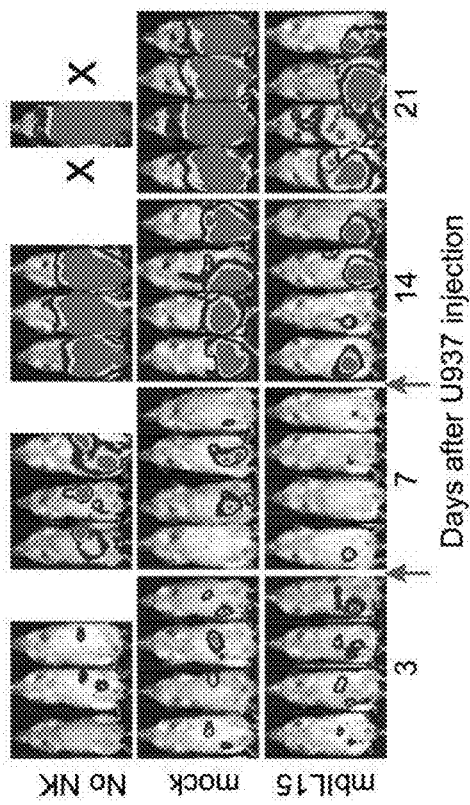
FIG. 5C

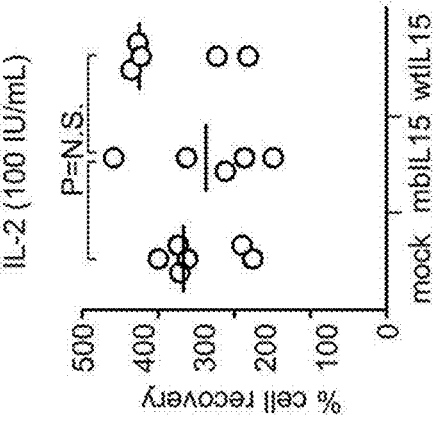
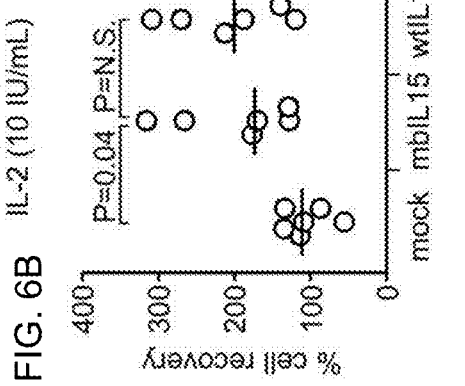
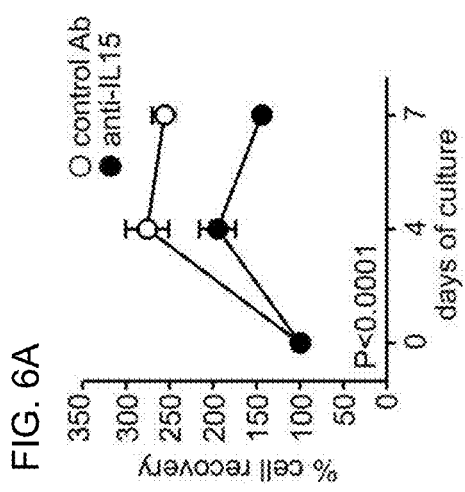
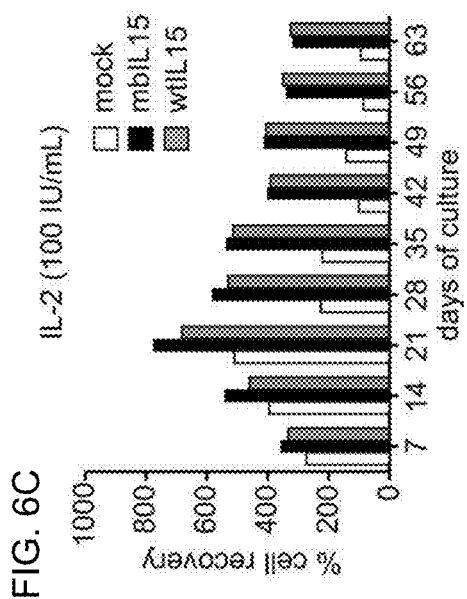

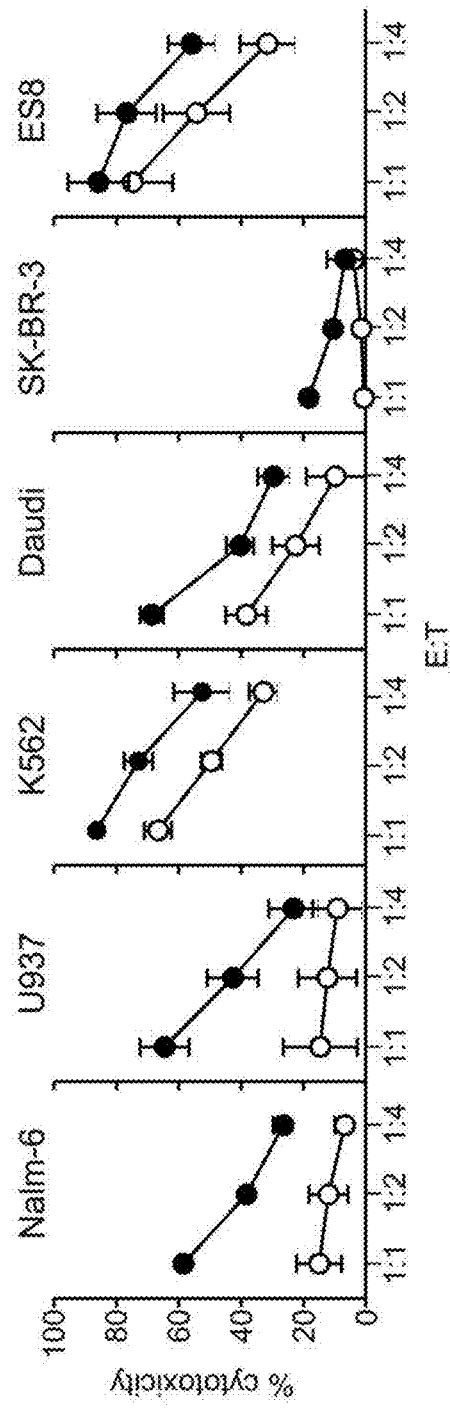
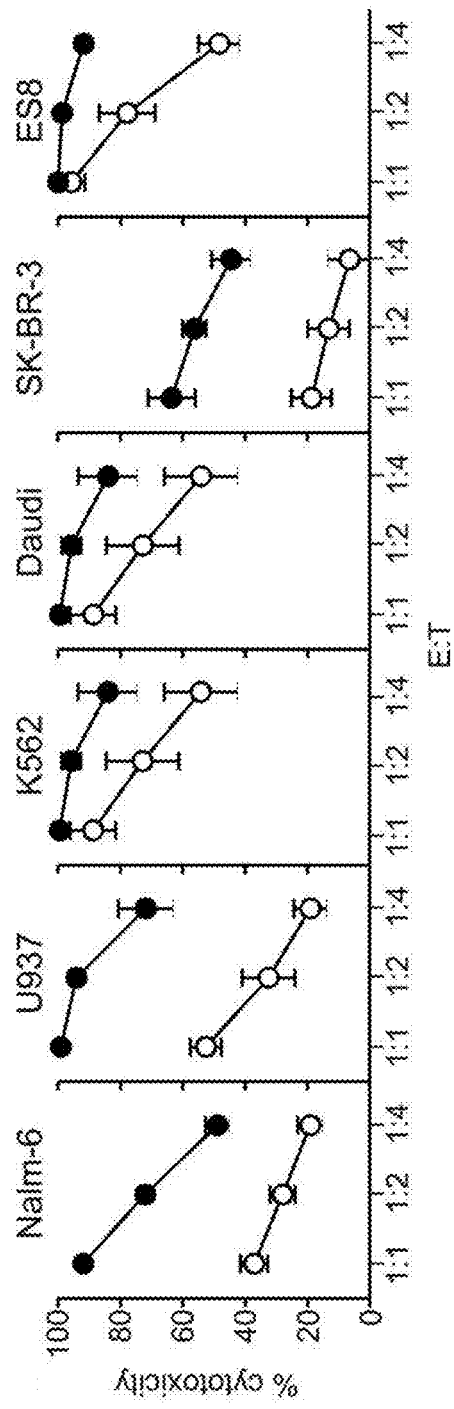
FIG. 7A
FIG. 7B

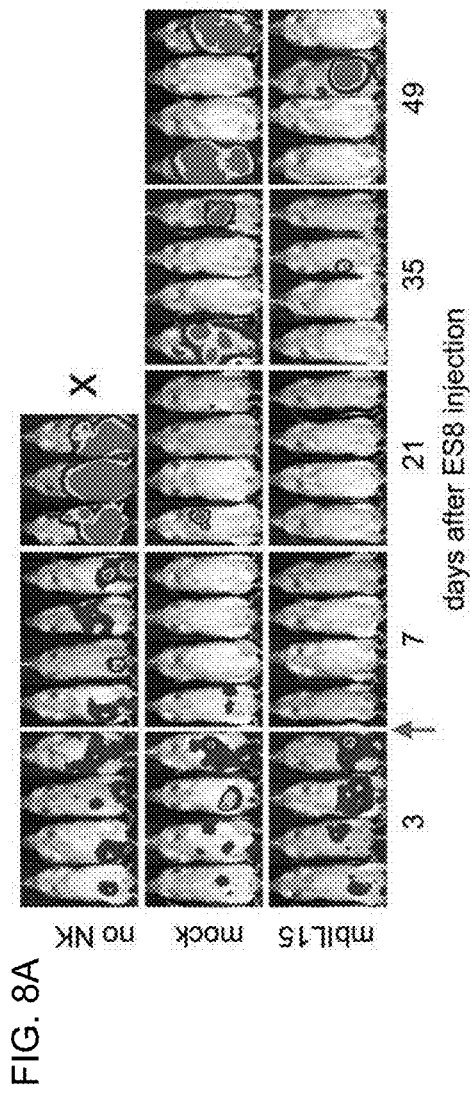
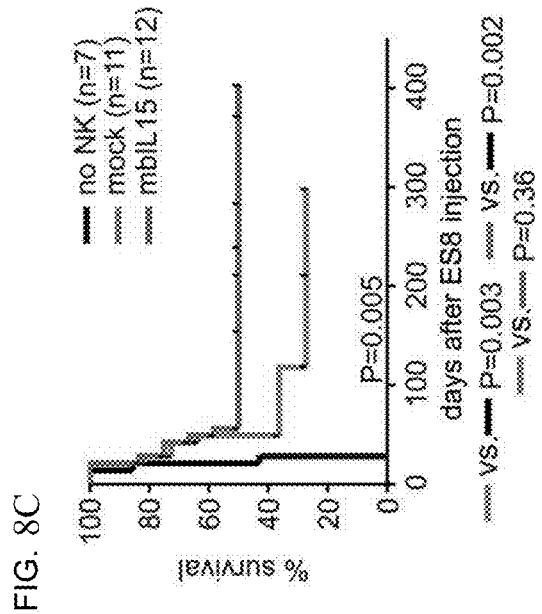
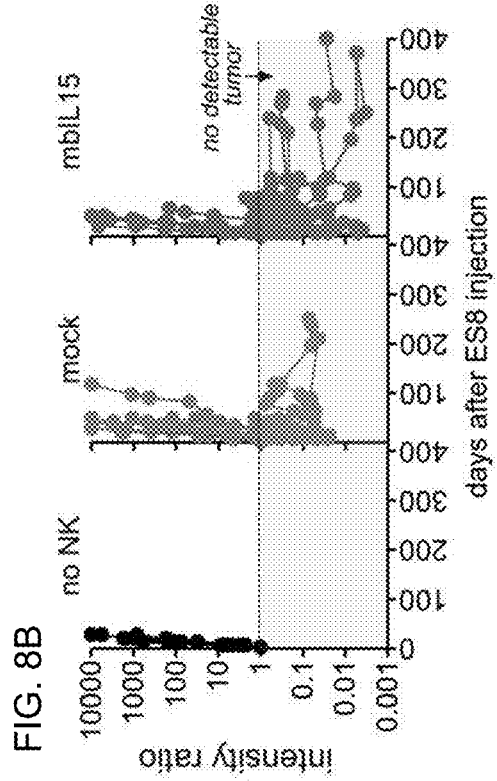
FIG. 8A
FIG. 8B
FIG. 8C

FIG. 9

Sequence of membrane bound IL15

Nucleotide

EcoR1-Kozak-CD8aSP-IL15-CD8ahingeTM-XhoI (638 bp)

GAATTCGCCCTTCCACCATGGCCCTTACCAGTGACCGCCTGCTCCTGCTGCTCCACGCCGCCAGGC
CGAACTGGGTGAATGTAATAAGTGATTTGAAAAAAATTGAAGATCTATTCAATCTATGCATATTTATA
TACGGAAAGTGATGTGTTCACCCCAGTTGCAAAGTAACAGCAATGAAGTGCTTTCTCTTGGAGTTACAAGTTATTTCACTT
GAGTCCGGAGAGATGCAAGTATTCATGATACAGTATTCATCCTAGCAAACAACAGTTTGTCTTCTAATGGG
AATGTAACACAGAATCTGGATGCAAAGAATGTGAGGAACTGAGGAAAAAATATTAAAGAATTTTTGCAGAGTTTGTA
CATATTGTCCAAATGTTCATCAACACTTCTACCACGAGCCAGCGGGGGGGCCCATCGCG
TCGCAGCCCCTGTCCCTGCGCCCGGAGGCCTGCCGCCCAGTGCAGGTCACGAGGGGCTGGAC
TTCGCCTGTGATATCTACATCTGGGCGCCCCTTGGCCGGACTTGTGGGGTCCTCTCGTCACTGTTATCACCCTT
ACTGCTAACTCGAG

Amino Acid

CD8aSP-IL15-CD8ahingeTM (204 aa)

MALPVTALLLPLALLLHAARPNWVNVISDLKKIEDLIQSMHIDATLYTESDVHPSCKVTAMKCFLLELQVISLESGDASIHDTVE
NLIILANNSLSSNGNVTESGCKECEELEEKNIKEFLQSFVHIVQMFINTS*TTTPAPRPPTPAPTIASQPLSLRPEACRPAAGGA
VHTRGLDFACDIYIWAPLAGTGVLLLSLVITLYC*

FIG. 10 Homo sapiens interleukin 15 (IL15), transcript variant 3, mRNA

Nucleotide

IL15 Signal Peptide- *Proprotein*- Mature peptide (489 bp)

ATGAGAATTTCGAAACCACATTTGAGAAGTATTTCCATCCAGTGCTACTTGTGTTTACTTCTAAACAGTCATTTCTAACTGAAGCT*G*
*GCATTCATGTCTTCATTTTGGGCTGTGTTCAGTGCAGGGCTTCCTAAAACAGAAGCC*AACTGGGTGAATGTAATAAGTGATTTGAAA
AAATTGAAGATCTATTCAATCTATATGCATATTGATGCTACTTTATATACGGAAAGTGATGTTCACCCAGTTGCAAAGTAACAGCAAT
GAAGTGCTTTCTCTTGGAGTTACAAGTTATTTCACTTGAGTCCGGAGATGCAAGTATTCATGATACAGTAGAAAATCTGATCATCCTA
GCAAACAACAGTTTGTCTTCTAATGGGAATGTAACAGAATCTGGATGCAAAGAATGTGAGGAACTGGAGGAAAAAATATTAAAGAA
TTTTTGCAGAGTTTTGTACATATTGTCCAAATGTTCATCAACACTTCTTGA

Amino Acid

IL15 Signal Peptide- *Proprotein*- Mature peptide (162 aa)

MRISKPHLRSISIQCYLCLLLNSHFLTEA*GIHVFILGCFSAGLPKTEA*NWVNVISDLKKIEDLIQSMHIDATLYTESDVHPSCKVTAMK
CFLLELQVISLESGDASIHDTVENLIILANNSLSSNGNVTESGCKECEELEEKNIKEFLQSFVHIVQMFINTS

SEQUENCE LISTING

<160> NUMBER OF SEQ ID NOS: 4

<210> SEQ ID NO 1
<211> LENGTH: 638
<212> TYPE: DNA
<213> ORGANISM: Artificial Sequence
<220> FEATURE:
<223> OTHER INFORMATION: Membrane-bound IL-15/CD8a fusion protein

<400> SEQUENCE: 1

```
gaattcgccc ttccaccatg gccttaccag tgaccgcctt gctcctgccg ctggccttgc      60
tgctccacgc cgccaggccg aactgggtga atgtaataag tgatttgaaa aaaattgaag     120
atcttattca atctatgcat attgatgcta ctttatatac ggaaagtgat gttcacccca     180
gttgcaaagt aacagcaatg aagtgctttc tcttggagtt acaagttatt tcacttgagt     240
ccggagatgc aagtattcat gatacagtag aaaatctgat catcctagca aacaacagtt     300
tgtcttctaa tgggaatgta acagaatctg gatgcaaaga atgtgaggaa ctggaggaaa     360
aaaatattaa agaatttttg cagagttttg tacatattgt ccaaatgttc atcaacactt     420
ctaccacgac gccagcgccg cgaccaccaa cacggcgcc caccatcgcg tcgcagcccc      480
tgtccctgcg cccagaggcg tgccggccag cggcgggggg cgcagtgcac acgagggggc     540
tggacttcgc ctgtgatatc tacatctggg cgcccttggc cgggacttgt ggggtccttc     600
tcctgtcact ggttatcacc ctttactgct aactcgag                             638
```

<210> SEQ ID NO 2
<211> LENGTH: 204
<212> TYPE: PRT
<213> ORGANISM: Artificial Sequence
<220> FEATURE:
<223> OTHER INFORMATION: Membrane-bound IL-15/CD8a fusion protein

<400> SEQUENCE: 2

Met Ala Leu Pro Val Thr Ala Leu Leu Pro Leu Ala Leu Leu Leu
1               5                   10                  15

His Ala Ala Arg Pro Asn Trp Val Asn Val Ile Ser Asp Leu Lys Lys
            20                  25                  30

Ile Glu Asp Leu Ile Gln Ser Met His Ile Asp Ala Thr Leu Tyr Thr
        35                  40                  45

Glu Ser Asp Val His Pro Ser Cys Lys Val Thr Ala Met Lys Cys Phe
    50                  55                  60

Leu Leu Glu Leu Gln Val Ile Ser Leu Glu Ser Gly Asp Ala Ser Ile
65                  70                  75                  80

His Asp Thr Val Glu Asn Leu Ile Ile Leu Ala Asn Asn Ser Leu Ser
                85                  90                  95

Ser Asn Gly Asn Val Thr Glu Ser Gly Cys Lys Glu Cys Glu Glu Leu
            100                 105                 110

Glu Glu Lys Asn Ile Lys Glu Phe Leu Gln Ser Phe Val His Ile Val
        115                 120                 125

Gln Met Phe Ile Asn Thr Ser Thr Thr Thr Pro Ala Pro Arg Pro Pro
130                 135                 140

Thr Pro Ala Pro Thr Ile Ala Ser Gln Pro Leu Ser Leu Arg Pro Glu
145                 150                 155                 160

Ala Cys Arg Pro Ala Ala Gly Gly Ala Val His Thr Arg Gly Leu Asp
                165                 170                 175

Phe Ala Cys Asp Ile Tyr Ile Trp Ala Pro Leu Ala Gly Thr Cys Gly
            180                 185                 190

Val Leu Leu Leu Ser Leu Val Ile Thr Leu Tyr Cys
            195                 200

<210> SEQ ID NO 3
<211> LENGTH: 489
<212> TYPE: DNA
<213> ORGANISM: Homo sapiens

<400> SEQUENCE: 3
atgagaattt cgaaaccaca tttgagaagt atttccatcc agtgctactt gtgtttactt      60
ctaaacagtc attttctaac tgaagctggc attcatgtct tcattttggg ctgtttcagt     120
gcagggcttc ctaaaacaga agccaactgg gtgaatgtaa taagtgattt gaaaaaaatt     180
gaagatctta ttcaatctat gcatattgat gctactttat atacggaaag tgatgttcac     240
cccagttgca agtaacagc aatgaagtgc tttctcttgg agttacaagt tatttcactt     300
gagtccggag atgcaagtat tcatgataca gtagaaaatc tgatcatcct agcaaacaac     360
agtttgtctt ctaatgggaa tgtaacagaa tctggatgca agaatgtga ggaactggag     420 gaaaaaaata ttaagaatt tttgcagagt tttgtacata ttgtccaaat gttcatcaac     480
acttcttga                                                            489

<210> SEQ ID NO 4
<211> LENGTH: 162
<212> TYPE: PRT
<213> ORGANISM: Homo sapiens

<400> SEQUENCE: 4

Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
            20                  25                  30

```
Val Phe Ile Leu Gly Cys Phe Ser Ala Gly Leu Pro Lys Thr Glu Ala
        35                  40                  45

Asn Trp Val Asn Val Ile Ser Asp Leu Lys Lys Ile Glu Asp Leu Ile
    50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
        115                 120                 125

Thr Glu Ser Gly Cys Lys Glu Cys Glu Glu Leu Glu Glu Lys Asn Ile
    130                 135                 140

Lys Glu Phe Leu Gln Ser Phe Val His Ile Val Gln Met Phe Ile Asn
145                 150                 155                 160

Thr Ser
```

IMMUNE CELLS EXPRESSING MEMBRANE-BOUND INTERLEUKIN 15 (MBIL15) AND USES THEREOF

RELATED APPLICATIONS

This application is a continuation of U.S. application Ser. No. 16/550,548, filed Aug. 26, 2019, which is a divisional of U.S. application Ser. No. 15/309,362, filed Nov. 7, 2016, which is the U.S. National Stage of International Application No. PCT/SG2015/050111, filed on May 14, 2015, published in English, which claims the benefit of U.S. Provisional Application No. 61/993,494, filed on May 15, 2014. The entire teachings of the above applications are incorporated herein by reference.

INCORPORATION BY REFERENCE OF MATERIAL IN ASCII TEXT FILE

This application incorporates by reference the Sequence Listing contained in the following ASCII text file:
a) File name: 44591097004_SEQUENCELISTING.txt; created Aug. 5, 2020, 5,436 bytes in size.

BACKGROUND OF THE INVENTION

Survival and proliferation of NK cells in vivo requires stimulation by cytokines, such as IL-2 and IL-15. For example, after injection in immunodeficient mice, activated NK cells became undetectable after 1 week but persisted for up to one month if human IL-2 was also administered. Hence, clinical protocols using NK cell infusions typically rely on IL-2 administration to prolong NK cells survival in patients. However, IL-2 can have considerable side effects. In addition to fever and chills, IL-2 administration can lead to more serious and potentially fatal consequences, such as capillary leak syndrome. Decreasing the dose of IL-2 should reduce the risk of side effects but can result in stimulation of regulatory T cells which can inhibit NK cell function and possibly nullify its anti-cancer effect.

Hence, it would be important to develop alternative ways to promote NK cell expansion and activity in vitro and/or in vivo.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIGS. 2A-2C: Survival and expansion of NK cells expressing IL-15 in vitro. 2A. Percentage of NK cell recovery as compared to input cells after 7-day parallel cultures without IL-2 for mock- and mbIL15 transduced cells from 15 donors (left panel) and mbIL15- or wtIL15-transduced cells from 9 donors (right panel). Horizontal bars indicate median value. Results of paired t tests are shown. Results of cultures with IL-2 (10 and 100 IU/mL) are shown in FIG. 6B. Survival and expansion of mock- and mbIL15-transduced NK cells from 6 donors with low dose IL-2 (10 IU/mL). 2C. Expansion and long-term survival of NK cells from one donor transduced with mbIL15, wtIL15 or mock-transduced cultured with no IL-2 or low dose IL-2 (results with 100 IU/mL IL2 are shown in FIG. 6). Percentage of NK cell recovery at the indicated days of culture is shown.

FIGS. 4A-4C: Properties of NK cells expressing mbIL15. 4A. Relative proportion of GFP+ cells before and after 7 days of culture among NK cell populations transduced with mbIL15 or mock-transduced. Results with NK cells from 13 donors are shown; P<0.001 for mbIL15, not significant for mock. 4B. Immunophenotypic features of mbIL15-transduced NK cells. Cells marker analysis by flow cytometry was performed on NK cells cultured for 48 hours without IL-2. All results are summarized in the Table. 4C. Mock- and mbIL15-transduced NK cells were cultured for 48 hours without IL-2 and cell lysates were analyzed by Kinex Antibody Microarray (Kinexus). Of 809 anti-phosphoprotein antibodies tested, shown are those whose signals had a Z-ratio >0.5 and a % Error Range <100. Bars indicate percent signal change in NK cells expressing mbIL15 as compared to the normalized intensity in mock-transduced NK cells.

FIGS. 5A-5D: Anti-tumor capacity of NK cells expressing mbIL15. 5A. Results of 24-hour cytotoxicity assays with mbIL15- and mock-transduced NK cells from 9 donors against the Nalm-6, U937, K562, Daudi, SK-BR-3, and ES8 cell lines at 1:4 and 1:1 E:T ratio (15 experiments at each ratio; P<0.001 for both). Results obtained with individual cell lines in 4-hour and 24-hour cytotoxicity assays are shown in FIG. 7. 5B. NK cells expressing mbIL15 have an increased release of lytic granules in the presence of target cells. Percentage of CD107a+ NK cells after 4-hour cytotoxicity assays at 1:1 E:T. Results with NK cells from 3 donors against 2 cell lines are shown (P=0.007). 5C. NK cells expressing mbIL15 exert anti-tumor activity in vivo. NOD-SCID-IL2RGnull mice were injected i.p. with $1\times10^4$ U937 cells labeled with luciferase. In 3 mice, no treatment was given ("No NK"), while 4 mice received mock-transduced NK cells (1×10⁷ i.p.) on days 3 and 7, and 4 other mice mbIL15-transduced NK cells at the same dose and schedule. Results of in vivo imaging of tumor growth are shown (ventral images). 5D. Overall survival comparisons of mice in the different treatment groups. Mice were euthanized when bioluminescence reached 1×10¹¹ photons/second. P values for log rank test of the 3 curves, and for comparisons between each of 2 curves are shown.

FIGS. 6A-6C: Survival and expansion of NK cells expressing IL-15 in vitro. 6A. Expansion of NK cells expressing mbIL15 in the absence of IL-2 is suppressed by an anti-IL-15 neutralizing antibody. Symbols show mean (±SD; n=3) NK cell recovery during culture as compared to input cells in experiments with NK cells transduced with mbIL15. 6B. Percentage of NK cell recovery as compared to input cells after 7-day parallel cultures with low- (10 IU/mL) and high-dose (100 IU/mL) IL-2 for mock-, mbIL15- and wtIL15-transduced cells from 6 donors. Horizontal bars indicate median value. Results of paired t tests are shown. 6C. Expansion and long-term survival of NK cells from one donor transduced with mbIL15 or wtIL15 and cultured with 100 IU/mL IL2. Percentage of NK cell recovery at the indicated days of culture is shown.

FIGS. 7A-7B: Anti-tumor capacity of NK cells expressing mbIL15. Results of 4-hour (7A) and 24-hour cytotoxicity assays (7B) with mbIL15- and mock-transduced NK cells against the Nalm-6, U937, K562, Daudi, SK-BR-3, and ES8 cell lines at 1:4, 1:2 and 1:1 E:T ratio are shown. Each symbol indicates mean±SD cytotoxicity in experiments with NK cells from 3 different donors for U937, K562, ES8, and 2 donors for Nalm-6, Daudi and SK-BR-3, all performed in triplicate (P<0.001 for all experiments).

FIGS. 8A-8C: Anti-tumor capacity of NK cells expressing mbIL15. NOD-SCID-IL2RGnull mice were injected i.p. with 1×10⁵ ES8 cells labeled with luciferase. In 7 mice, no treatment was given ("No NK"), while 11 mice received mock-transduced NK cells (1×10⁷ i.p.) on day 3, and 12 other mice mbIL15-transduced NK cells at the same dose and schedule. 8A. Results of in vivo imaging of tumor growth. Ventral images of the 4 mice with the highest tumor signal in each group are shown. 8B. Results of in vivo imaging of tumor growth. Each symbol corresponds to one bioluminescence measurement (photon/second relative day 3 measurements in each mouse). 8C. Overall survival comparisons of mice in the different treatment groups. Mice were euthanized when bioluminescence reached 1×10¹⁰ photons/second. P values for log rank test of the 3 curves, and for comparisons between each of 2 curves are shown.

FIG. 9 shows the nucleotide sequence (SEQ ID NO: 1) and the amino acid sequence (SEQ ID NO: 2) of membrane bound IL-15.

FIG. 10 shows the nucleotide sequence (SEQ ID NO: 3) and amino acid sequence (SEQ ID NO: 4) of human IL-15 (NCBI Reference Sequence: NM_000585.4).

DETAILED DESCRIPTION OF THE INVENTION

Figure 1A:
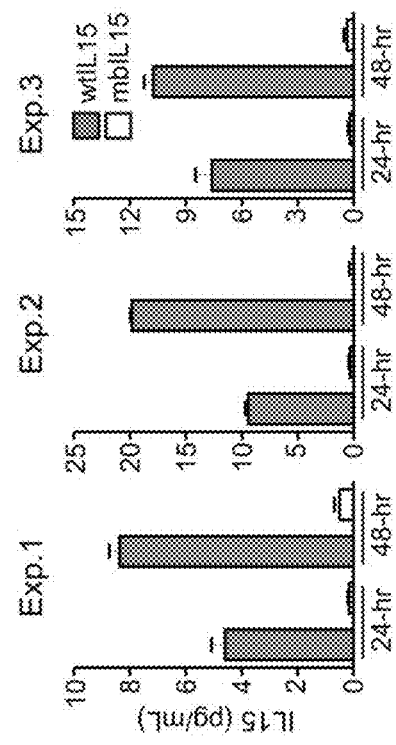
FIGS. 1A-1C: Design and expression of IL-15 constructs. 1A. Schematic representation of the wild-type and membrane-bound IL-15 constructs ("wtIL15" and "mbIL15") used in this study. 1B. Expression of IL-15 on the surface of NK cells transduced with mbIL15. Expanded NK cells were transduced with wtIL15, mbIL15 or with a vector containing GFP alone ("Mock"). Flow cytometry dot plots illustrate expression of GFP and IL-15, as detected by an anti-IL15 antibody (R&D Systems) and a goat-anti-mouse secondary antibody conjugated to phycoerythrin (Southern Biotechnology Associates). Percentage of cells (>98% CD56+CD3-NK cells) in each quadrant is shown. 1C. Secretion of IL-15 by NK cells transduced with wtIL15. NK cells from 3 different donors were tested in triplicate. Bars indicate mean±SD of ELISA measurements performed in supernatants collected after 24 and 48 hours of culture without IL-2. No IL-15 was detected in the supernatants of mock-transduced cells.

A description of example embodiments of the invention follows.

The well-established anti-leukemic activity of natural killer (NK) cells indicates therapeutic potential for NK cell infusions. NK cell survival and, hence, cytotoxicity requires cytokine support. Described herein are experiments investigating whether expression of interleukin-15 (IL-15) in a non-secretory, membrane-bound form could sustain NK cell growth. The human IL15 gene was linked to that encoding CD8a transmembrane domain ("mbIL15"). After retroviral transduction, human NK cells expressed mbIL-15 on the cell surface but IL-15 secretion was negligible. Survival and expansion of mbIL15-NK cells without IL-2 was vastly superior to that of mock-transduced cells (after 7-day culture, P<0.0001, n=15), and to that of NK cells secreting non-membrane bound IL-15 (P=0.025, n=9); viable mbIL15-NK cells were detectable for up to 2 months. In immunodeficient mice, mbIL15-NK cells expanded without IL-2, and were detectable in all tissues examined (except brain) in much higher numbers than mock-transduced NK cells (P<0.001). Expansion in vitro and in vivo further increased with IL-2. The primary mechanism of mbIL15 stimulation was autocrine; it activated IL-15 signaling and anti-apoptotic signaling. Cytotoxicity against leukemia, lymphoma and solid tumor cell lines was consistently higher with mbIL15-NK cells. Median 24-hour cytotoxicity at 1:4

E:T was 71% versus 22% with mock-transduced cells; at 1:1 E:T, it was 99% versus 54% (P<0.0001). Increased anti-tumor capacity was also evident in immunodeficient mice engrafted with leukemia (U937) or sarcoma (ES8) cells. Thus, mbIL15 conferred independent growth to NK cells and enhanced their anti-tumor capacity. Infusion of mbIL15-NK cells allows NK cell therapy without the adverse effects of IL-2.

Accordingly, provided herein is a (one or more; a plurality) cell that expresses all or a functional portion of interleukin-15 (IL-15), wherein the cell is a cell that responds to IL-15. A cell that responds to IL-15 includes a cell in which one or more of its activities are regulated by IL-15. Examples of such cells include natural killer (NK) cells, T-cells, dendritic cells and moncytes. The one or more (e.g., isolated) cells can express all or a functional portion of IL-15 as a membrane-bound polypeptide, as a secretory protein or as a combination thereof.

In one aspect, the invention is directed to a natural killer (NK) cell(s) that expresses all or a functional portion of interleukin-15 (IL-15). The one or more (e.g., isolated) NK cells can express all or a functional portion of IL-15 as a membrane-bound polypeptide, as a secretory protein or as a combination thereof.

As used herein, "Natural Killer Cells" ("NK cells") refer to a type of cytotoxic lymphocyte of the immune system. NK cells provide rapid responses to virally infected cells and respond to transformed cells. Typically immune cells detect peptides from pathogens presented by Major Histocompatibility Complex (MHC) molecules on the surface of infected cells, triggering cytokine release, causing lysis or apoptosis. NK cells are unique, however, as they have the ability to recognize stressed cells regardless of whether peptides from pathogens are present on MHC molecules. They were named "natural killers" because of the initial notion that they do not require prior activation in order to kill target. NK cells are large granular lymphocytes (LGL) and are known to differentiate and mature in the bone marrow from where they then enter into the circulation.

In some aspects, the NK cell is a mammalian NK cell. Examples of "mammalian" or "mammals" include primates (e.g., human), canines, felines, rodents, porcine, ruminants, and the like. Specific examples include humans, dogs, cats, horses, cows, sheep, goats, rabbits, guinea pigs, rats and mice. In a particular aspect, the mammalian NK cell is a human NK cell.

As used herein "Interleukin-15" ("IL-15") refers to a cytokine that regulates T and NK cell activation and proliferation. This cytokine and interleukin 2 share many biological activities. They are found to bind common receptor subunits, and may compete for the same receptor, and thus negatively regulate each other's activity. The number of CD8+ memory cells is shown to be controlled by a balance between IL-15 and IL-2. This cytokine induces the activation of JAK kinases, as well as the phosphorylation and activation of transcription activators STAT5, STAT5, and STAT6 and may increase the expression of apoptosis inhibitor BCL2L1/BCL-x(L), possibly through the transcription activation activity of STAT6, and thus prevent apoptosis.

A "functional portion" ("biologically active portion") of IL-15 refers to a portion of IL-15 that retains one or more functions of full length or mature IL-15. Such functions include the promotion of NK cell survival, regulation of NK cell and T cell activation and proliferation as well as the support of NK cell development from hematopoietic stem cells.

As will be appreciated by those of skill in the art, the sequence of a variety of IL-15 molecules are known in the art. In one aspect, the IL-15 is a wild type IL-15. In some aspects, the IL-15 is a mammalian IL-15 (e.g., *Homo sapiens* interleukin 15 (IL15), transcript variant 3, mRNA, NCBI Reference Sequence: NM_000585.4; *Canis lupus familiaris* interleukin 15 (IL15), mRNA, NCBI Reference Sequence: NM_001197188.1; *Felis catus* interleukin 15 (IL15), mRNA, NCBI Reference Sequence: NM_001009207.1). Examples of "mammalian" or "mammals" include primates (e.g., human), canines, felines, rodents, porcine, ruminants, and the like. Specific examples include humans, dogs, cats, horses, cows, sheep, goats, rabbits, guinea pigs, rats and mice. In a particular aspect, the mammalian IL-15 is a human IL-15.

All or a functional portion of IL-15 can be expressed by one or more NK cells (as a membrane-bound and/or secreted polypeptide) in a variety of ways. For example, all or a functional portion of the IL-15 can be expressed within the NK cell and secreted from the NK cell and/or can be linked (conjugated; fused) directly or indirectly (e.g., ionic, non-ionic, covalent linkage) to the surface (e.g., at the surface, or within the membrane, of an NK cell) of the NK cell using any of a variety of linkers known in the art (Hermanson, G., *Bioconjugate Techniques*, Academic Press 1996). In particular aspects, all or a functional portion of the IL-15 is linked to all or a portion of a transmembrane protein. In one aspect, the NK cell expresses a fusion protein comprising all or a portion of IL-15 fused to all or a portion of a transmembrane protein. In a particular aspect, the portion of the transmembrane protein comprises all or a portion of a transmembrane domain of the transmembrane protein.

As used herein, a "transmembrane protein" or "membrane protein" is a protein located at and/or within a membrane such as the phospholipid bilayer of a biological membrane (e.g., biomembranes such as the membrane of a cell). Membrane proteins enable the membrane to carry out its distinctive activities. The complement of proteins attached to a membrane varies depending on cell type and subcellular location. Some proteins are bound only to the membrane surface, whereas others have one or more regions buried within the membrane and/or domains on one or both sides of the membrane. Protein domains on the extracellular membrane surface are generally involved in cell-cell signaling or interactions. Domains lying along the cytosolic face of the membrane have a wide range of functions, from anchoring cytoskeletal proteins to the membrane to triggering intracellular signaling pathways. Domains within the membrane, referred to herein as "transmembrane domains", particularly those that form channels and pores, move molecules across the membrane. A "transmembrane domain", is a three-dimensional protein structure which is thermodynamically stable in a membrane (e.g., a membrane of a vesicle such as a cell). Examples of transmembrane domains include a single alpha helix, a stable complex of several transmembrane alpha helices, a transmembrane beta barrel, a beta-helix of gramicidin A, or any other structure. Transmembrane helices are usually about 20 amino acids in length.

Typically, membrane proteins are classified into two broad categories—integral (intrinsic) and peripheral (extrinsic)—based on the nature of the membrane-protein interactions. Most biomembranes contain both types of membrane proteins.

Integral membrane proteins, also called intrinsic proteins, have one or more segments that are embedded in the phospholipid bilayer. Integral membrane proteins include transmembrane proteins and lipid-anchored proteins. Most integral proteins contain residues with hydrophobic side chains that interact with fatty acyl groups of the membrane phospholipids, thus anchoring the protein to the membrane. Most integral proteins span the entire phospholipid bilayer. These transmembrane proteins contain one or more membrane-spanning domains as well as domains, from four to several hundred residues long, extending into the aqueous medium on each side of the bilayer. Typically, the membrane-spanning domains are one or more (e.g., about 1, 2, 3, 4, 5, 6, 7, 8, 9, 10 or more) α helices and/or β strands. Membrane-spanning α-helical domains are typically embedded in membranes by hydrophobic interactions with the lipid interior of the bilayer and probably also by ionic interactions with the polar head groups of the phospholipids (e.g., glycophorin). The structure of β strands are typically in the form of membrane spanning barrels (e.g., porin). Some integral proteins are anchored to one of the membrane leaflets by covalently bound fatty acids. In these proteins, the bound fatty acid is embedded in the membrane, but the polypeptide chain does not enter the phospholipid bilayer. Some cell-surface proteins are anchored to the exoplasmic face of the plasma membrane by a complex glycosylated phospholipid that is linked to the C-terminus (e.g., glycosylphosphatidylinositol, alkaline phosphatase). Some cytosolic proteins are anchored to the cytosolic face of membranes by a hydrocarbon moiety covalently attached to a cysteine near the C-terminus (e.g., prenyl, farnesyl, and geranylgeranyl groups). In another group of lipid-anchored cytosolic proteins, a fatty acyl group (e.g., myristate or palmitate) is linked by an amide bond to the N-terminal glycine residue.

Peripheral membrane proteins, or extrinsic proteins, do not interact with the hydrophobic core of the phospholipid bilayer. Instead they are usually bound to the membrane indirectly by interactions with integral membrane proteins or directly by interactions with lipid polar head groups. Peripheral proteins localized to the cytosolic face of the plasma membrane include the cytoskeletal proteins spectrin and actin in erythrocytes and the enzyme protein kinase C. This enzyme shuttles between the cytosol and the cytosolic face of the plasma membrane and plays a role in signal transduction. Other peripheral proteins, including certain proteins of the extracellular matrix, are localized to the outer (exoplasmic) surface of the plasma membrane.

Examples of transmembrane proteins include a receptor, a ligand, an immunoglobulin, a glycophorin or a combination thereof. Specific examples of transmembrane proteins include CD8α, CD4, CD3ε, CD3γ, CD3δ, CD3ζ, CD28, CD137, FcεRIγ, a T-cell receptor (TCR such as TCRα and/or TCRβ), a nicotinic acetylcholine receptor, a GABA receptor, or a combination thereof. Specific examples of immunoglobulins include IgG, IgA, IgM, IgE, IgD or a combination thereof. Specific examples of glycophorin include glycophorin A, glycophorin D or a combination thereof.

In addition to being linked to all or a portion of a transmembrane protein, all or a functional portion of the IL-15 can be linked to other components such as a signal peptide (e.g., a CD8α signal sequence), a leader sequence, a secretory signal, a label (e.g., a reporter gene), etc. In a particular aspect, the all or a functional portion of IL-15 is fused to a signal peptide of CD8α and all or a portion of a transmembrane domain of CD8α.

In another aspect, the invention is directed to a method of producing a natural killer (NK) cell that expresses all or a functional portion of interleukin-15 (IL-15). All or a portion of the IL-15 can be expressed as a membrane-bound polypeptide, a secreted polypeptide or as a combination thereof. The method comprises introducing nucleic acid encoding all or a functional portion of IL-15 into the one or more NK cells. In one aspect, the nucleic acid encoding all or a functional portion of IL-15 is linked (e.g., fused) to all or a portion of a transmembrane protein. Alternatively, or in addition, nucleic acid encoding all or a functional portion of IL-15 is introduced into the NK cell (e.g., wild type IL-15). As will be apparent to those of skill in the art, aspects in which nucleic acid encoding all or a functional portion if IL-15 and all or a functional portion of IL-15 fused to all or a portion of a transmembrane protein is introduced in to NK cell, can be done so using a single nucleic acid or multiple (e.g., separate; two) nucleic acids. The NK cell is maintained under conditions in which all or a functional portion of the IL-15 is expressed as a membrane-bound polypeptide and/or as a secreted polypeptide thereby producing a NK cell that expresses all or a functional portion of IL-15 as a membrane-bound polypeptide and/or as a secreted polypeptide. In a particular aspect, nucleic acid encoding all or a functional portion of IL-15 is fused to a signal peptide of CD8α and all or a portion of a transmembrane domain of CD8α is introduced into the NK cell.

In yet another aspect, the invention is directed to a method of enhancing expansion and/or survival of NK cells (e.g., in vitro, ex vivo, and/or in vivo). The method comprises introducing nucleic acid encoding all or a functional portion of IL-15. Nucleic acid encoding all or a portion of the IL-15 (e.g., wild type IL-15) and/or encoding all or a functional portion of IL-15 fused to all or a portion of a transmembrane protein can be introduced into the NK cell. Thus, the NK cell can express all or a functional portion of IL-15 as a membrane-bound polypeptide, a secreted polypeptide or as a combination thereof. The NK cells are maintained under conditions in which all or a portion of the IL-15 is expressed as a membrane-bound polypeptide, a secreted polypeptide or as a combination thereof and in which the NK cells proliferate. In a particular aspect, nucleic acid encoding all or a functional portion of IL-15 is fused to a signal peptide of CD8α and all or a portion of a transmembrane domain of CD8α is introduced into the NK cell. In some aspects, the method can further comprise contacting the NK cells comprising membrane-bound IL-15 and/or secreted IL-15 with IL-2. In some aspects, the concentration of IL-2 is from about 10 IU/ml to about 1000 IU/ml. In other aspects, the concentration of IL-2 is about 20, 40, 60, 80, 100, 120, 140, 160, 180, 200, 220, 240, 260, 280, 300, 320, 340, 360, 380, 400, 420, 440, 460, 480, 500, 520, 540, 560, 580, 600, 620, 640, 660, 680, 700, 720 740, 760, 780, 800, 820, 840, 860, 880, 900, 920, 940, 960, 980 IU/ml.

As will be apparent to those of skill in the art, a variety of methods for introducing nucleic acid (e.g., transfection, transduction, and/or transposon system) encoding all or a functional portion of IL-15 as a transmembrane polypeptide and/or as a secreted polypeptide into a NK cell can be used. Examples of such methods include chemical-based methods (e.g., involving the use of calcium phosphate; highly branched organic compounds (e.g., dendrimers); liposomes (lipofection); and/or cationic polymers (e.g., DEAE dextran; polyethylenimine)), non-chemical-based methods (e.g., electroporation; cell squeezing; sonoporation; optical transfection; impalefection; hydrodynamic delivery), particle-based methods (e.g., gene gun; magnetofection; particle bombardment), vector-based methods (e.g., vectors including viral vectors such as retroviral vector, lentiviral vectors, adenoviral vectors, etc.), nucleotransfection, transposon-based methods (e.g., Sleeping Beauty, PiggyBAC, etc.) and/or RNA transfection.

Also apparent to those of skill in the art is that a variety of methods of maintaining NK cells under conditions in which (i) all or a functional portion of the IL-15 is expressed as a membrane-bound polypeptide and/or as a secreted polypeptide and/or (ii) the NK cells comprising membrane-bound IL-15 and/or secreted IL-15 proliferate can be used. For example, NK cells can be grown and/or maintained at an appropriate temperature and gas mixture (e.g., about 25° C. to about 37° C., about 5% $CO_2$ in a cell incubator). Culture conditions can vary widely, and variation of conditions for a particular cell type can result in different phenotypes. In addition to temperature and gas mixture, a commonly varied factor in culture systems is the cell growth medium. Recipes for growth media can vary in pH, glucose concentration, growth factors, and the presence of other nutrients. The growth factors used to supplement media are often derived from the serum of animal blood, such as fetal bovine serum (FBS), bovine calf serum, equine serum, porcine serum and/or human platelet lysate (hPL). Other factors considered for maintaining cells include plating density (number of cells per volume of culture medium) and growth of the cells in suspension or adherent cultures.

The methods can further comprise isolating or separating the one or more NK cells produced by the methods provided herein. In addition, the methods can further comprise culturing the one or more NK cells. In some aspects, an NK cell line is produced.

The invention also encompasses a (one or more) natural killer (NK) cell or cell line produced by the methods described herein, and compositions comprising the NK cells provided herein. In a particular aspect, the composition is a pharmaceutical composition comprising one or more of the NK cells or cell lines provided herein. The pharmaceutical composition can further comprise all or a functional portion of IL-2 (e.g., all or a functional portion of an (one or more) IL-2 protein; nucleic acid encoding all or a functional portion of IL-2).

As used herein, "IL-2" refers to a member of a cytokine family that also includes IL-4, IL-7, IL-9, IL-15 and IL-21. IL-2 signals through a receptor complex consisting of three chains, termed alpha, beta and gamma. The gamma chain is shared by all members of this family of cytokine receptors. IL-2, which similar to IL-15, facilitates production of immunoglobulins made by B cells and induces the differentiation and proliferation of NK cells. Primary differences between IL-2 and IL-15 are found in adaptive immune responses. For example, IL-2 is necessary for adaptive immunity to foreign pathogens, as it is the basis for the development of immunological memory. On the other hand, IL-15 is necessary for maintaining highly specific T cell responses by supporting the survival of CD8 memory T cells.

In another aspect, the invention is directed to a method of treating a disease and/or condition involving NK cell therapy in an individual in need thereof comprising administering to the individual a natural killer (NK) cell that expresses all or a functional portion of interleukin-15 (IL-15). In particular aspects, the NK cells express all or a functional portion of IL-15 as a membrane-bound polypeptide and/or as a secreted polypeptide. As is known in the art, diseases and/or conditions that involve NK cell therapy include NK cell deficiencies, cancer, autoimmune diseases, infectious diseases and the like.

In a particular aspect, the invention is directed to a method of treating cancer (e.g., a tumor) in an individual in need thereof comprising administering to the individual a natural killer (NK) cell that expresses all or a functional portion of interleukin-15 (IL-15). All or a functional portion of IL-15 can be expressed as a membrane-bound polypeptide and/or as a secreted polypeptide.

The method can further comprise administering one or more antibodies, antigenic fragments and/or fusions thereof specific to the cancer (e.g., tumor). For example, the method can further comprise administering one or more antibodies directed against one or more tumor antigens. As will be appreciated by those of skill in the art, the one or more antibodies can be a polyclonal antibody, a monoclonal antibody, a multivalent (e.g., bivalent, trivalent) antibody, a chimeric antibody, a humanized antibody, etc. and combinations thereof. A variety of antigenic fragments and/or fusions are also known in the art and include Fab', $F(ab')_2$, single chain variable fragment (scFv), multivalent scFv (e.g., di-scFv, tri-scFv), single domain antibody (nanobody) and etc.

In some aspects, the cancer is a leukemia (e.g., acute lymphoblastic leukemia; acute myeloid leukemia; chronic myelogenous leukemia, chronic lymphocytic leukemia), a myelodysplastic syndrome, a lymphoma (e.g., B cell non-Hodgkin lymphoma, Hodgkin lymphoma, T-cell lymphoblastic lymphoma, anaplastic large cell lymphoma), a solid tumor (e.g., a breast cancer, prostate cancer, gastric cancer, colon cancer, hepatocellular carcinoma, nasopharyngeal carcinoma, neuroblastoma, high grade glioma), a sarcoma (e.g., Ewing sarcoma, rhabdomyosarcoma, non-rhabdomyosarcoma soft-tissue sarcoma, osteosarcoma).

The method of treating cancer can further comprise administering IL-2 (all or a functional portion of IL-2 protein; nucleic acid encoding all or a functional portion of IL-2) to the individual. In one aspect, the IL-2 is mammalian IL-2, such as human IL-2. In a particular aspect, a low dose of the IL-2 is administered to the individual. As used herein, a "low dose" of IL-12 refers to a dose of IL-2 of about 1 million $IU/m^2$ or less (e.g., about 800,000 $IU/m^2$; 600,000 $IU/m^2$; 400,000 $IU/m^2$; 200,000 $IU/m^2$; 100,000 $IU/m^2$; 80,000 $IU/m^2$; 60,000 $IU/m^2$; 40,000 $IU/m^2$; 20,000 $IU/m^2$; 10,000 $IU/m^2$; 8,000 $IU/m^2$; 6,000 $IU/m^2$; 4,000 $IU/m^2$; 2,000 $IU/m^2$; 1,000 $IU/m^2$; 800 $IU/m^2$; 600 $IU/m^2$; 400 $IU/m^2$; 200 $IU/m^2$; 100 $IU/m^2$). In contrast, a normal dose of IL-2 is about 1 million $IU/m^2$ to about 5 million $IU/m^2$.

The one or more natural killer (NK) cell(s) that express all or a functional portion of interleukin-15 (IL-15) (e.g., therapeutic compound; pharmaceutical composition) are administered in a therapeutically effective amount (i.e., an amount that is sufficient to treat the cancer, such as by ameliorating symptoms associated with the cancer, preventing or delaying the onset of the cancer, also lessening the severity or frequency of symptoms of the cancer and/or preventing, delaying or overcoming metastasis of the cancer). The amount that will be therapeutically effective in the treatment of a particular individual will depend on the symptoms and severity of the condition (e.g., cancer), and can be determined by standard clinical techniques. In addition, in vitro or in vivo assays may optionally be employed to help identify optimal dosage ranges. The precise dose to be employed in the formulation will also depend on the route of administration, and the seriousness of the cancer, and should be decided according to the judgment of a practitioner and each patient's circumstances. Effective doses may be extrapolated from dose-response curves derived from in vitro or animal model test systems.

The therapeutic compound can be delivered in a composition (e.g., a pharmaceutical composition), as described above, or by themselves. They can be administered systemically, or can be targeted to a particular tissue. The therapeutic compounds can be produced by a variety of means, including chemical synthesis; recombinant production; in vivo production (e.g., a transgenic animal, such as U.S. Pat. No. 4,873,316 to Meade et al.), for example, and can be isolated using standard means such as those described herein. A combination of any of the above methods of treatment can also be used.

The compounds for use in the methods described herein can be formulated with a physiologically acceptable carrier or excipient to prepare a pharmaceutical composition. The carrier and composition can be sterile. The formulation should suit the mode of administration.

Suitable pharmaceutically acceptable carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, dextrose, magnesium stearate, talc, silicic acid, viscous paraffin, perfume oil, fatty acid esters, hydroxymethylcellulose, polyvinyl pyrolidone, etc., as well as combinations thereof. The pharmaceutical preparations can, if desired, be mixed with auxiliary agents, e.g., lubricants, preservatives, stabilizers, wetting agents, emulsifiers, salts for influencing osmotic pressure, buffers, coloring, flavoring and/or aromatic substances and the like that do not deleteriously react with the active compounds.

The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, polyvinyl pyrollidone, sodium saccharine, cellulose, magnesium carbonate, etc.

Methods of introduction of these compositions include, but are not limited to, intradermal, intramuscular, intraperitoneal, intravenous, subcutaneous, topical, oral and intranasal. Other suitable methods of introduction can also include gene therapy (as described below), rechargeable or biodegradable devices, particle acceleration devises ("gene guns") and slow release polymeric devices. The pharmaceutical compositions of this invention can also be administered as part of a combinatorial therapy with other compounds.

The composition can be formulated in accordance with the routine procedures as a pharmaceutical composition adapted for administration to human beings. For example, compositions for intravenous administration typically are solutions in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active compound. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

For topical application, nonsprayable forms, viscous to semi-solid or solid forms comprising a carrier compatible with topical application and having a dynamic viscosity preferably greater than water, can be employed. Suitable formulations include but are not limited to solutions, suspensions, emulsions, creams, ointments, powders, enemas, lotions, sols, liniments, salves, aerosols, etc., that are, if desired, sterilized or mixed with auxiliary agents, e.g., preservatives, stabilizers, wetting agents, buffers or salts for influencing osmotic pressure, etc.

Compounds described herein can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

In yet other aspects, the invention is directed to pharmaceutical compositions comprising one or more NK cells that expresses all or a functional portion of interleukin-15 (IL-15) as a membrane-bound polypeptide. The invention is also directed to compositions (e.g., pharmaceutical compositions) for use as a medicament in therapy. For example, the agents identified herein can be used in the treatment of cancer. In addition, the agents identified herein can be used in the manufacture of a medicament for the treatment of cancer.

As used herein an "individual" refers to an animal, and in a particular aspect, a mammal. Examples of mammals include primates, a canine, a feline, a rodent, and the like. Specific examples include humans, dogs, cats, horses, cows, sheep, goats, rabbits, guinea pigs, rats and mice. The term "individual in need thereof" refers to an individual who is in need of treatment or prophylaxis as determined by a researcher, veterinarian, medical doctor or other clinician. In one embodiment, an individual in need thereof is a mammal, such as a human.

An (one or more) "isolated," "substantially pure," or "substantially pure and isolated" NK cell, as used herein, is one that is separated from (substantially isolated with respect to) the complex cellular milieu in which it naturally occurs, or culture medium when produced by recombinant techniques, or chemical precursors or other chemicals when chemically synthesized. In some instances, the isolated material will form part of a composition (for example, a crude extract containing other substances), buffer system, or reagent mix. In other circumstances, the material may be purified to essential homogeneity, for example, as determined by agarose gel electrophoresis or column chromatography such as HPLC. Preferably, an NK cell comprises at least about 50%, 80%, 90%, 95%, 98% or 99% (on a molar basis) of all macromolecular species present.

Articles such as "a", "an", "the" and the like, may mean one or more than one unless indicated to the contrary or otherwise evident from the context.

The phrase "and/or" as used herein in the specification and in the claims, should be understood to mean "either or both" of the elements so conjoined. Multiple elements listed with "and/or" should be construed in the same fashion, i.e., "one or more" of the elements so conjoined. Other elements may optionally be present other than the elements specifically identified by the "and/or" clause. As used herein in the specification and in the claims, "or" should be understood to have the same meaning as "and/or" as defined above. For example, when used in a list of elements, "or" or "and/or" shall be interpreted as being inclusive, i.e., the inclusion of at least one, but optionally more than one, of list of elements, and, optionally, additional unlisted elements. Only terms clearly indicative to the contrary, such as "only one of" or "exactly one of" will refer to the inclusion of exactly one element of a number or list of elements. Thus claims that include "or" between one or more members of a group are considered satisfied if one, more than one, or all of the group members are present, employed in, or otherwise relevant to a given product or process unless indicated to the contrary. Embodiments are provided in which exactly one member of the group is present, employed in, or otherwise relevant to a given product or process. Embodiments are provided in which more than one, or all of the group members are present, employed in, or otherwise relevant to a given product or process. Any one or more claims may be amended to explicitly exclude any embodiment, aspect, feature, element, or characteristic, or any combination thereof. Any one or more claims may be amended to exclude any agent, composition, amount, dose, administration route, cell type, target, cellular marker, antigen, targeting moiety, or combination thereof.

Exemplification

Material and Methods

Tumor Cell Lines

The human cell lines Nalm-6 (B-lineage acute lymphoblastic leukemia), Daudi (B-cell lymphoma), K562 and U937 (acute myeloid leukemia), and SK-BR-3 (breast carcinoma) were obtained from the American Type Culture Collection, the Ewing sarcoma cell line ES8 was from the St. Jude Children's Research Hospital tissue repository. All of the cell lines were transduced with a MSCV-internal ribosome entry site (IRES)-GFP retroviral vector (from the St. Jude Vector Development and Production Shared Resource) containing the firefly luciferase gene. Transduced cells were selected for their expression of GFP with a MoFlo (Beckman Coulter, Miami, Fla.) or a FACSAria (BD Biosciences, San Jose, Calif.). RPMI-1640 (Invitrogen, Carlsbad, Calif.) supplemented with 10% fetal bovine serum (FBS; Thermo Fisher Scientific, Waltham, Mass.) and antibiotics were used to maintain all cell lines. Cell lines were characterized by the providers for molecular and/or gene expression features; the cell marker profile of leukemia and lymphoma cell lines was periodically tested by flow cytometry to ensure that no changes had occurred and ES8 was validated by DNA fingerprinting at DSMZ (Braunschweig, Germany).

Human NK Cell Expansion

Peripheral blood samples were obtained from discarded byproducts of platelet collections from healthy adult donors. Mononuclear cells were purified by centrifugation on an Accu-Prep density step (Accurate, Westbury, N.Y.) and washed twice in RPMI-1640. To expand CD56+CD3− NK cells, peripheral blood mononuclear cells and the genetically modified K562-mb15-41BBL cell line were co-cultured, as previously described in Fujisaki et al., *Cancer Res,* 69(9): 4010-4017 (2009); Imai et al., *Blood,* 106:376-383 (2005)). Briefly, peripheral blood mononuclear cells were cultured with 100 Gy-irradiated K562-mb15-41BBL cell at 1.5:1 ratio in SCGM (CellGenix, Freiburg, Germany) containing 10% FBS, antibiotics and 10 IU/mL of recombinant human interleukin-2 (IL-2; Roche, Mannheim, Germany) in 6-well tissue culture plates. Tissue culture medium was partly exchanged every 2 days. After 7 days of co-culture, residual T cells were removed with Dynabeads CD3 (Invitrogen), resulting in cell population containing >95% CD56+CD3− NK cells.

Plasmids, Virus Production and Gene Transduction

The pMSCV-IRES-GFP, pEQ-PAM3(-E), and pRDF were obtained from the St. Jude Vector Development and Production Shared Resource. Interleukin-15 (IL-15) with a long signal peptide was sub-cloned by polymerase chain reaction (PCR) from a human spleen cDNA library (from Dr G. Neale, St Jude Children's Research Hospital) used as a template. The cDNA encoding the signal peptide of CD8α, the mature peptide of IL-15 and the transmembrane domain of CD8α were assembled by the splicing by overlapping extension by PCR (SOE-PCR) to encode a membrane-bound form of IL-15 ("mbIL15"); a wild-type form of IL-15 (not linked to CD8α transmembrane domain; "wtIL15") was also tested prepared. The resulting expression cassettes were sub-cloned into EcoRI and XhoI sites of murine stem-cell virus-internal ribosome entry site-green fluorescent protein (MSCV-IRES-GFP).

To generate RD144-pseudotyped retrovirus, $3.0 \times 10^6$ 293 T cells were transfected using X-tremeGENE 9 DNA (Roche, Mannheim, Germany), maintained in 10-cm tissue culture dishes for 18 h, with 3.5 μg of cDNA encoding mbIL15 constructs, 3.5 μg of pEQ-PAM3(-E), and 3 μg of pRDF. After replacing the medium with RPMI-1640 with 10% FBS and antibiotics at 24 hours, the conditioned medium containing retrovirus was harvested at 36-96 hours and added to polypropylene tubes coated with RetroNectin (Takara, Otsu, Japan), which were centrifugated at 1400 g for 10 min and incubated at 37° C. and 5% $CO_2$ for 4 hours. After additional centrifugation, and removal of the supernatant, expanded NK cells ($0.5-1 \times 10^6$) were added to the tubes and left in at 37° C. for 12 hours; these steps were repeated up to 6 times over 2-3 days. Cells were then maintained in RPMI-1640 with FBS, antibiotics and 100 IU/ml of IL-2. Transduced cells were assayed 3-29 days after transduction.

Surface expression of mbIL-15 was analyzed by flow cytometry using an anti-human IL-15 antibody (R&D, Minneapolis, Minn.) and phycoerythrin conjugated goat anti-mouse IgG1 (Southern Biotech, Birmingham, Ala.). Antibody staining was detected with a Fortessa flow cytometer (Becton Dickinson). Levels of IL-15 in culture supernatants were measured with the Quantikine Immunoassay (R&D).

Functional Analysis of NK Cells In Vitro

To estimate NK cell survival and growth in vitro, transduced NK cells ($1 \times 10^6$ cells/mL) were resuspended in RPMI-1640 with 10% FBS and antibiotics, placed into the wells of either a 24- or a 96-well plate (Costar, Corning, N.Y.) and cultured without or with IL-2 (10-100 IU/ml). Numbers of viable GFP+ cells were determined with an Accuri C6 flow cytometer (Becton Dickinson), after staining with propidium iodide. In some experiments, cells were incubated for 10 minutes with a neutralizing anti-IL-15 antibody (R&D) or an isotype-matched non-reactive antibody before culture.

NK cell immunophenotyping was performed using the antibodies listed in the Table, visualized with a Fortessa flow cytometer and analyzed by Diva (Becton Dickinson) and FlowJo (TreeStar, Ashland, Oreg.) software. For phosphoprotein analysis, mock- and mbIL15-transduced NK cells ($1 \times 10^7$) were cultured without IL-2 for 48 hours. Cell lysates were prepared using a lysis buffer containing 20 mM 3-(N-morpholino) propanesulfonic acid, 2 mM EGTA, 5 mM EDTA, 30 mM sodium fluoride, 60 mM β-glycerophosphate, 20 mM sodium pyrophosphate, 1 mM sodium orthovanadate, 1% Triton X-100, Complete Mini protease inhibitor cocktail (Roche, Mannheim, Germany) and 1 mM dithiothreitol. After sonication, lysates were frozen at −80°

C. and shipped in dry ice to Kinexus (Vancouver, Calif.) for Kinex Antibody Microarray analysis.

For cytotoxicity assays, luciferase-labeled target cells and NK cells (cultured without IL-2 for 48 hours) were plated in 96-well, flat-bottomed black Viewplates (Corning) at various effector:target (E:T) ratios and cultured for 4 or 24 hours. Adherent cell lines were incubated at 37° C. and 5% $CO_2$ for 4 hours before adding NK cells to allow for cell attachment. For antibody-dependent cell cytotoxicity assays, Rituximab (Rituxan, Roche; Mannheim, Germany), Trastuzumab (Herceptin, Roche) or purified human IgG (R&D Systems, Minneapolis, Minn.) were added (all at 1 μg/mL) before NK cells. At the end of the cultures, an equal volume of Bright-Glo luciferase reagent (Promega, Madison, Wis.) was then added to each test well, and after 5 minutes, luminescence was measured using a plate reader and analyzed with Gen5 2.00 software (both from BioTek, Tucson, Ariz.). In each plate, target cell viability was calculated using the luminescent signal from wells containing target cells only. All experiments were done in triplicate.

To measure release of lytic granules, NK cells (cultured for 48 hours without IL-2) were cocultured with K562, U937 cells, or 721.221 cells and their Cw6-expressing variant for 4 hours. We added PE- or PE-Cy7-conjugated anti-CD107a antibody (BD Biosciences) at the beginning of the cultures and GolgiStop (0.15 μL; BD Biosciences) 1 hour later. Percentage of CD107a+NK cells was determined by flow cytometry.

Expansion and Cytotoxicity of NK Cells in Immunodeficient Mice

To test NK cell expansion in vivo, human NK cells transduced with mbIL15 or mock-transduced (6-9×106 cells per mouse) were injected in the tail vein of NOD.Cg-Prkdc$^{scid}$ IL2rg$^{tm1Wjl}$/SzJ (NOD/scid IL2RGnull) mice (Jackson Laboratories, Bar Harbor, Me.). In some mice, we injected 20000 IU of IL-2 intraperitoneally (i.p.) 3 times per week. On day 7 and 11, blood cells were counted with a cell counter (Beckman Coulter); human and mouse CD45+ cells were enumerated by flow cytometry after treating cells with red cell blood lysis solution (Invitrogen) and staining them with an allophycocyanin-conjugated mouse-anti-human CD45 and a phycoerythrin-conjugated rat anti-mouse CD45 antibodies (both from BD Biosciences). After euthanasia, human NK cells in bone marrow, liver, spleen, kidney, lung, and brain were enumerated as above. All animal experiments were performed in accordance a protocol approved by National University of Singapore Institutional Animal Care and Use Committee.

To test tumor cell killing in mice, we prepared two xenograft models. In the first, U937 cells expressing luciferase were injected i.p. in NOD.Cg-Prkdc$^{scid}$ IL2rg$^{tm1Wjl}$/SzJ (NOD/scid IL2RGnull) mice (1×10$^4$ cells per mouse). Three days later, NK cells transduced with the MSCV vector containing either GFP alone or mbIL15 were injected i.p. (1×10$^7$ cells per mouse); NK cell injection was repeated on day 7. As a control, a group of mice received tissue culture medium instead of NK cells. In the second model, mice were engrafted with ES8 cells (i.p.; 1×10$^5$ cells per mouse), followed by 1 NK cell injection on day 3 as above. Tumor engraftment and progression was evaluated using a Xenogen IVIS-200 system (Caliper Life Sciences, Hopkinton, Mass.), with imaging beginning 5 minutes after i.p. injection of an aqueous solution of D-luciferin potassium salt (3 mg/mouse). Photons emitted from luciferase-expression cells were quantified using the Living Image 4.3.1 software program.

Results

Design of IL-15 Constructs and Expression in NK Cells

As described herein, two forms of the IL15 gene were expressed in human NK cells: a membrane-bound form, resulting from a construct in which the human IL15 gene was linked to the gene encoding the transmembrane domain of CD8α ("mbIL15"), and a wild-type unmodified form ("wtIL15"). Both constructs were inserted in an MCSV retroviral vector containing GFP (FIG. 1A), which was used to transduce proliferating NK cells obtained after culturing peripheral blood mononucleated cells with the stimulatory cell line K562-mb15-41BBL.28 At the end of the cultures, before retroviral transduction, residual T-cells were depleted with anti-CD3 immunomagnetic beads resulting in >95% pure CD56+CD3− cells. Median GFP expression was 71% (23%-97%, n=60) with the construct containing mbIL15, and 69% (range, 20%-91%, n=25) with that containing wtIL15. NK cells from the same donors also transduced with a vector containing only GFP had a median GFP expression of 84% (53%-98%, n=60) (FIG. 1B).

Figure 1B:
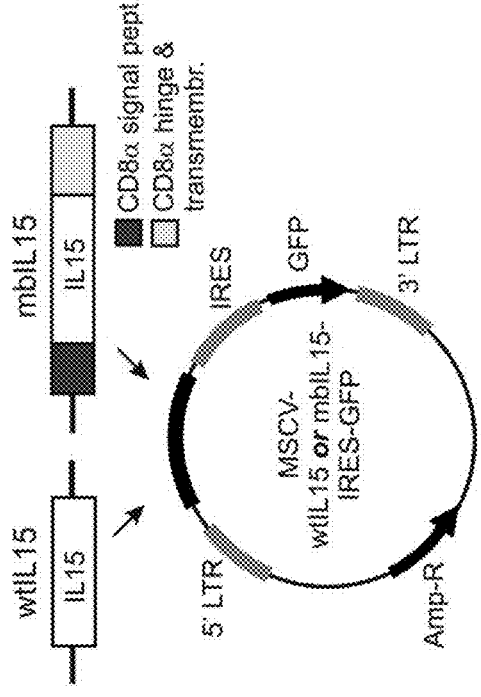
Figure 1C:
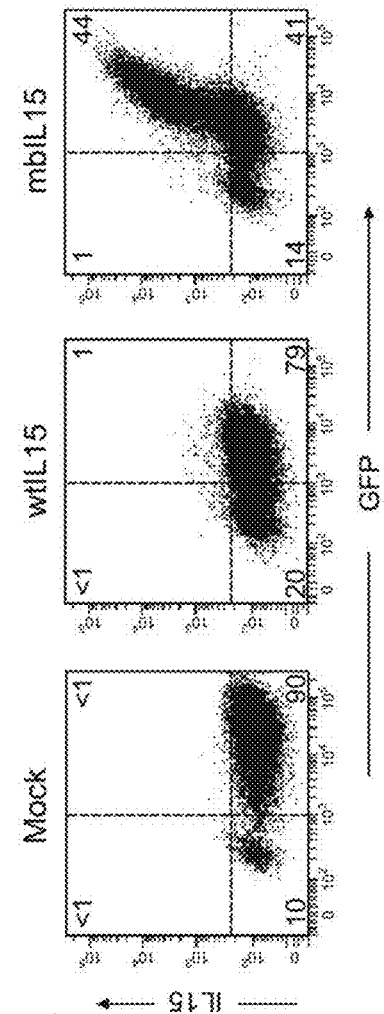

After transduction with mbIL15, IL-15 was expressed on the NK cell membrane: 40%-63% (median, 52; n=7) of GFP+NK cells had IL-15 as detected by an anti-IL15 antibody (FIG. 1B). By contrast, no IL-15 was detectable in cells transduced with wtIL15 (n=4) or mock transduced NK cells (n=7). Production of soluble IL-15 by the transduced NK cells was determined by testing supernatants collected after 24 and 48 hours of culture. A shown in FIG. 1C, cells expressing wtIL15 secreted substantial amounts of IL-15 whereas this was minimal in mbIL15-NK cells and undetectable in mock-transduced NK cells.

NK Cells Expressing IL-15 have Autonomous Survival and Expansion Capacity

To determine whether expression of IL-15 could replace exogenous IL-2 in maintaining NK cell survival, NK cells from 15 donors were transduced with the mbIL15 construct and cultured in the absence of IL-2; cell numbers after culture were then compared to those in parallel cultures with mock-transduced NK cells. As shown in FIG. 2A, expression of mbIL-15 dramatically increased NK cell survival: after 7 days of culture, median cell recovery was 85% while virtually no viable mock-transduced NK cell was detectable (<1%; P<0.0001 by paired t test). The effect of mbIL15 significantly decreased if an anti-IL-15 neutralizing antibody was added to the cultures (FIGS. 6A-6B). In 9 of the 15 donors, recovery of mbIL15 NK cells was also compared to that of NK cells expressing wtIL15: it was significantly higher with the former (median, 85% versus 56%, P=0.026; FIG. 2A).

In parallel experiments, the supportive effects of IL15 expression in the presence of exogenous IL-2 were determined. When cultures contained 10 IU/mL of IL-2, 7-day recovery of NK cells expressing either mbIL15 or wtIL15 remained significantly higher than that of mock-transduced cells; under these conditions, no significant differences were noted between the 2 forms of IL15 (FIGS. 6A-6B). Only when exogenous IL-2 was present at a high concentration (100 IU/mL), 7-day recovery of mock-transduced NK cells matched that of NK cells transduced with IL15 (FIG. 6A).

In experiments with expanded NK cells from 6 of the 9 donors, the capacity of mbIL15 to support NK cell survival beyond 7 days with low dose IL-2 (10 IU/mL) was determined. On day 14, mbIL15 NK cell numbers were maintained or increased in 4 of the 6 cultures; in 2 of these cells had further expanded by day 21. Only 2 of the 6 cultures with mock-transduced NK cells from the same donors had maintained cell numbers on day 14 and 21, and no cell growth was observed; median cell recovery on day 21 was 205% for mbIL15 NK cells and 80% for mock-transduced NK cells. Thus, even in the presence of low dose IL-2, expression mbIL15 conferred a considerable survival and growth advantage.

In cultures of NK cells from one donor, a particularly high cell recovery was observed on day 7 when IL15 was expressed (261% with mbIL15 and 161% with wtIL15 in the absence of IL-2; 266% and 188% with 10 IU/mL IL-2). These cultures were monitored for 2 months and remarkable improvements in cell expansion and survival brought about by the expression of mbIL15 were observed (FIG. 2C). Even in the absence of IL-2, mbIL-15 NK cells continued to survive until day 21 and they were still detectable 75 days after initiation of the culture, while mock-transduced cells had become undetectable on day 7 and wtIL15-transduced NK cells on day 42. In the presence of IL-2 at low concentration (10 IU/mL), the number of mbIL15-expressing NK cells was identical to that originally seeded 2 months after initiation of the cultures, while viable mock-transduced and wtIL15-transduced NK cells had declined much earlier. As shown in FIG. 6B, when IL-2 was added to the culture at a high dose (100 IU/mL), NK cells transduced with either mbIL155 or wtIL15 had a similar persistence profile, both cell types surviving longer than mock-transduced NK cells even under these conditions.

Expansion and Homing of mbIL15 NK Cells In Vivo

Figure 3B:
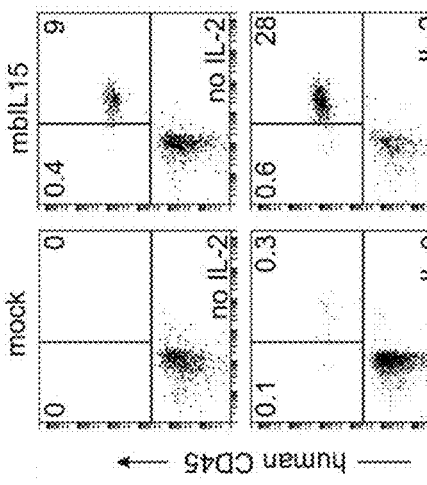
FIG. 3A-3C: Survival and expansion of NK cells expressing mb-IL15 in vivo. 3A. Absolute number of human CD45+ cells in peripheral blood of mice injected with mock- or mbIL15 transduced NK cells with or without IL-2 (16 mice total) 7 and 11 days after infusion (P=0.004 with no IL-2, P=0.021 with IL-2 on day 7; P=0.044 and 0.026 on day 11). 3B. Flow cytometric dot plots illustrate the presence of human CD45+, GFP+NK cells in mouse peripheral blood without (top) and with IL-2 treatment (bottom). Percentages of human CD45+ cells with or without GFP expression is shown. 3C. Percentage of human CD45+ cells in various tissues of mice injected with mock- or mbIL15 transduced NK cells with or without IL-2 collected 11 days after injection. Collectively, percentages of human CD45+ cells were significantly higher with mbIL15 (P<0.001 with no IL-2, P=0.002 with IL-2).
Figure 3A:
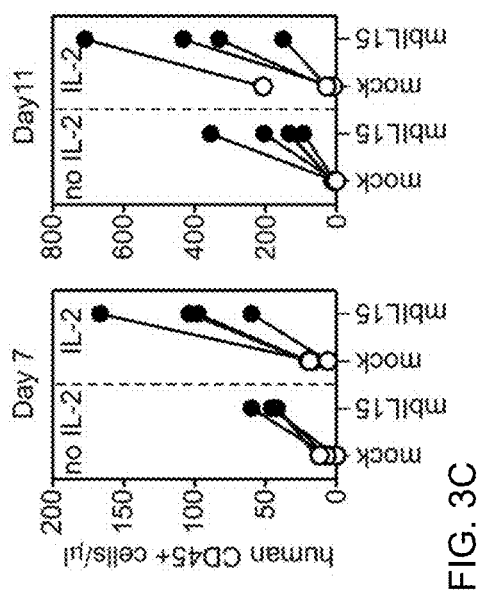

The experiments performed in vitro indicated that IL15 expression improved survival and expansion of NK cells and that mbIL15 produced overall better stimulation. Whether mbIL15 expression would sustain expansion of human NK cells in NOD/scid IL2RGnull mice was next determined. Activated NK cells from 4 donors were transduced with mbIL15 (52%-74% GFP-positive) and injected into 4 mice (one mouse per donor); 4 control mice were injected with mock-transduced NK cells from the same donors. NK cells expressing mbIL15 expanded much more than mock-transduced NK cells: 7 days after injection, median number of mbIL15 NK cells/µl of blood was 44.5 (range, 42-60) versus 6.5 (0-12) with mock-transduced NK cells (P=0.004) (FIG. 3A). Parallel experiments were performed with the same cells, this time also administering 20,000 IU human IL-2 i.p. every 2 days (FIG. 3A). Under these conditions, mbIL15 NK cells expanded even more (median NK cells/µl, 101; range, 60-167), while mock-transduced cells remained low (median, 18; range, 6-20; P=0.021).

On day 11 after injection, mbIL15 NK cells comprised 168.5 cells/µl (range, 94-355) of peripheral blood mononucleated cells in the absence of IL-2 and 382 cells/µl (151-710) when IL-2 was also administered (FIG. 3A, B). By contrast, in mice injected with mock-transduced NK cells, human CD45 cells were virtually undetectable without IL-2, and present at low levels when IL-2 was also injected (median, 27; range 9-207; P=0.026). Human CD45+ cells also expressed CD56 and lack CD3 (not shown). Of note, the proportion of GFP+ had increased from 66.5%±9.9% before injection to 93.8%±4.4% on day 7 and 94.8%±3.4% on day 11 (P<0.01 for both comparisons).

Figure 3C:
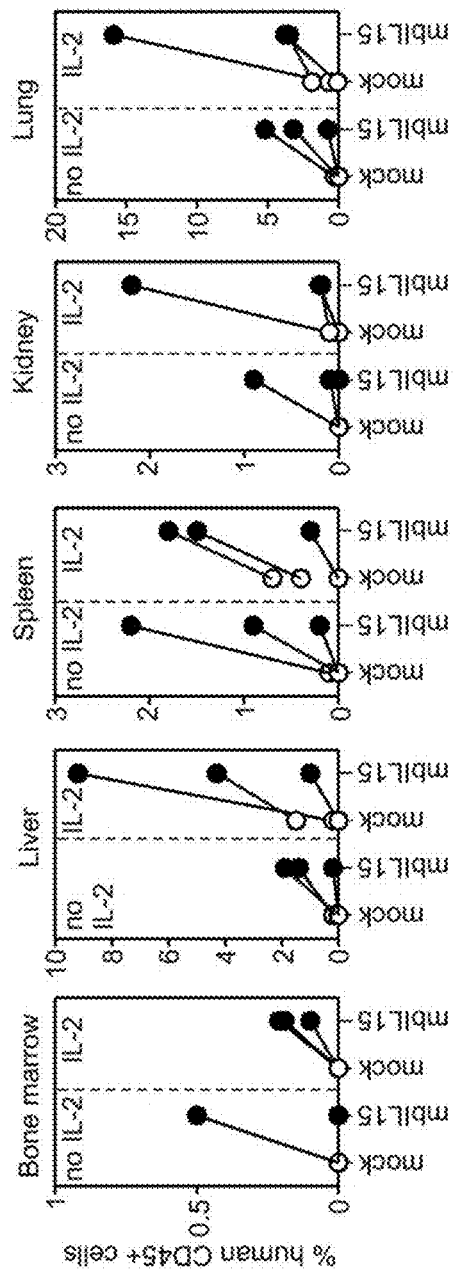
Figure 11A:
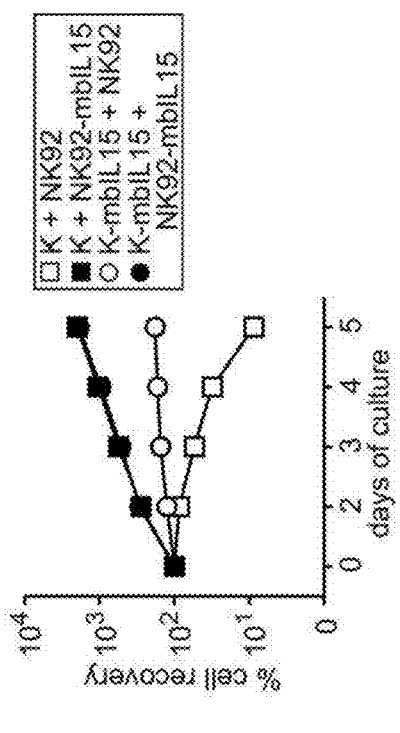
FIGS. 11A-11C: mbIL15 stimulates NK cells by cis presentation. 11A. NK92 cells were transduced with mbIL15 (left) or wtIL15 (right) in a vector containing GFP, sorted to obtain 100% GFP+ cells and co-cultured with untransduced NK92 cells at a 1:1 ratio. Shown is percentage of cell recovery (±SD; n=3) after culture for GFP+ and GFP− cells, relative to the number of cells at the beginning of the culture. 11B. NK92 cells expressing mbIL15 or untransduced were co-cultured with K562 cells ("K") either transduced with mbIL15 or untransduced at 1:2 ratio in the combinations shown. K562 cells were labeled with PKH26 (Sigma) and treated with Streck cell preservative (Streck, Omaha, Nebr.) to prevent cell division before culture. Shown is percentage of NK92 cell recovery (±SD; n=3) after culture, relative to cell numbers at the beginning of the culture. 11C. Proliferation of NK92 cells expressing mbIL15 compared to that of untransduced NK92 cells in the presence of increasing concentrations of exogenous IL-15. Cultures were performed in the absence of IL-2 (left), or with IL-2 at 10 IU/mL (center) or 100 IU/mL (right). Shown is percentage of cell recovery (±SD; n=3) after culture relative to the number of cells at the beginning of the culture.
Figure 11B:
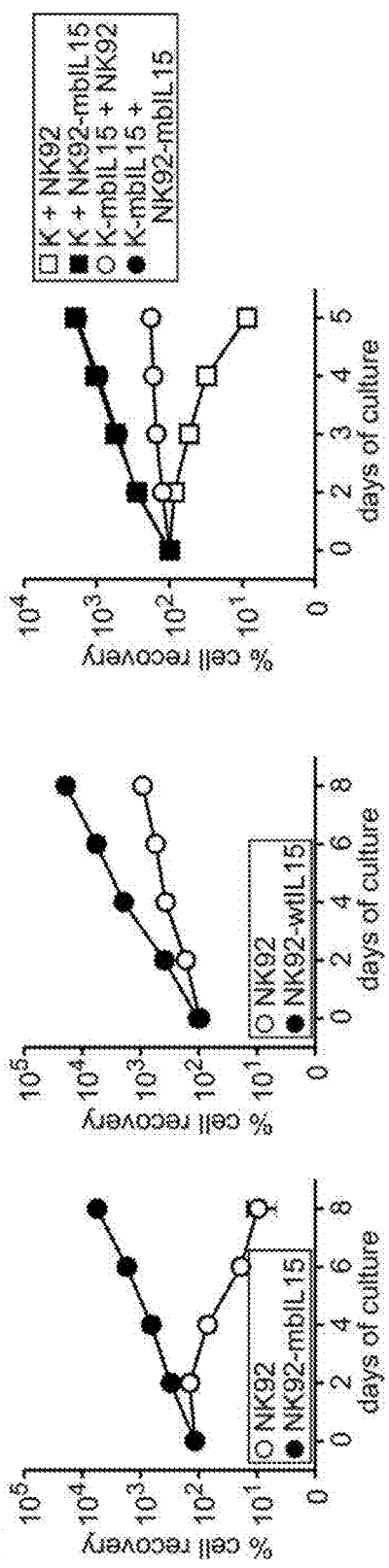
Figure 11C:
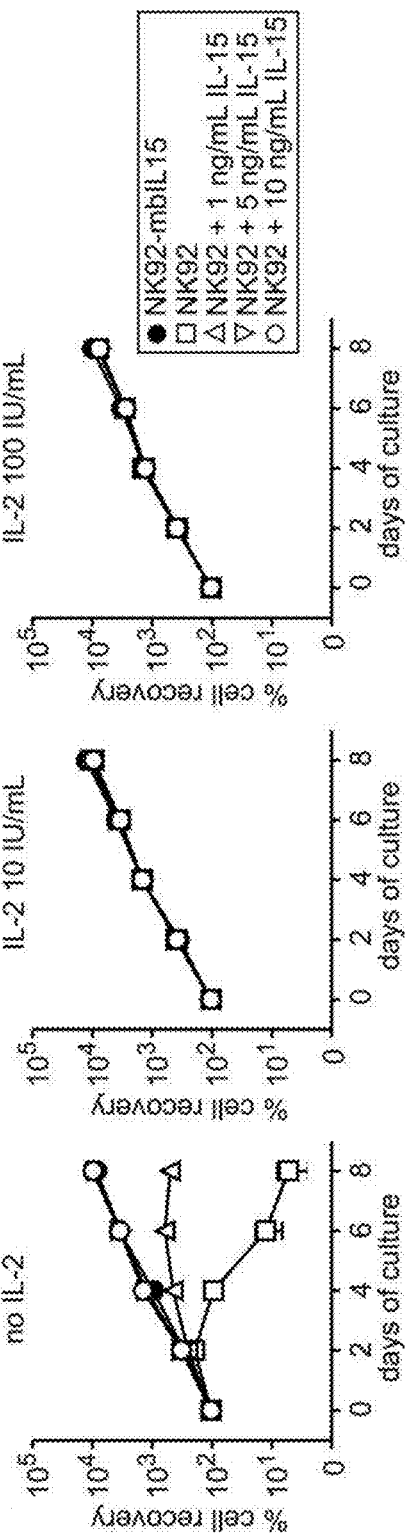
Figure 12A:
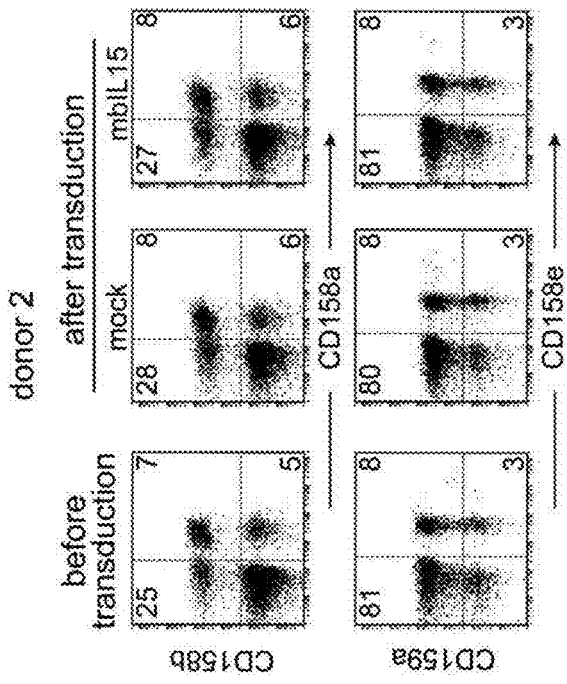
FIGS. 12A-12C. Expression and function of KIRs in mb15-NK cells. 12A. NK cell subsets defined by their KIR expression before transduction, and after mock- or mb15- transduction. Flow cytometric dot plots show results of staining with anti-KIR antibodies in CD56+CD3− cells from 2 donors. Percentages of KIR+ cells are shown. 12B. Results of CD107a expression in CD158a-positive and CD158a-negative subsets after 4-hour culture with 721.221 cells or the same cells expressing the CD158a-binding Cw6 HLA. Shown are mean (±SD) of 4 independent experiments with NK cells from 3 donors (** P<0.0001; *P=0.0002). 12C. Results of IFNγ secretion in the same experiments shown in 12B (** P<0.0001).
Figure 12A:
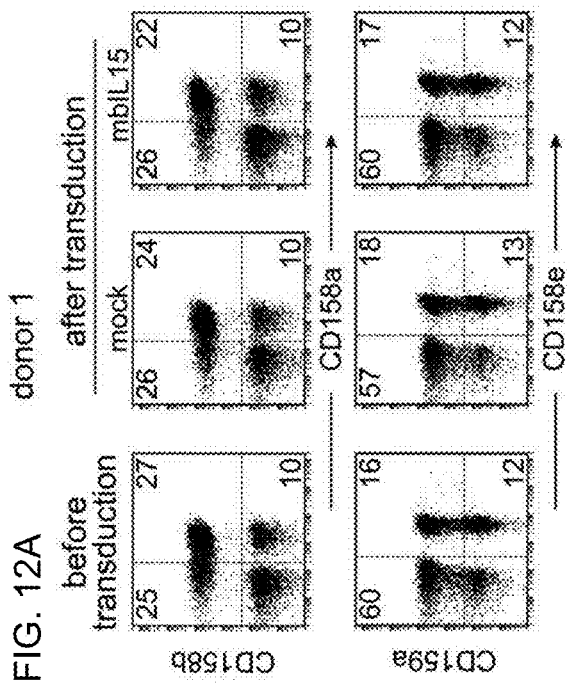
Figure 12B:
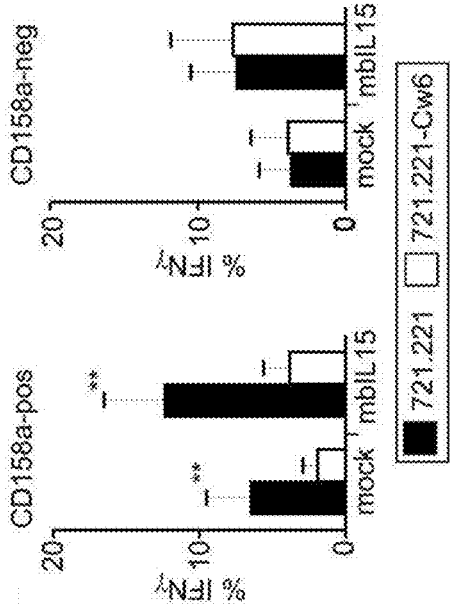
Figure 12C:
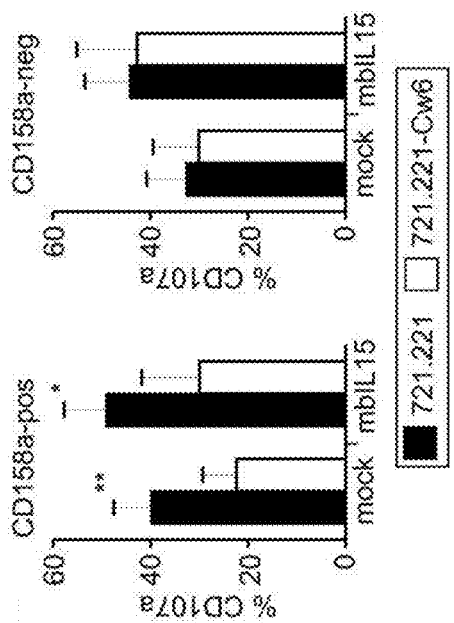
Figure 13A:
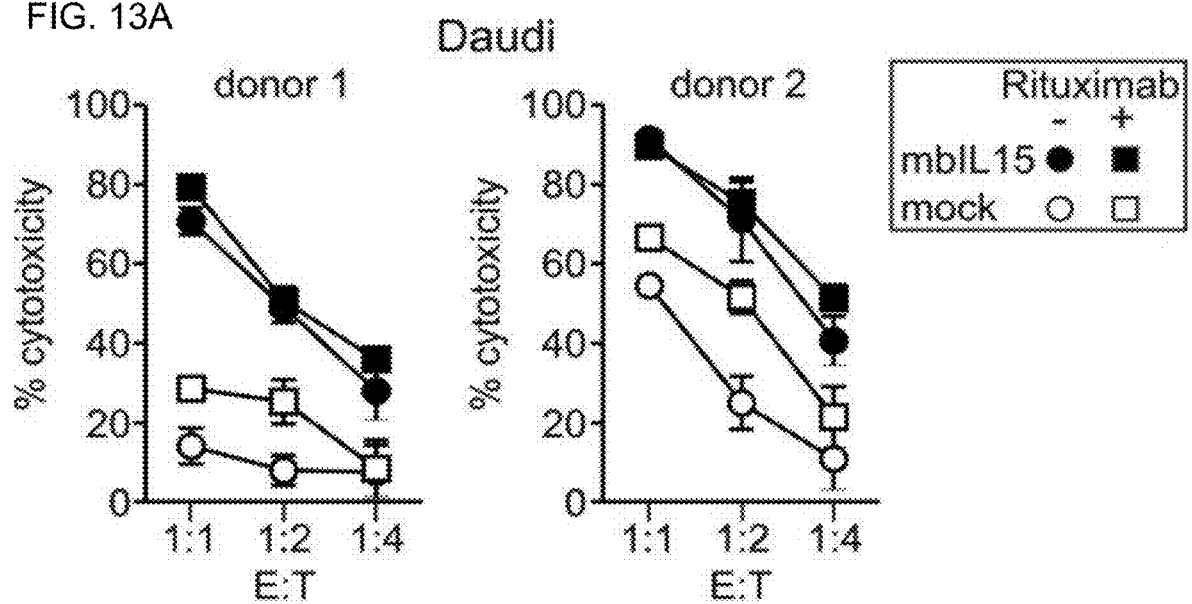
FIGS. 13A and 13B: Antibody-dependent cell cytotoxicity (ADCC) of NK cells expressing mbIL15. Results of 4-hour ADCC assays with mbIL15- and mock-transduced NK cells against (13A) Daudi and (13B) SK-BR-3 in the presence of Rituximab or Trastuzumab, respectively; IgG at the same concentration of the immunotherapeutic antibodies (1 μg/mL) was used as a control. Each symbol indicates mean±SD cytotoxicity in experiments with NK cells from each donor in triplicate. In the presence of immunotherapeutic antibodies, mbIL15-NK cells exerted significantly higher ADCC than mock-transduced cells (P<0.001 for either donor in tests with Daudi or SK-BR-3). Cytotoxicity by mbIL15-NK cells without antibody was also significantly higher (P<0.001 for either donor in tests with Daudi or SK-BR-3).
Figure 13B:
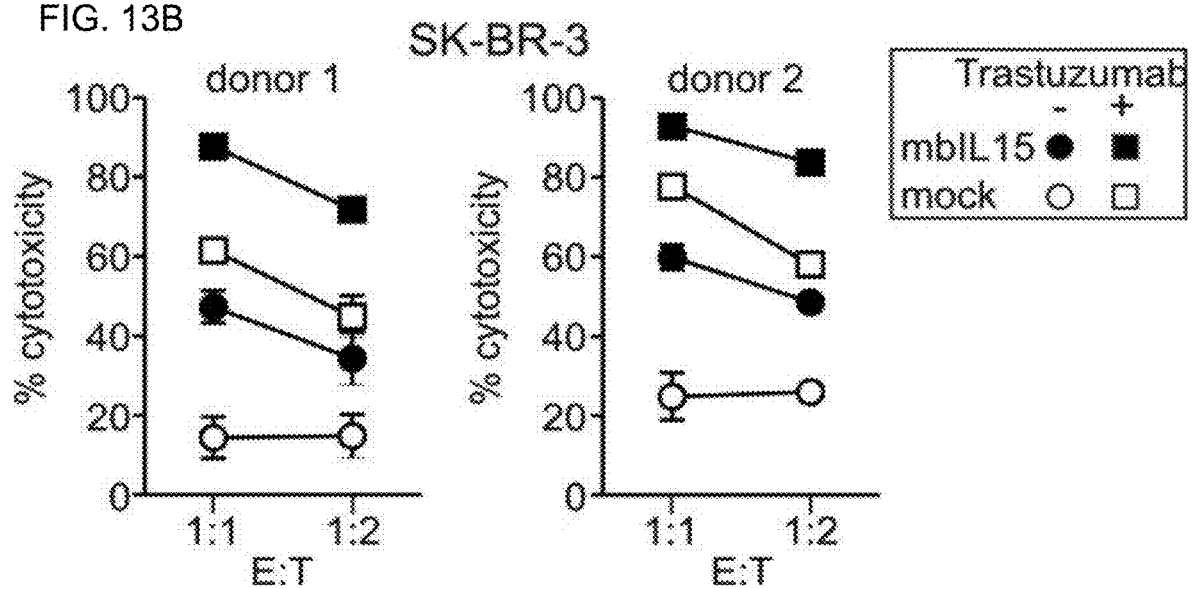

After euthanasia on day 11, 3 of the 4 mice were examined for the presence of human CD45+ cells in various tissues. If mbIL15 was expressed, considerable numbers of human NK cells were detected in bone marrow, liver, spleen, kidney and lung; in all tissues, numbers were markedly higher than those seen with mock-transduced cells (FIG. 3C): mean (±SD) percentage of CD45+ cells expressing mbIL15 was 1.2%±1.5% with no IL-2 and 3.0%±4.3% with IL-2, as compared to 0.04%±0.09% and 0.4%±0.6% with mock-transduced cells (P<0.001 and P=0.002, respectively). The only exception was brain where neither mbIL15- nor mock-transduced NK cells could be detected.

Mechanisms of mbIL15 Stimulation

To determine whether mbIL15 predominantly stimulated cells in trans (IL-15 presented on one NK cell stimulating a neighboring cell (a mechanism reported to occur physiologically)) or cis (by direct binding of mbIL15 to receptors expressed in the same cell), the proportions of GFP+ and GFP− NK cells in the cultures were evaluated after 7 days of culture. If the trans mechanism was predominant, the ratio between GFP+ and GFP− NK cells should remain unaltered during culture; if cis was predominant, the proportion of GFP+ cells should increase. FIG. 4A shows the results of such analysis: the percentage of GFP+ cells among NK cells examined after 7 days of culture without IL-2 consistently increased if mbIL15 was expressed whereas it did not in cultures with mock-transduced cells: GFP+ cells constituted 95.9%±3.3% of the total cell population versus 57.5%±18.6% on day 7 (P<0.0001), as compared to 71.2%±19.0% versus 80.5%±17.1% on day 0. Thus, the predominant mechanism of stimulation by mbIL-15 expressed in NK cells is autocrine.

Cells expressing mbIL15 essentially retained the immunophenotype of activated NK cells. However, when examined 2 days after IL-2 withdrawal compared to mock-transduced NK cells, mbIL15 NK cells expressed moderately higher levels of the activation receptors NKG2D, NKp44 (CD336) and NKp30 (CD337) as well as of CD16 and CD56, while expression of NKp46 (CD335) decreased and that of other molecules, such as DNAM-1 (CD226), remained unchanged (FIG. 4B; the Table). The signal transduction pathways activated by the expression of mbIL15 were also determined. As shown in FIG. 4C, in comparison to mock-transduced NK cells, mbIL-15 NK cells had several highly phosphorylated molecules. These included molecules known to be phosphorylated in response to IL-15 signaling, such as the transcription factors STAT1, STAT3 and STAT5, the kinases src, Erk1/2 and Mek1. Notably, a marked phosphorylation of Bad, as well as phosphorylation of Caspase 7 and 9, collectively indicative of an anti-apoptotic effect, were observed. Other highly phosphorylated molecules in mbIL15 NK cells whose role in IL-15 signaling is unclear included CDK6 and RafA.

Effects of mbIL-15 on NK Cell Anti-Tumor Cytotoxicity In Vitro and In Vivo

The improvements in NK cell survival and proliferation brought about by expression of mbIL15 indicated that NK-mediated killing of tumor cells would likely also increase. This notion was first tested by comparing tumor cell cytotoxicity exerted by mbIL15-NK cells to that of mock transduced NK cells from the same donors. Experiments with NK cells from 9 donors targeting the leukemia cell lines Nalm-6 (B-lineage acute lymphoblastic leukemia), U937 and K562 (acute myeloid leukemia), as well as Daudi (B-cell lymphoma), SKBR3 (breast carcinoma) and ES8 (Ewing sarcoma) at different E:T ratios and co-culture durations, for a total of 90 experiments, were performed. FIG. 5A shows results of 24-hour assays: median cytotoxicity was 22% with mock-transduced NK cells at 1:4 E:T and 54% at 1:1 E:T; with mbIL15 NK cells, it was 71% and 99%, respectively (P<0.0001). Results with individual cell lines are shown in FIGS. 7A-7B. Although the increased cytotoxicity might be related to the increase survival of NL cells in culture, an increased release of lytic granules by mbIL15-NK cells, as revealed by CD107a staining after culture with either K562 or U937 cells, was also observed (P=0.0067; FIG. 5B).

The gains in vitro cytotoxicity associated with expression of mbIL15 were reflected in experiments with NOD/scid IL2RGnull mice engrafted with human tumor cells. In one set of experiments, mice were injected with the human acute myeloid leukemia (AML) cell line U937 and then treated with either mbIL15- or mock-transduced NK cells. As shown in FIGS. 5C and 5D, mice receiving mbIL15-transduced NK cells had a slower tumor growth and a significantly longer survival than untreated mice and those treated with mock-transduced NK cells (P=0.014, log rank test for trend). The cells were also tested in a second xenograft model in which NOD/scid IL2RGnull mice were injected with the Ewing sarcoma cell line ESB, which has a much slower growth rate, and the mice were treated with one injection of NK cells. As shown in FIGS. 8A-8C, the outcome of mice treated with mbIL15 NK cells (n=12) was superior to that of mock-transduced NK cells (n=11) and of untreated mice (n=7): median survival was 162, 49 and 21 days, respectively (P=0.005).

DISCUSSION

Among the factors that determine the success of NK cell-based therapy of cancer, perhaps the most fundamental one is that NK cells persist in sufficient numbers to achieve an E:T ratio likely to produce tumor cytoreduction. Demonstrated herein is that expression of a membrane-bound form of IL-15 in human NK cells supported their autonomous expansion and extended survival in the absence of IL-2. NK cells expressing mbIL15 could be maintained in vitro for up to 2 months without exogenous IL-2. NK cells expressing mbIL15 could expand in immunodeficient mice and infiltrated multiple tissues where they could be found in much larger numbers than mock-transduced cells. Expansion of mbIL-15 NK cells was further increased by a low concentration of IL-2 both in vitro and in vivo. Expression of mbIL15 did not impair the cytotoxic capacity of NK cells. In fact, in xenograft models, mbIL15 NK cells exerted anticancer activity which was more powerful than that of mock-transduced cells, indicating that this approach might improve the antitumor capacity of NK cell infusions while averting the side effects of IL-2 administration.

The findings herein show that ectopic expression of IL-15 in human NK cells caused a stronger survival-promoting effect when IL-15 was presented in a membrane-bound form than in a secreted form. Notably, however, mbIL15 expressed in NK cells preferentially stimulates in cis rather than in the trans when IL-15 is presented by other cells. That is, mbIL15 appears to preferentially engage IL-15 receptors on the same cells, resulting in autocrine stimulation. This mechanism explains the IL-15 expression pattern that was consistently observed when mbIL15-transduced NK cells were labeled with an anti-IL-15 antibody, showing a substantial proportion of cells with strong GFP expression but ostensibly lacking IL-15 (FIG. 1B). It is hypothesized that in these cells IL-15 is expressed but not accessible to antibody because it is bound to its receptor and/or internalized. The capacity of mbIL15 to promote NK cell viability likely explains the increased cytotoxicity exerted by these cells, particularly in 24-hour in vitro assays and in vivo. However, the superiority of mbIL15-NK cells was also clear in short-term (4-hour) assays and these cells also released more lytic granules according to the CD107a test. Therefore, expression of mbIL15 is likely to increase NK cell cytotoxicity by other means, possibly by enhancing their activation status.

Clinical administration of NK cells typically relies on IL-2 to support their survival and expansion in vivo. The multiple side effects related to IL-2 administration, however, are potentially serious and often render administration of this cytokine poorly tolerated. Stopping IL-2 administration or reducing its dose may results in decreased NK cell expansion and inefficient anti-tumor effect, which may be further inhibited by the stimulation of regulatory T cells. To this end, replacing IL-2 with IL-15 is potentially attractive but the clinical formulation of IL-15 is still being tested. Although it was overall well tolerated when administered to rhesus macaques, adverse effects were observed in some animals, including diarrhea, emesis, weight loss, transient neutropenia, increase in transaminases and hyponatremia. In addition to T and NK cell expansion, expansion of regulatory T cells has been observed. Contrary to NK cells transduced with wtIL15, those transduced with mbIL15 released exceedingly small amount of IL-15 in the supernatant. Thus, any potential side effect that may be caused by the interaction of IL-15 with cells other than NK cells should be minimized by this approach. Of note, prolonged exposure of murine large granular lymphocytes to IL-15 leads to their leukemic growth. This poses a potential safety concern for IL-15 administration in patients and also for the use of NK cells expressing IL-15, particularly if such cells were administered to patients at a low risk of relapse. In the experiments described herein, however, NK cells expressing mbIL15 generally survived for much shorter periods than the one year or more reported for T cell clones expressing soluble IL-15. Moreover, persistent NK expansion was not observed in immunodeficient mice, with a follow-up exceeding 9 months.

There is considerable clinical evidence supporting the anti-cancer potential of NK cells. NK cells also play a critical role in mediating antibody-dependent cell cytotoxicity in patients treated with monoclonal antibodies. Thus, infusion of NK cells is likely beneficial in multiple settings. Expansion of human NK cells in large numbers ex vivo is feasible; robust large-scale methods for this purpose have been established and are being used in clinical trials. Genetic modification of NK cells by retroviral transduction or electroporation is also possible. Therefore, the translation of the approach described herein into clinical-grade conditions is realistic and it is warranted by the superior expansion and cytotoxicity of mbIL15-NK cells.

TABLE

Surface marker expression in mock- and mbIL15 transduced NK cells[1]

| Marker | Mock %[2] | Mock MFI | mb15 % | mb15 MFI |
|---|---|---|---|---|
| CD56 | 100 | 44190 | 100 | 56721[3] |
| CD16 | 88 | 7789 | 92 | 10784 |
| CD69 | 90 | 3057 | 91 | 4481 |
| CD25 (IL2Rα) | 56 | 631 | 75 | 795 |
| CD122 (IL2Rβ/IL15Rβ) | 100 | 4833 | 99 | 3216 |
| CD132 (IL2Rγ) | 89 | 943 | 97 | 1263 |
| NKG2D | 99 | 2846 | 100 | 4953 |
| CD335 (NKp46) | 89 | 2613 | 89 | 2236 |
| CD336 (NKp44) | 84 | 9455 | 83 | 11530 |
| CD337 (NKp30) | 91 | 1286 | 95 | 2678 |
| CD226 (DNAM-1) | 99 | 16440 | 99 | 16905 |
| CD158ah (KIR2DL1, KIR2DS1) | 23 | 6747 | 24 | 11793 |
| CD158b | 49 | 42515 | 47 | 51247 |
| CD158e | 22 | 4225 | 22 | 4946 |
| CD159a | 68 | 18133 | 73 | 21106 |

[1]Cell markers were analyzed after 48 hours of culture in the absence of IL-2. Antibodies were from BD Biosciences (CD56 PE, CD16 PE-Cy7, CD69 PE, CD25 PE-Cy7, CD122 BV421, CD158b PE), Beckman Coulter (CD335 PE, CD336 PE, CD337 PE, CD158ah PE, CD159a PE), Miltenyi Biotech (CD226 PE, CD158e APC), R&D Systems (NKG2D PE), Biolegend (CD132 APC).
[2]Percentages refer to GFP+ cells expressing the marker.
[3]Overexpressed markers are highlighted in bold font.
MFI, mean fluorescence intensity The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method of treating a cancer, the method comprising: administering to a subject having the cancer a population of cells that express all or a functional portion of interleukin-15 (IL-15), wherein the all or a functional portion of the IL-15 is fused to all or a portion of a transmembrane protein and results in the IL-15 being expressed as a cell membrane-bound polypeptide (mbIL15) on the surface of the cells,
wherein the transmembrane protein is a CD8 transmembrane domain, and
wherein the mbIL15 has the sequence of SEQ ID NO: 2.

2. The method of claim 1, wherein the population of cells comprises one or more of natural killer (NK) cells, T-cells, dendritic cells and monocytes.

3. The method of claim 2, wherein the population of cells comprises isolated CD56+CD3⁻ natural killer cells.

4. The method of claim 1, wherein the mbIL15 activates IL-15 signaling and/or anti-apoptotic signaling in an autocrine manner.

5. The method of claim 1,
wherein the immune cells expressing mbIL15 exhibit enhanced expression of one or more activation receptors as compared to immune cells not expressing mbIL15, wherein the one or more activation receptors are selected from NKG2D, NKp44 (CD336) and NKp30 (CD337), CD16 or CD56.

6. The method of claim 1, wherein the cancer is selected from leukemia, a myelodysplastic syndrome, a lymphoma, a solid tumor or a sarcoma.

7. The method of claim 6, wherein the cancer is a leukemia, and wherein the leukemia is acute lymphoblastic leukemia, acute myeloid leukemia, chronic myelogenous leukemia, or chronic lymphocytic leukemia.

8. The method of claim 1, further comprising administering IL-2 to the individual.

9. The method of claim 8, wherein the IL-2 is administered at a dose of 1 million IU/m² or less.

10. The method of claim 1, further comprising administering one or more antibodies directed against the cancer to the individual.

11. A method of treating cancer, the method comprising: administering to a subject having the cancer a population of immune cells that expresses all or a functional portion of interleukine-15 (IL15) fused to all or a functional portion of a transmembrane domain of a transmembrane protein, resulting in the IL-15 being expressed as a membrane-bound IL-15 (mbIL15) on the surface of the immune cells,
wherein the mbIL15 has the sequence of SEQ ID NO:2,
wherein the population of cells comprises one or more of natural killer (NK) cells, T-cells, dendritic cells and monocytes, and wherein the mbIL15 promotes one or more of:
(i) natural killer (NK) cell survival,
(ii) regulation of NK cell and T-cell activation and proliferation, and
(iii) support of NK cell development from hematopoietic stem cells.

12. The method of claim 11, wherein the all or a functional portion of the transmembrane protein is from a CD8α transmembrane protein.

13. The method of claim 11, wherein the all or a functional portion of the IL-15 comprises all or a functional portion of the amino acid sequence of SEQ ID NO: 4.

14. The method of claim 11, wherein the population of cells exhibits enhanced phosphorylation of one or more of STAT1, STAT3 and STAT5, Src, Erkl/2 or Mek as compared to a population of cells not expressing mbIL15, and wherein the population of cells expressing mbIL15 exhibits enhanced anti-apoptotic signaling as compared to a population of cells not expressing mbIL15.

15. A method of treating a cancer, comprising administering to a subject having the cancer a population of immune cells that expresses a membrane-bound interleukin 15 (mbIL15), wherein the mbIL15 comprises the amino acid sequence of SEQ ID NO: 2,
wherein the population of cells comprises one or more of natural killer (NK) cells, T-cells, dendritic cells and monocytes, and wherein the mbIL15 promotes one or more of:

(i) natural killer (NK) cell survival,
(ii) regulation of NK cell and T cell activation and proliferation, and
(iii) support of NK cell development from hematopoietic stem cells.

16. A method of treating a cancer, the method comprising: administering to a subject having the cancer a population of immune cells that expresses all or a functional portion of interleukin-15 (IL-15) as a cell membrane-bound polypeptide (mbIL15), wherein mbIL15 comprises the amino acid sequence of SEQ ID NO. 2.

17. The method of claim 16, further comprising administering IL-2 to the individual.

18. The method of claim 16, wherein the cancer is selected from leukemia, a myelodysplastic syndrome, a lymphoma, a solid tumor or a sarcoma.

* * * * *

UNITED STATES PATENT AND TRADEMARK OFFICE
CERTIFICATE OF CORRECTION

PATENT NO. : 11,560,548 B2
APPLICATION NO. : 16/986742
DATED : January 24, 2023
INVENTOR(S) : Dario Campana, David Shook and Masaru Imamura It is certified that error appears in the above-identified patent and that said Letters Patent is hereby corrected as shown below:

In the Claims

In Claim 11, Column 26, Line 26, delete "treating cancer," and insert -- treating a cancer, --.

In Claim 11, Column 26, Line 29, delete "interleukine-15 (IL15)" and insert -- interleukin-15 (IL-15) --.

In Claim 14, Column 26, Line 53, delete "STATS," and insert -- STAT5, --.

In Claim 15, Column 27, Line 2, delete "T cell" and insert -- T-cell --.

In Claim 16, Column 27, Line 11, delete "SEQ ID NO. 2." and insert -- SEQ ID NO: 2. --.

Signed and Sealed this
Fourteenth Day of March, 2023

Katherine Kelly Vidal
*Director of the United States Patent and Trademark Office*